(12) United States Patent (10) Patent No.: US 8,560,080 B2
Goetz et al. (45) Date of Patent: Oct. 15, 2013

(54) PROGRAMMING TECHNIQUES FOR CONTROLLING RATE OF CHANGE OF ELECTRICAL STIMULATION THERAPY

(75) Inventors: Steven M. Goetz, North Oaks, MN (US); Rajeev M. Sahasrabudhe, Maple Grove, MN (US); Jon P. Davis, St. Michael, MN (US); Brent A. Huhta, Big Lake, MN (US); Ashish Singal, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/156,011

(22) Filed: Jun. 8, 2011

(65) Prior Publication Data

US 2011/0307032 A1 Dec. 15, 2011

Related U.S. Application Data

(60) Provisional application No. 61/397,419, filed on Jun. 11, 2010, provisional application No. 61/353,842, filed on Jun. 11, 2010.

(51) Int. Cl.
*A61N 1/00* (2006.01)
(52) U.S. Cl.
USPC .......................................................... 607/59
(58) Field of Classification Search
USPC ............ 607/59, 72, 46, 45, 30, 116; 600/407, 600/372
See application file for complete search history.

(56) References Cited

U.S. PATENT DOCUMENTS

| | | |
|---|---|---|
| 4,592,359 A | 6/1986 | Galbraith |
| 4,931,795 A | 6/1990 | Gord |
| 5,190,035 A | 3/1993 | Salo et al. |
| 5,241,472 A | 8/1993 | Gur et al. |
| 5,501,703 A | 3/1996 | Holsheimer et al. |
| 5,713,922 A | 2/1998 | King |
| 5,776,172 A | 7/1998 | Schulman et al. |
| 5,800,465 A | 9/1998 | Thompson et al. |
| 5,895,416 A | 4/1999 | Barreras, Sr. et al. |
| 5,916,238 A | 6/1999 | Hauser et al. |
| 5,954,758 A | 9/1999 | Peckham et al. |
| 6,341,234 B1 | 1/2002 | Thong et al. |

(Continued)

FOREIGN PATENT DOCUMENTS

| | | |
|---|---|---|
| EP | 2039391 A1 | 3/2009 |
| WO | WO 0154579 A1 | 8/2001 |

(Continued)

OTHER PUBLICATIONS

Office Action from U.S. Appl. No. 12/769,149, dated Sep. 26, 2011, 21 pp.

(Continued)

*Primary Examiner* — Robert N Wieland
(74) *Attorney, Agent, or Firm* — Shumaker & Sieffert, P.A.

(57) ABSTRACT

Techniques are described, for medical devices that deliver electrical stimulation therapy, for controlling a transition from an initial stimulation location or initial stimulation shape to a user-specified target stimulation location or target stimulation shape in order to limit the rate of change of stimulation. One example method includes receiving, via a programmer for an electrical stimulator, user input indicating a target stimulation zone, and controlling the electrical stimulator to transition electrical stimulation from an initial stimulation zone to the target stimulation zone via one or more intermediate stimulation zones.

56 Claims, 29 Drawing Sheets

(56) References Cited

U.S. PATENT DOCUMENTS

| | | |
|---|---|---|
| 6,393,325 B1 | 5/2002 | Mann et al. |
| 6,421,564 B1 | 7/2002 | Yerich et al. |
| 6,505,078 B1 | 1/2003 | King et al. |
| 6,516,227 B1 | 2/2003 | Meadows et al. |
| 6,587,724 B2 | 7/2003 | Mann |
| 6,609,032 B1 | 8/2003 | Woods et al. |
| 6,625,482 B1 | 9/2003 | Panescu et al. |
| 6,799,070 B2 | 9/2004 | Wolfe et al. |
| 6,853,863 B2 | 2/2005 | Carter et al. |
| 6,895,280 B2 | 5/2005 | Meadows et al. |
| 6,909,917 B2 | 6/2005 | Woods et al. |
| 7,035,690 B2 | 4/2006 | Goetz |
| 7,127,297 B2 | 10/2006 | Law et al. |
| 7,174,210 B1 | 2/2007 | Levine |
| 7,180,760 B2 | 2/2007 | Varrichio et al. |
| 7,216,001 B2 | 5/2007 | Hacker et al. |
| 7,251,529 B2 | 7/2007 | Greenwood-Van Meerveld |
| 7,271,663 B2 | 9/2007 | Baum et al. |
| 7,317,948 B1 | 1/2008 | King et al. |
| 7,386,348 B2 | 6/2008 | North et al. |
| 7,387,603 B2 | 6/2008 | Gross et al. |
| 7,389,147 B2 | 6/2008 | Wahlstrand et al. |
| 7,463,928 B2 | 12/2008 | Lee et al. |
| 7,477,723 B2 | 1/2009 | Kamegawa et al. |
| 7,505,809 B2 | 3/2009 | Strommer et al. |
| 7,519,428 B1 | 4/2009 | Palmer |
| 7,519,431 B2 | 4/2009 | Goetz et al. |
| 7,526,341 B2 | 4/2009 | Goetz et al. |
| 7,567,834 B2 | 7/2009 | Clayton et al. |
| 7,571,007 B2 | 8/2009 | Erickson et al. |
| 7,623,918 B2 | 11/2009 | Goetz |
| 7,768,151 B2 | 8/2010 | Andreu et al. |
| 7,974,697 B2 * | 7/2011 | Maschino et al. .............. 607/45 |
| 2004/0059395 A1 | 3/2004 | North et al. |
| 2004/0098063 A1 | 5/2004 | Goetz |
| 2004/0210273 A1 | 10/2004 | Wang |
| 2004/0267330 A1 | 12/2004 | Lee et al. |
| 2005/0131464 A1 | 6/2005 | Heinrich et al. |
| 2006/0195145 A1 | 8/2006 | Lee et al. |
| 2006/0229687 A1 | 10/2006 | Goetz et al. |
| 2006/0241720 A1 | 10/2006 | Woods et al. |
| 2006/0259079 A1 | 11/2006 | King |
| 2006/0259099 A1 | 11/2006 | Goetz et al. |
| 2006/0293609 A1 | 12/2006 | Stahmann et al. |
| 2007/0100408 A1 | 5/2007 | Gerber et al. |
| 2007/0203537 A1 | 8/2007 | Goetz et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0203546 A1 | 8/2007 | Stone et al. |
| 2008/0004674 A1 | 1/2008 | King et al. |
| 2008/0046036 A1 | 2/2008 | King et al. |
| 2008/0071324 A1 | 3/2008 | Miesel et al. |
| 2008/0082137 A1 | 4/2008 | Kieval et al. |
| 2008/0109048 A1 | 5/2008 | Moffitt |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0215119 A1 | 9/2008 | Woods et al. |
| 2008/0221637 A1 * | 9/2008 | Woods et al. .................. 607/30 |
| 2008/0288023 A1 | 11/2008 | John |
| 2008/0294211 A1 | 11/2008 | Moffitt |
| 2009/0018617 A1 | 1/2009 | Skelton et al. |
| 2009/0024189 A1 | 1/2009 | Lee et al. |
| 2009/0149917 A1 | 6/2009 | Whitehurst et al. |
| 2010/0023069 A1 | 1/2010 | Moffitt et al. |
| 2010/0023070 A1 | 1/2010 | Moffitt et al. |
| 2010/0106219 A1 | 4/2010 | Torgerson et al. |
| 2011/0093044 A1 * | 4/2011 | Moffitt ............................ 607/59 |
| 2011/0313268 A1 * | 12/2011 | Kokones et al. .............. 600/372 |

FOREIGN PATENT DOCUMENTS

| | | |
|---|---|---|
| WO | WO 2009076211 A1 | 6/2009 |
| WO | 2009137121 A1 | 11/2009 |
| WO | WO 2009134480 A1 | 11/2009 |
| WO | WO 2010011721 A1 | 1/2010 |

OTHER PUBLICATIONS

Response to Office Action dated Sep. 26, 2011, from U.S. Appl. No. 12/769,149, filed Dec. 19, 2011, 21 pp.

Office Action from U.S. Appl. No. 12/906,418, dated Mar. 7, 2012, 18 pp.

Response to Office Action dated Mar. 7, 2012, from U.S. Appl. No. 12/906,418, filed Jun. 28, 2012, 19 pp.

Bourret et al., "Programmable High-Amplitude Balanced Stimulus Current-Source for Implantable Microstimulators," Proceedings of the 19th Annual International Conference of the IEEE Engineering in Medicine and Biology Society, Oct. 30-Nov. 2, 1997, pp. 1938-1941.

Kim et al., "A 64-Site Multishank CMOS Low-Profile Neural Stimulating Probe," IEEE Journal of Solid State Circuits, vol. 31, No. 9, Sep. 1996, pp. 1230-1238.

St-Amand et al., "Design and Optimization of a Low DC Offset CMOS Current-Source Dedicated to Implantable Miniaturized Stimulators," Analog Integrated Circuits and Signal Processing, vol. 11, 1996, pp. 47-61.

Final Office Action from U.S. Appl. No. 12/906,418, Aug. 10, 2012, 15 pp.

Office Action from U.S. Appl. No. 12/769,149, Jul. 27, 2012, 8 pp.

Lee et al., "AIM Targeting Technique: A Novel Method of Focusing the Volume of Activation on the Dorsal Column with Multiple Independent Current Control in a Computational Model," Boston Scientific Neuromodulation, Valencia, California, presented at 13th North American Neuromodulation Society Annual Meeting, Las Vegas, Nevada, Dec. 3-6, 2009, Poster ID A107, 2 pp.

U.S. Appl. No. 61/048,774, by John C. Rondoni, filed Apr. 29, 2008.

U.S. Appl. No. 12/696,988, by Nathan A. Torgerson, filed Jan. 29, 2010.

U.S. Appl. No. 12/696,992, by Nathan A. Torgerson, filed Jan. 29, 2010.

U.S. Appl. No. 12/906,418, by Steven M. Goetz, filed Oct. 18, 2010.

U.S. Appl. No. 12/769,149, by Nathan A. Torgerson, filed Apr. 28, 2010.

U.S. Appl. No. 12/829,089, by Nathan A. Torgerson, filed Jul. 1, 2010.

U.S. Appl. No. 13/073,562, by Jon P. Davis, filed Jul. 1, 2010.

U.S. Appl. No. 12/829,108, by Steven M. Goetz, filed Mar. 28, 2010.

Notification of Transmittal of the International Search Report and the Written Opinion of the International Searching Authority for corresponding patent application No. PCT/US2011/039777, mailed Aug. 29, 2011, 14 pages.

Abstract of: Bian et al., "Double electrodes simultaneous stimulation and implantation technique in deep brain stimulation," Chin J. Traumatol 8(4):253-256, Aug. 2005.

Office Action from U.S. Appl. No. 12/829,108, dated Sep. 17, 2012, 34 pp.

Office Action from U.S. Appl. No. 12/696,992, dated Sep. 13, 2012, 6 pp.

Office Action from U.S. Appl. No. 12/696,988, dated Dec. 14, 2010, 26 pp.

Response to Office Action dated Sep. 13, 2012, from U.S. Appl. No. 12/696,992, filed Dec. 10, 2012, 14 pp.

Response to Office Action dated Jul. 27, 2012, from U.S. Appl. No. 12/769,149, filed Nov. 20, 2012, 18 pp.

Response to Office Action dated Oct. 17, 2012, from U.S. Appl. No. 12/829,089, filed Dec. 18, 2012, 16 pp.

Response to Office Action dated Sep. 17, 2012, from U.S. Appl. No. 12/829,108, filed Dec. 14, 2012, 24 pp.

Office Action from U.S. Appl. No. 12/829,108, filed Jan. 9, 2013, 33 pp.

Office Action from U.S. Appl. No. 12/696,992, dated Jan. 9, 2013, 5 pp.

(56) References Cited

OTHER PUBLICATIONS

Office Action from U.S. Appl. No. 12/829,089, dated Oct. 17, 2012, 29 pp.
Response to Office Action dated Aug. 10, 2012, from U.S. Appl. No. 12/906,418, filed Oct. 9, 2012, 19 pp.
Response to office Action for U.S. Appl. No. 12/829,089, filed Apr. 29, 2013, 17 pp.
Office Action from U.S. Appl. No. 12/829,089, dated Jan. 28, 2013, 30 pp.
Office Action from U.S. Appl. No. 12/769,149, dated Jul. 12, 2013, 11 pp.

* cited by examiner

PROGRAMMING TECHNIQUES FOR CONTROLLING RATE OF CHANGE OF ELECTRICAL STIMULATION THERAPY

This application claims the benefit of U.S. Provisional Application No. 61/353,842, filed Jun. 11, 2010, and U.S. Provisional Application No. 61/397,419, filed Jun. 11, 2010. The entire content of each of the above applications is incorporated herein by reference.

TECHNICAL FIELD

The disclosure relates to medical devices and, more particularly, to implantable medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. The electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes programming techniques for medical devices that deliver electrical stimulation therapy. The programming techniques may include controlling a transition from an initial stimulation location or initial stimulation shape (referred to collectively throughout as an "initial stimulation zone") to a user-specified target stimulation location or target stimulation shape (referred to collectively throughout as a "target stimulation zone") in order to limit the rate of change of stimulation. The rate of change may be predetermined or user determined. The rate of change may also be used to automatically generate intermediate stimulation zones between the initial and target stimulation zones. In some cases, a transition from an initial stimulation zone may be controlled by a transition control bar that includes a number of indicators which may correspond, for example, to a size of change of a stimulation zone.

In one example, the disclosure is directed to a method that includes receiving, via a programmer for an electrical stimulator, user input indicating a target stimulation zone, and controlling the electrical stimulator to transition electrical stimulation from an initial stimulation zone to the target stimulation zone via one or more intermediate stimulation zones based on the target stimulation zone.

In another example, the disclosure is directed to a system including a user interface configured to receive user input indicating a target stimulation zone and a processor configured to control an electrical stimulator to transition electrical stimulation from an initial stimulation zone to the target stimulation zone via one or more intermediate stimulation zones.

In another example, the disclosure is directed to a system including means for receiving user input indicating a target stimulation zone and means for controlling an electrical stimulator to transition electrical stimulation from an initial stimulation zone to the target stimulation zone via one or more intermediate stimulation zones defined based on the target stimulation zone.

In another example, the disclosure is directed to a computer-readable storage medium including instructions that, when executed, cause at least one processor to receive user input indicating a target stimulation zone and control an electrical stimulator to transition electrical stimulation from an initial stimulation zone to the target stimulation zone via one or more intermediate stimulation zones.

In another example, the disclosure is directed to a device comprising means for receiving user input indicating a target stimulation zone, and means for controlling the electrical stimulator to transition electrical stimulation from an initial stimulation zone to the target stimulation zone via one or more intermediate stimulation zones.

The details of one or more aspects of the disclosure are set forth in the accompanying drawings and the description below. Other features, objects, and advantages will be apparent from the description and drawings, and from the claims.

DETAILED DESCRIPTION

This disclosure describes various techniques for medical devices that deliver electrical stimulation therapy for controlling a transition from an initial stimulation location or initial stimulation shape, which may be referred to as an initial stimulation zone, to a user-specified target stimulation location or target stimulation shape, which may be referred to as a target stimulation zone, in order to limit the rate of change of stimulation. By controlling the electrical stimulator to transition electrical stimulation from an initial stimulation zone to the target stimulation zone via one or more intermediate stimulation zones, the rate of change of stimulation may be limited. In this manner, stimulation amplitude and/or location may transition in a controlled manner, e.g., such that sudden jumps in stimulation amplitude or location may be avoided.

Figure 1:
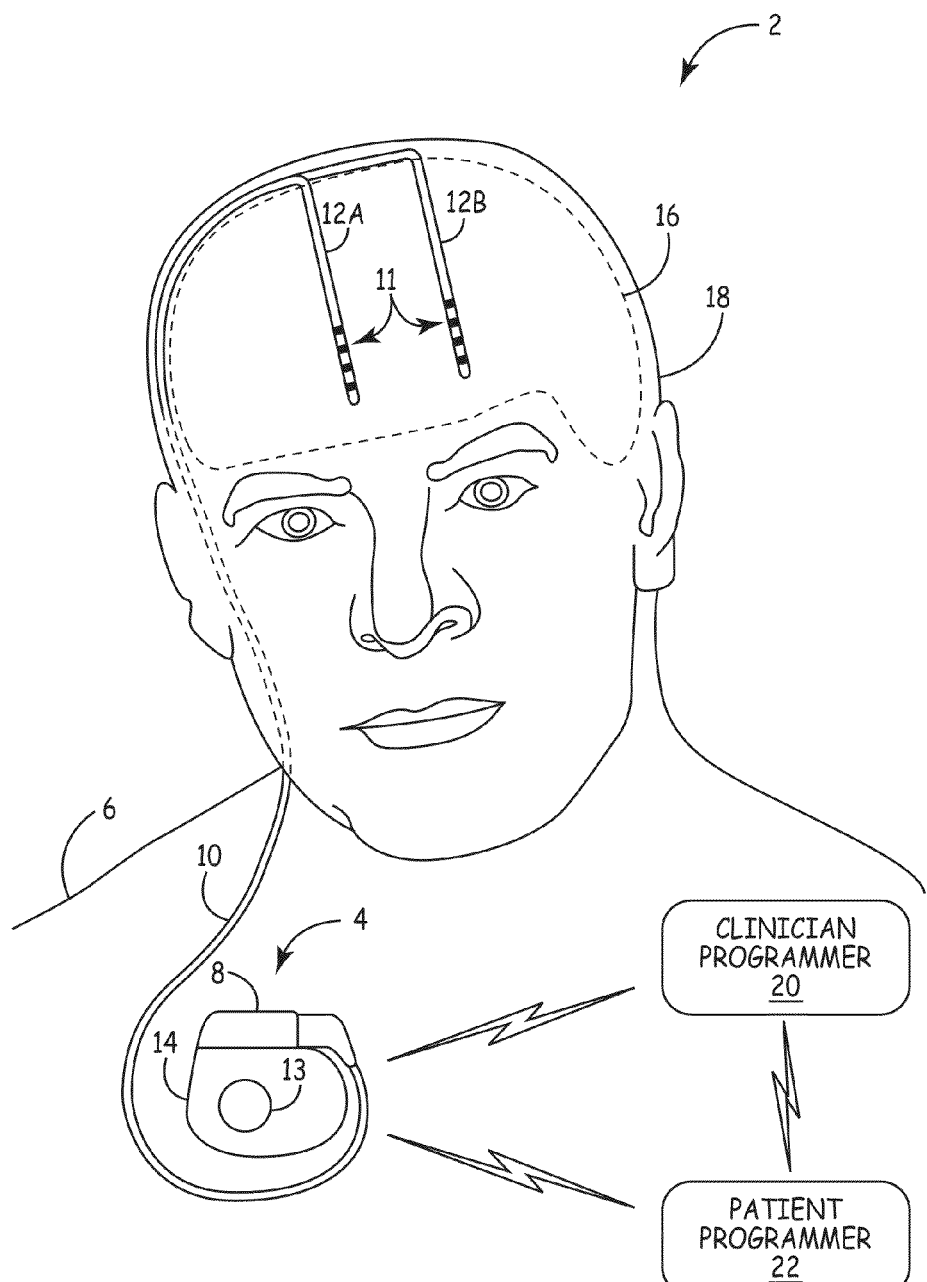
FIG. 1 is a conceptual diagram illustrating an example therapy system that includes an implantable stimulator coupled to a stimulation lead.

FIG. 1 is a conceptual diagram illustrating an example system 2 that may be used to deliver stimulation therapy to patient 6. Patient 6 ordinarily, but not necessarily, will be a human. Generally, therapy system 2 includes implantable stimulator 4 that delivers electrical stimulation to patient 6 via one or more implantable electrodes (not shown). The implantable electrodes may be deployed on one or more implantable medical leads, such as implantable medical lead 10, and in some cases on a can electrode. The electrical stimulation may be in the form of controlled current pulses or voltage pulses, or substantially continuous current or voltage waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. In some example implementations, one or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, e.g., a current or voltage waveform or current or voltage pulses, and delivers the stimulation via an implantable medical lead 10 carrying an array of implantable stimulation electrodes 11. In general, delivery of electrical stimulation using controlled current pulses will be described in this disclosure for purposes of illustration. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of one or more anodes (or cathodes) on a lead that each source (or sink) current and one or more cathodes (or anodes) on the same lead or another lead that sink (or source) current, or the use of one anode on a lead that sources current and multiple cathodes on the same lead or another lead that sink current. A hybrid stimulation arrangement that combines both unipolar and bipolar electrode relationships may be referred to as an omnipolar arrangement. Techniques of this disclosure may be implemented using unipolar arrangements, bipolar/multipolar arrangements, and omnipolar arrangements.

FIG. 1 further depicts a housing, or can, electrode 13. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of housing 14, or multiple portions of housing 14. In one example implementation of the techniques of this disclosure, e.g., an omnipolar arrangement, one or more electrodes 11 may transfer stimulation pulses from the lead 10 to the tissue substantially simultaneously with stimulation pulses delivered via housing electrode 13.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, dystonia, urinary or fecal incontinence, pelvic pain, sexual dysfunction, and gastroparesis. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 or occipital nerves in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width, pulse shape, and pulse rate. Patient 6 may also select a program, e.g., from among a plurality of stored programs, as the present program to control delivery of stimulation by implantable stimulator 4.

In accordance with various techniques described in this disclosure, clinician programmer 20 and/or patient programmer 22 may be used to receive user input indicating a target stimulation zone. Then, the programmer may control an electrical stimulator, e.g., IMD 4, to control the electrical stimulator to transition electrical stimulation from an initial stimulation zone to the target stimulation zone via one or more intermediate stimulation zones, as described in more detail below. A stimulation zone is an area of stimulation defined by one or more electrodes recruited to provide stimulation (or guarding/shielding in the case of anodal zones), their contributions, and an intensity. An electrode's contribution is the degree to which a given electrode delivers its zone's desired intensity. The electrode contribution may have a value between 0.0 and 1.0. A zone's intensity may be the amplitude at which its strongest electrodes deliver therapy. For example, if a zone's amplitude is 10 mA, an electrode within that zone having a contribution of 1.0 would deliver the full 10 mA, an electrode having a contribution of 0.5 would deliver 5 mA, and an electrode of having a contribution of 0.2 would deliver 2 mA. Contribution may alternately have a fractional value, such as a given number of $128^{th}$ parts, e.g., $^{11}/_{128}$, $64^{th}$ parts, e.g., $^{13}/_{64}$, or another fraction of a whole. In one example, a first electrode that sinks (or sources) the most current to produce a given stimulation zone has a first contribution of 1.0, and the contributions of the remaining electrodes used to produce that particular stimulation zone are a percentage of that first contribution. If a second electrode sinks (or sources) the same amount of current as the first electrode, then the first and second electrode have the same contributions, e.g., both may have contributions of 1.0. Zones may be cathodal, e.g., to indicate stimulation delivered via one or more cathodes in associated with the zone, or anodal, e.g., to indicate a guard/shield supported by one or more anodes associated with the zone. Cathodal zones may be graphically represented by a first color, e.g., red, and anodal zones may be graphically represented by a second color, e.g., blue.

As one example, a user may graphically define the target stimulation zone, e.g., on a graphical representation of one or more implantable leads. In some examples, a user may graphically define the target stimulation zone by graphically manipulating a shape or size of an initial stimulation zone in order to define the target stimulation zone. In other examples, a user may graphically define the target stimulation zone by graphically manipulating a location of the initial stimulation zone in order to define the target stimulation zone. In response, the clinician programmer 20 and/or patient programmer 22 controls the electrical stimulator to transition electrical stimulation from the initial stimulation zone to the target stimulation zone via one or more intermediate stimulation zones.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current or voltage waveforms or constant current or voltage pulses. The shapes of the pulses may vary according to different design objectives, and may include ramped or trapezoidal pulses, sinusoidal or otherwise curved pulses, stepped pulses having 2 or more discrete amplitudes, closely spaced pairs of pulses, and biphasic (positive and negative aspects within a single pulse) or monophasic (only positive or only negative aspects within a single pulse) variations of any of the above. In the case of current-based stimulation, implantable stimulator 4 regulates current that is sourced or sunk by one or more electrodes, referred to as regulated electrodes. In some examples, one or more of the electrodes may be unregulated. In such configurations, the housing electrode and/or a lead electrode may be the unregulated electrode.

A source current may refer to a positive current that flows out of an electrode (anode), e.g., from a regulated current source via a regulated current path to surrounding tissue, or from a reference voltage via an unregulated current path. A sink current may refer to a negative current that flows into an electrode (cathode), e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current in the case of partial cancellation. In some examples, an unregulated current path can source or sink current approximately equal to this net difference. In other examples, regulated source and sink currents may be substantially balanced.

As mentioned above, in some example implementations, e.g., an omnipolar arrangement, one or more electrodes 11 may transfer stimulation current from the lead 10 to the tissue substantially simultaneously with stimulation current delivered to tissue from housing electrode 13. For example, housing electrode 13 and one or more electrodes 11 may be configured to act as anodes and source current. Substantially simultaneously delivering stimulation via both a housing anode and one or more lead anodes may allow a user to achieve different electric field shapes by controlling current paths between the housing anode and the lead anode(s) in a relative manner. In other example implementations, e.g., a bipolar/multipolar arrangement, one or more electrodes 11 may be configured to act as anodes and source current while one or more different electrodes 11 may be configured to act as cathodes and sink current. In another example implementation, e.g., a unipolar arrangement, housing electrode 13 may be configured to act as an anode and source current while one or more electrodes 11 on one or more leads are configured to act as cathodes and sink current. Techniques of this disclosure may be implemented using unipolar arrangements, bipolar/multipolar arrangements, and omnipolar arrangements.

Figure 2:
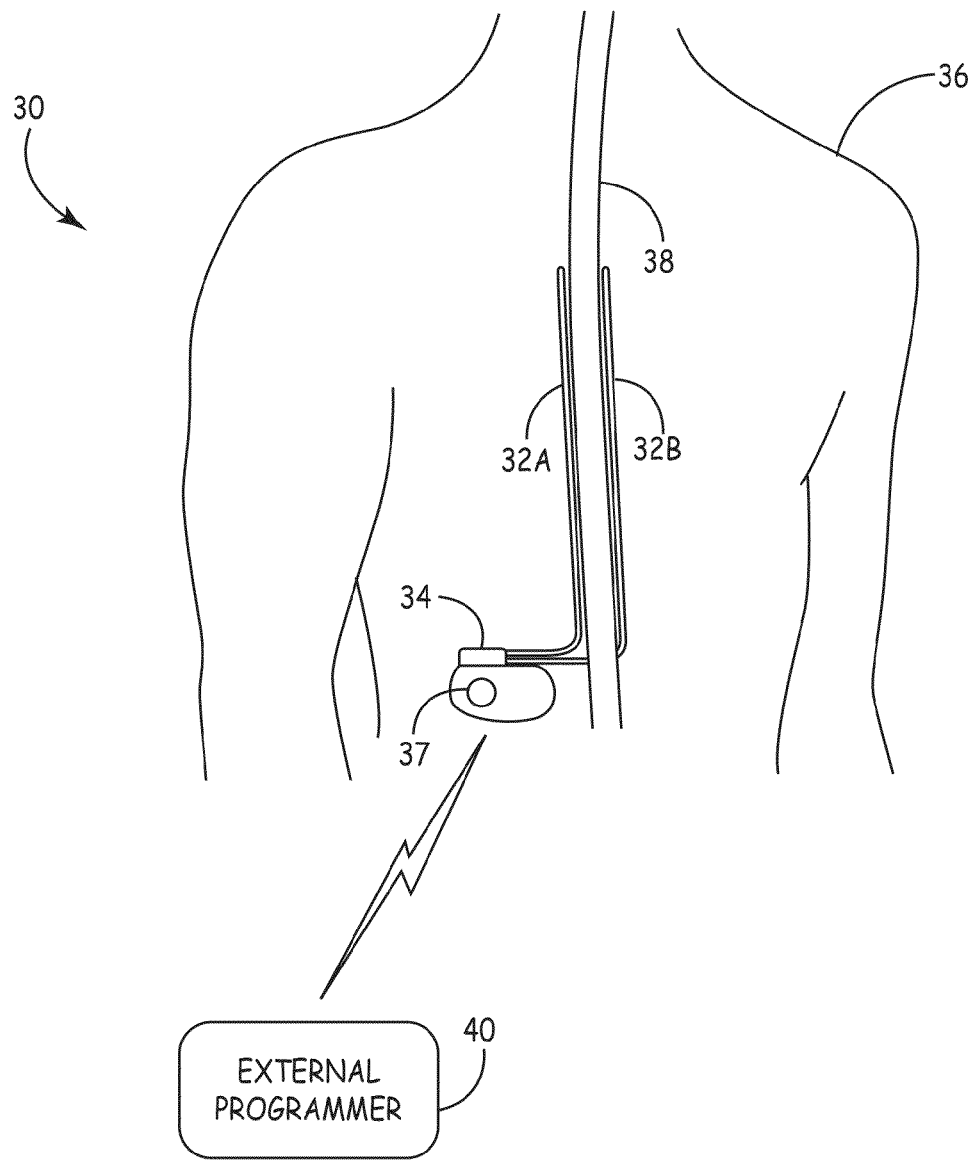
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated, stimulation electrodes. Alternatively, implantable stimulator 34 may be configured to deliver constant voltage pulses. As additional control means, the implantable stimulator 34 may be configured to deliver constant power pulses or pulses with a controlled amount of total charge movement in Coulombs. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. In an omnipolar arrangement, for example, at the distal ends of leads 32 are one or more electrodes (not shown) that transfer the stimulation pulses from the lead to the tissue substantially simultaneously with stimulation pulses delivered via a housing electrode, e.g., electrode 37. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

As used in one example implementation of the techniques of this disclosure, e.g., an omnipolar arrangement, substantially simultaneous delivery of stimulation, whether current or voltage or power or charge, refers to the partial or complete time-wise synchronization of the electrical stimulation pulses or waveforms. Complete time-wise synchronization may refer to the housing electrode, e.g., anode, delivering stimulation at the same time that one or more lead electrodes, e.g., anodes, deliver stimulation. For example, complete time-wise synchronization may include the rising edge of the stimulation pulse or waveform being delivered by the housing electrode, e.g., anode, substantially coinciding with the rising edge of the stimulation pulse or waveform being delivered by the one or more lead electrodes, e.g., anodes, and the falling edge of the stimulation pulse or waveform being delivered by the housing electrode, e.g., anode, coinciding with the falling edge of the stimulation pulse or waveform being delivered by the one or more lead electrodes, e.g., anodes. Complete time-wise synchronization may also include a pulse delivered by a housing anode, for example, being delivered within the pulse width of a pulse delivered by a lead anode, for example. Partial time-wise synchronization may refer to the housing electrode, e.g., anode, delivering one electrical stimulation pulse or waveform while at least one lead electrode, e.g., anode, is delivering another electrical stimulation pulse or waveform such that at least a portion of one of the rising or falling edge of one pulse or waveform overlaps in time with at least a portion of one of the rising or falling edge of at least one other pulse or waveform.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry.

In accordance with various techniques described in this disclosure, programming of stimulator 34 may include receiving, via programmer 40, user input indicating a target stimulation zone and controlling the electrical stimulator to transition electrical stimulation from an initial stimulation zone to the target stimulation zone via a sequence of one or more intermediate stimulation zones. By controlling the electrical stimulator to transition electrical stimulation from an initial stimulation zone to the target stimulation zone via one or more intermediate stimulation zones, the rate of change of stimulation between successive stimulation zones in the sequence may be limited. In this manner, in some examples, sudden jumps in stimulation amplitude or location may be avoided, which may be uncomfortable or disconcerting to a patient receiving stimulation therapy, or which may not allow a patient sufficient time to evaluate perceived efficacy and provide a clinician with feedback regarding the stimulation settings.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 4 or any other computing device via wireless communication. Programmer 40, for example, may communicate via wireless communication with implantable stimulator 4 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
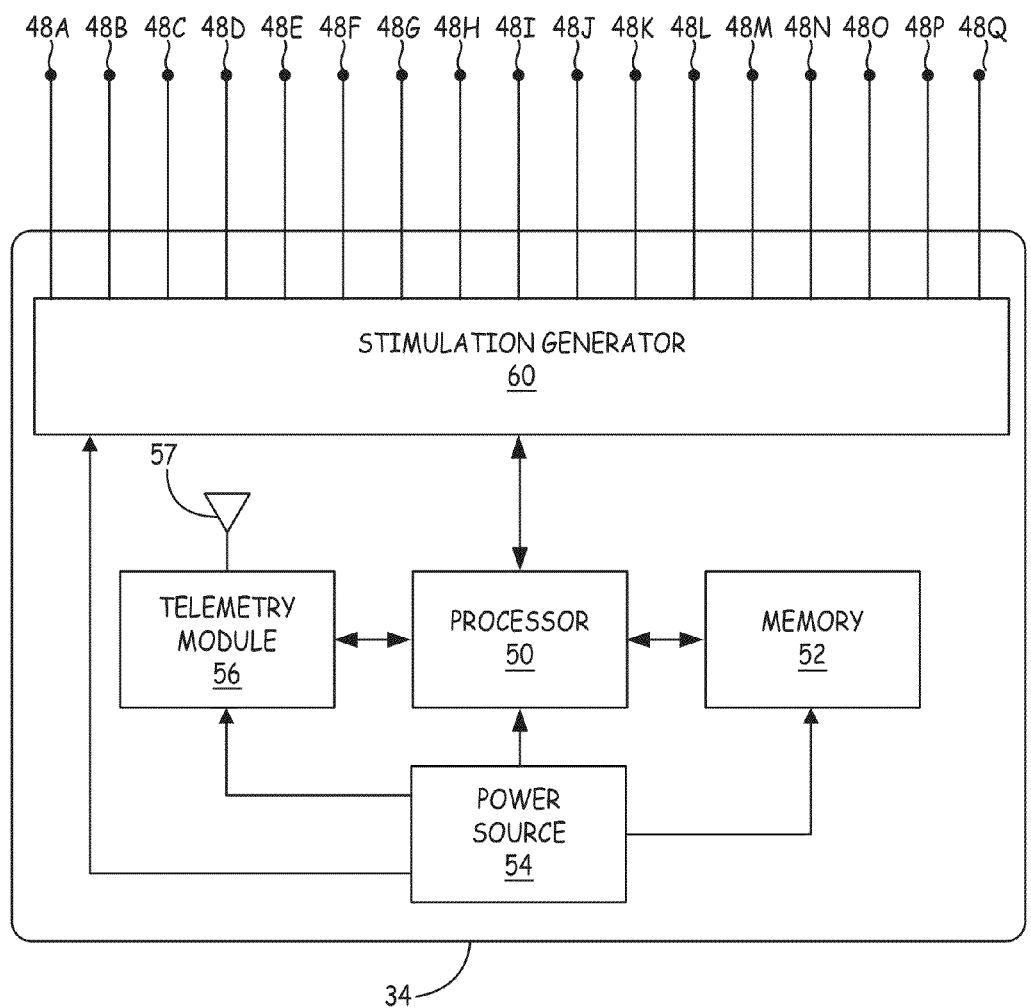
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, and a stimulation generator 60. Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide a 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Different electrodes are selected to form electrode combinations. Polarities are assigned to the selected electrodes to designate the electrodes as anodes or cathodes and form electrode configurations.

Electrode 48Q represents one or more electrodes that may be carried on a housing, i.e., can, of implantable stimulator 4. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing, such as adjacent to a lead connection header 8 of the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry module 56, and power source 54.

Housing electrode 48Q may be configured for use as an anode to source current substantially simultaneously with one or more electrodes 48A-48P configured for use as cathodes sinking current in a unipolar arrangement. Housing electrode 48Q may be configured for use as an anode to source current substantially simultaneously with current sourced by another electrode 48A-48P configured for use as an anode in an omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the IMD, e.g., electrode 48Q, at least one anode on a lead, electrode 48A, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). Housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

In one example implementation, e.g., an omnipolar arrangement, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing. In some examples, the electrode combination may include one or more anodes on one or more leads, and one or more cathodes on the same lead or a different lead, e.g., a bipolar/multipolar arrangement. In other examples, the electrode combination may include an anode on the housing, and one or more cathodes on one or more leads, e.g., omnipolar arrangement. In yet another example, the electrode combination may include a cathode on the housing, and one or more additional cathodes on one or more leads, along with one or more anodes also on the leads, e.g., a variation of an omnipolar arrangement.

Telemetry module 56 may include a radio frequency (RF) transceiver to permit bidirectional communication between implantable stimulator 4 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to implementations in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 4. In some embodiments, power requirements may be small enough to allow stimulator 4 to utilize patient motion at least in part and implement a kinetic energy-scavenging device to trickle charge a rechargeable battery. A voltage regulator may generate one or more regulated voltages using the battery power.

Figure 4:
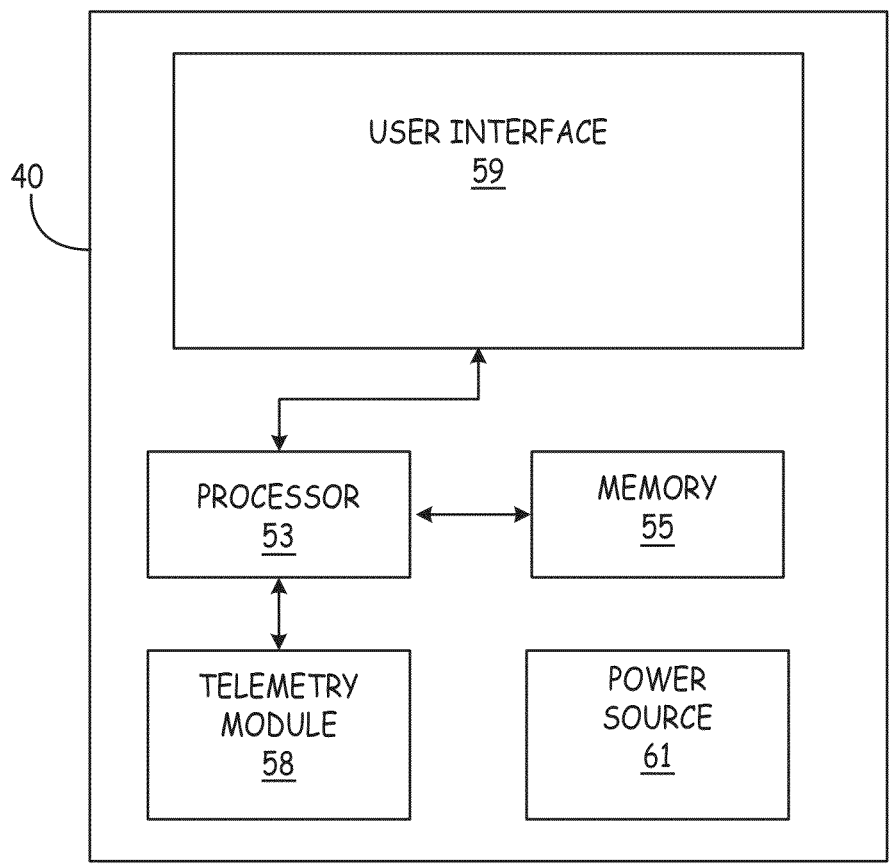
FIG. 4 is a block diagram illustrating various example components of an external programmer for use with an electrical stimulator.

FIG. 4 is a functional block diagram illustrating various components of an external programmer 40 for an implantable stimulator 14. Although the components shown in FIG. 4 are described in reference to external programmer 40, the components may also be included within clinician programmer 20 or patient programmer 22 shown in FIG. 1. As shown in FIG.

4, external programmer 40 includes processor 53, memory 55, telemetry module 58, user interface 59, and power source 61. In general, processor 53 controls user interface 59, stores and retrieves data to and from memory 55, and controls transmission of data with implantable stimulator 34 through telemetry module 58. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Using various techniques of this disclosure, a clinician or patient 36 may input a target stimulation zone on or adjacent to one or more leads using interface 59. In particular, user interface 59 may be used for graphically representing an initial stimulation zone and receiving input from a user that indicates a target stimulation zone, as will be described in more detail below. For example, a clinician or patient 36 may graphically define the target stimulation zone, e.g., on a graphical representation of one or more implantable leads. In some examples, a user may graphically define the target stimulation zone by graphically manipulating a shape of the initial stimulation zone in order to define the target stimulation zone. In other examples, a user may graphically define the target stimulation zone by graphically manipulating a location of the initial stimulation zone in order to define the target stimulation zone. In other examples, the initial stimulation zone may be pre-defined as a starting point for a user. In response, the programmer 40 controls the electrical stimulator to transition electrical stimulation from the initial stimulation zone to the target stimulation zone via a sequence of one or more intermediate stimulation zones. In other examples, stimulator 34, or a combination of programmer 40 and stimulator 34, may control the transition from the initial stimulation zone to the target stimulation zone. In this manner, the rate of change of stimulation delivered to a patient may be limited in order to reduce or eliminate any discomfort that the patient may sense during the transition, and allow a patient to evaluate the efficacy of stimulation and provide feedback to a clinician.

Telemetry module 58 allows the transfer of data to and from stimulator 34. Telemetry module 58 may communicate automatically with stimulator 34 at a scheduled time or when the telemetry module detects the proximity of the stimulator. Alternatively, telemetry module 58 may communicate with stimulator 34 when signaled by a user through user interface 59. To support RF communication, telemetry module 44 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 44 which may be coupled to an internal antenna or an external antenna. Telemetry module 44 may be similar to telemetry module 58 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 46 delivers operating power to the components of programmer 40. Power source 46 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
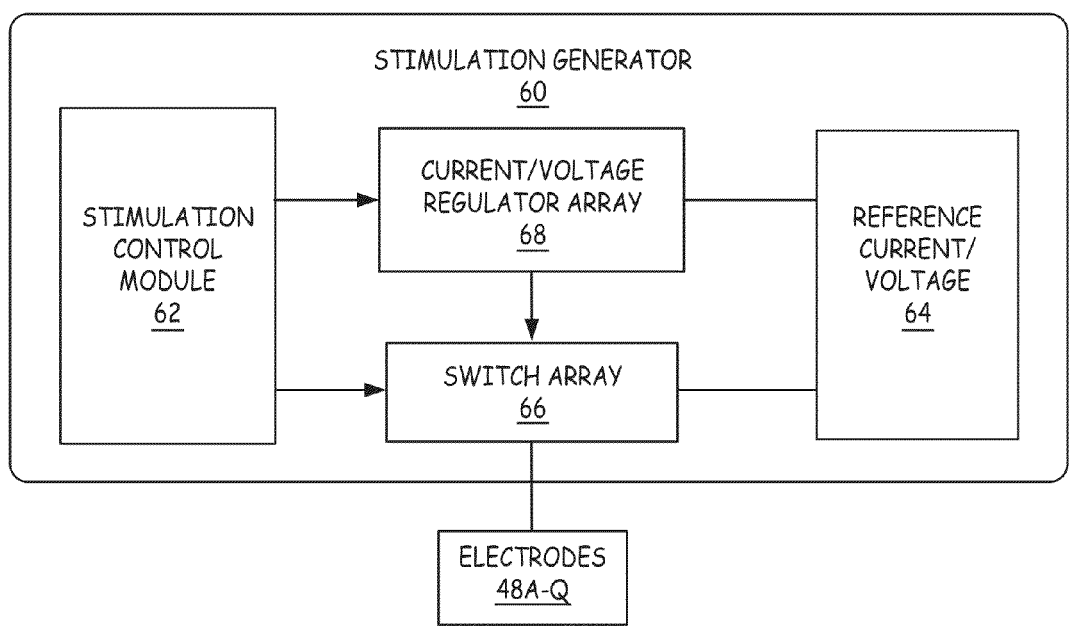
FIG. 5 is a block diagram illustrating various components of an example electrical stimulation generator for use in the implantable electrical stimulator of FIG. 3.

FIG. 5 is a block diagram illustrating various components of an example stimulation generator 60. Stimulation generator 60 may be used with an implantable stimulator, e.g., to perform the functions of stimulation generator 60 as described with reference to FIGS. 1-3. Although described with respect to implantable stimulator 4, stimulation generator 60 may also be used for implantable stimulator 34, or other types of stimulators. In the example of FIG. 5, stimulation generator 60 is selectively, e.g., based on a signal from processor 50 (FIG. 3), configured to deliver constant current stimulation pulses to patient 6 via various electrode combinations. However, the disclosure is not limited to examples in which regulated current pulses are delivered. In other examples, stimulation generator 60 may provide continuous, regulated current waveforms, rather than regulated current pulses. In still other examples, stimulation generator 60 may deliver combinations of continuous waveforms and pulses, or selectively deliver either continuous waveforms or pulses. Stimulation generator 60 may generate either constant current-based or constant voltage-based stimulation in the form of pulses or continuous waveforms. It may also be controlled to provide constant power (current-voltage product) or controlled charge stimulation pulses. Additionally, it may be configurable to deliver any of these variously controlled pulse amplitudes in a variety of pulse shapes (trapezoidal or ramped, sinusoidal or otherwise curved, or stepped).

In the example illustrated in FIG. 5, stimulation generator 60 includes stimulation control module 62, reference current/voltage source 64, switch array 66, and current/voltage regulator array 68. Reference current/voltage source 64 may provide operating power to current/voltage regulator array 68, and may include a regulated voltage that sets the level of the reference voltage. As shown in FIG. 5, reference current/ voltage source 64 may be coupled to provide operating power for the current/voltage regulator array 68 and provide a reference voltage, or reference current when appropriate, for connection to electrodes 48A-48Q for an unregulated mode of electrode operation. In other examples, however, the voltage level of the reference voltage and the operating voltage level provided to regulate current source array 68 may be different.

Stimulation control module 62 forms a stimulation controller that controls switch array 66 and current/voltage regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an implantable stimulator 4 or 34 for use by stimulation control module 62.

Current/voltage regulator array 68 includes a plurality of regulated current sources or sinks. Again, a current regulator may function as either a current source or sink, or be selectively configured to operate as either a source or a sink. Alternatively, current/voltage regulator array 68 may regulate voltage instead of, or in addition to, current. For convenience, however, the term "current regulator" may be used in some instances to refer to either a source or sink. Hence, each of the current regulators in current/voltage regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

In this example, each switch of switch array 66 may couple a corresponding one of electrodes 48 to either a corresponding bidirectional current regulator of current/voltage regulator array 68 or to reference current/voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current/voltage regulator array 68. In other examples, stimulation control module 62 may selectively open and close switches in switch array 66 to configure either the housing electrode, e.g., electrode 48Q, or an electrode on the lead as an unregulated electrode by connection to reference current/voltage 64. In addition, stimulation control module 62 may selectively control individual regulated current sources or sinks in current/voltage regulator array 68 to deliver stimulation current pulses to the selected electrodes.

Reference current/voltage 64 may be a high or low voltage supplied by a regulated power source, depending on whether an electrode is programmed to be an unregulated source (high voltage rail) or unregulated sink (low voltage rail). Hence, reference current/voltage 64 may produce high and low reference voltages, or reference currents when appropriate, for selective coupling to unregulated, reference electrodes as needed given the selected electrode configuration. A regulated power source may produce one or more regulated voltage levels for use as reference current/voltage 64 and for use as a power rail for current/voltage regulator array 68. Again, although the same reference current/voltage 64 is coupled to current/voltage regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference current/voltage 64. As previously described, in some examples, two or more regulated, stimulation electrodes 48 may be intentionally programmed to deliver different amounts of current such that the regulated electrodes produce an unbalanced current distribution. In other examples, regulated source and sink current may be balanced such that substantially all current may be sourced and sunk via respective regulated current sources and sinks.

To provide individual control of electrodes 48 as either regulated electrodes or as unregulated, reference electrodes, stimulation control module 62 controls operation of switch array 66, and current/voltage regulator array 68. When stimulation is delivered to patient 6, for the example of current pulses, stimulation control module 62 controls switch array 66 to couple selected stimulation electrodes for a desired electrode combination to respective current regulators of current/voltage regulator array 68 or to reference current/voltage 64, as needed. Stimulation control module 62 controls the regulated bidirectional current sources of current/voltage regulator array 68 coupled to regulated electrodes to source or sink specified amounts of current. For example, stimulation control module 62 may control selected current sources or sinks on a pulse-by-pulse basis to deliver current pulses to corresponding electrodes.

Stimulation control module 62 also deactivates the regulated bidirectional current regulators of current/voltage regulator array 68 tied to inactive electrodes, i.e., electrodes that are not active as regulated electrodes in a given electrode configuration. Each regulated bidirectional current regulator of current/voltage regulator array 68 may include an internal enable switch controlled by stimulation control module 62 that disconnects regulated power source 64 from the current regulator or otherwise disables the current source when the corresponding electrode is not used as a regulated electrode to deliver stimulation.

As mentioned above, this disclosure describes various techniques for medical devices that deliver electrical stimulation therapy for controlling a transition from an initial stimulation location or initial stimulation shape to a user-specified target stimulation location or target stimulation shape in order to limit the rate of change of stimulation. Limiting the rate of change of stimulation may reduce or eliminate discomfort felt by patients receiving electrical stimulation therapy. For example, as described in more detail below, a user may input an indication of a target stimulation zone, e.g., via a programmer for an electrical stimulator. Then, by controlling the electrical stimulator to transition electrical stimulation from an initial stimulation zone to the target stimulation zone via one or more intermediate stimulation zones, the rate of change of stimulation may be limited. In this manner, sudden jumps in stimulation amplitude or location are avoided, which may be uncomfortable or disconcerting to a patient receiving stimulation therapy.

Figure 6:
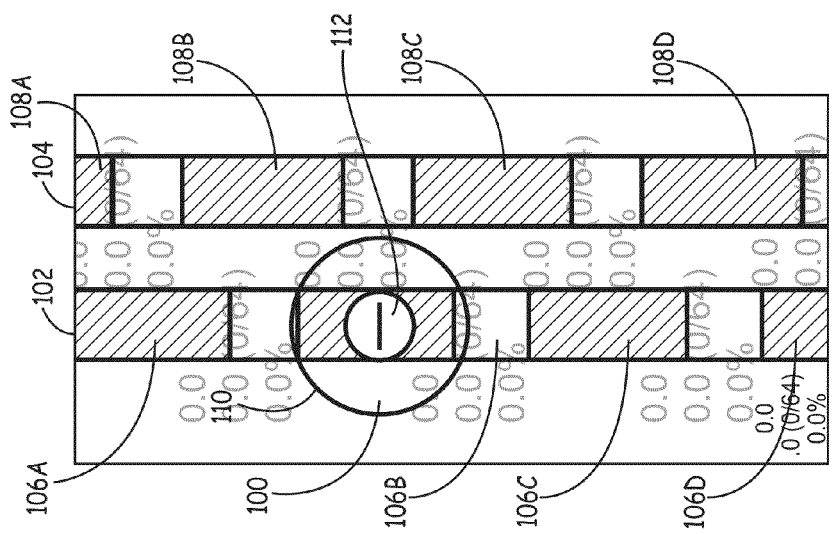
FIG. 6 is a conceptual diagram illustrating an example initial stimulation zone displayed in conjunction with a graphical representation of a portion of two implantable leads.

FIG. 6 is a conceptual diagram illustrating an example initial stimulation zone displayed in conjunction with a graphical representation of a portion of two implantable leads. In particular, FIG. 6 graphically depicts, e.g., on a display screen of user interface 59 of programmer 40, an initial stimulation zone 100 along with a representation of a portion of first implantable lead 102 and a portion of second implantable lead 104. In some examples, leads 102 and 104 may correspond to leads 12A and 12B in FIG. 1 or leads 32A and 32B in FIG. 2. Lead 102 includes four electrodes (or a portion of four electrodes), namely electrodes 106A-106D (referred to collectively as "electrodes 106") and lead 104 includes four electrodes (or a portion of four electrodes), namely electrodes 108A-108D (referred to collectively as "electrodes 108"). As indicated above, leads 102, 104 may have more, or fewer, electrodes, depending on the particular lead configuration in use. However, for ease of illustration, only four electrodes (or a portion of four electrodes) have been depicted on each of leads 102, 104.

Again, a stimulation zone, e.g., initial stimulation zone 100, is an area of stimulation defined by one or more electrodes recruited to provide stimulation (or guarding/shielding in the case of anodal zones), their contributions, and an intensity. A processor, e.g., processor 53, defines, or "recruits," a set of electrodes to generate the stimulation zone. An electrode's contribution is the degree to which a given electrode delivers its zone's desired intensity. The electrode contribution may have a value between 0.0 and 1.0. Zones may be cathodal, e.g., for stimulation, or anodal, e.g., for shielding/guarding. In operation, electrodes in anodal and cathodal zones may work together to define the overall electrical stimulation that is delivered via the lead or leads implanted in the patient. In FIG. 6, initial stimulation zone 100 is defined by a single electrode, namely electrode 106B, recruited to provide stimulation to patient 6. A user may have created initial stimulation zone 100 using programmer 40. For example, a user may have used a stylus, pointing media, the display itself in the case of a touchscreen display, the display in conjunction with a point media, or some other input mechanism, to define initial stimulation zone 100. Stimulation zone 100 may be referred to as the "initial" stimulation zone because it is the shape of the stimulation zone prior to the user stretching, shrinking, or otherwise manipulating the stimulation zone.

A stimulation zone, e.g., initial stimulation zone 100, may be graphically defined by an outline, shown at 110. Outline 110 may be referred to as the control shape of the stimulation zone. The control shape is the theoretical extent of the stimulation and may be stretched, shrunk, or otherwise manipulated by a user when IMD 4 is delivering stimulation or when IMD 4 is not delivering stimulation, thereby allowing a user to manipulate an actual or hypothetical stimulation zone. Using the techniques of this disclosure, programmer 40 may control IMD 4 to transition between the initial control shape and the target control shape or the initial stimulation zone and the target stimulation zone. It should be noted that, in some instances, this disclosure may use the terms "control shape" and "stimulation zone" interchangeably.

Stimulation zone 100 may be depicted by a color, e.g., green, and outline 110, also referred to as control shape 110, may be depicted by another color, e.g., yellow. In some examples, the control shape 110 of initial stimulation zone 100 may be a solid line or a dashed line or dotted line, as will be described in more detail below. For example, a solid control shape 110 may indicate the target stimulation that will be delivered upon completion of the transition and a dashed line or dotted line may indicate the actual stimulation current being delivered. In some examples, icon 112 may be included. Icon 112 may indicate whether stimulation zone 100 is cathodal or anodal. In FIG. 6, icon 112 is shown as a "minus" sign circumscribed by a circle, indicating that stimulation zone 100 is a cathodal zone. In other examples, icon 112 may be shown as a "plus" sign circumscribed by a circle, indicating that a zone is an anodal guard or shield. The circle of icon 112 indicates the centroid of a stimulation zone, e.g., initial stimulation zone 100, and may move based on a user's manipulation of the initial stimulation zone.

Figure 7:
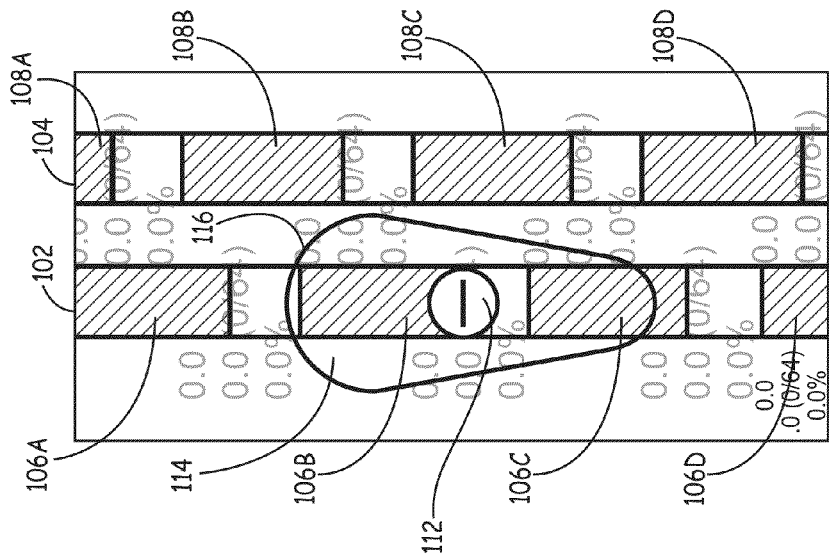
FIG. 7 is a conceptual diagram illustrating the stimulation zone of FIG. 6 following a single stretch input.

FIG. 7 is a conceptual diagram illustrating the stimulation zone of FIG. 6 following a single stretch input. In particular, FIG. 7 depicts target stimulation zone 114 with control shape 116 created following a single stretch of initial stimulation zone 100 of FIG. 6. For example, a user may use a pointing media such as a stylus, finger, or the like and stretch the graphical representation of initial stimulation zone 100 on user interface 59 of programmer 40 "downward" from electrode 106B toward electrode 106C. Of course, other input mechanisms to programmer 40 may also be used, including a keypad, a mouse, a tracking ball, or the like. The examples presented throughout this disclosure are not limited to inputting information to programmer 40 via a display, e.g., a touchscreen.

As seen in FIG. 7, in response to the user's input, e.g., a stretch, programmer 40 has recruited a second electrode, namely electrode 106C, in order to provide the stimulation that may be required to generate target stimulation zone 114. Following the stretch, target stimulation zone 114 is larger than initial stimulation zone 100 and defined by two electrodes, namely newly recruited electrode 106C as well as the original electrode 106B, both of which are on lead 102. As will be described in more detail below, the contribution of electrode 106C to target stimulation zone 114 is less than the contribution of electrode 106B as seen graphically by electrode 106B being enveloped by target stimulation zone 114 and electrode 106C being partially covered by target stimulation zone 114. The relative contributions of each electrode in target stimulation zone 114 may also be indicated by the radius or corner of the control shape around each electrode. Electrodes with smaller contributions may also have smaller radii or "sharper" corners of the stimulation zone. In other words, target stimulation zone 114 may be displayed as a convex hull around the outermost edge of "circles" around each electrode. As seen in FIG. 7, the centroid of target stimulation zone 114, indicated by icon 112, has shifted from its initial location in FIG. 6 due to the stretch.

It should be noted that the initial stimulation zone and target stimulation zone do not necessarily represent the electrical current field produced by the electrodes in the zone, but rather serve as a representation to convey relative amounts of current borne by particular electrodes that define a stimulation zone.

Figure 8:
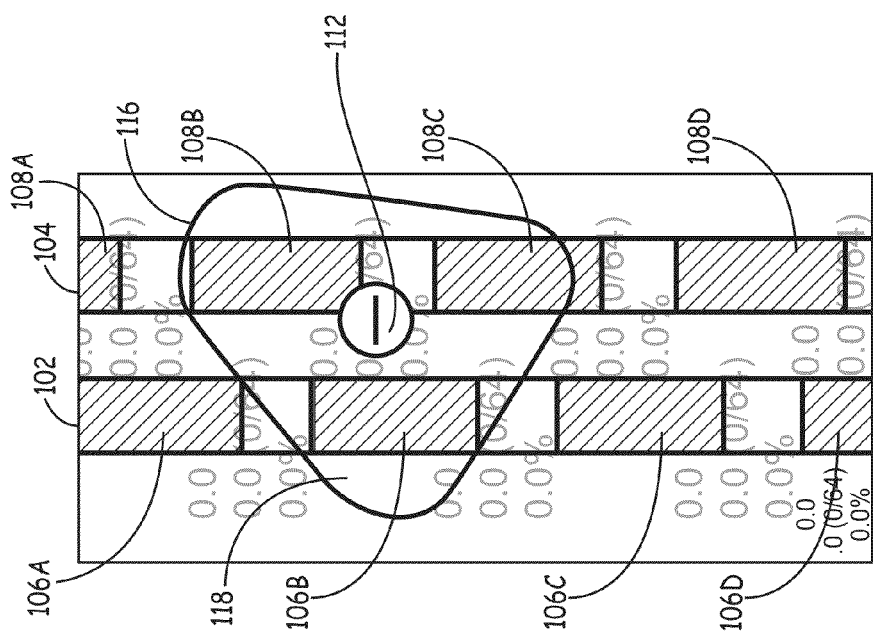
FIG. 8 is a conceptual diagram illustrating the stimulation zone of FIG. 6 following two stretch inputs.

FIG. 8 is a conceptual diagram illustrating the stimulation zone of FIG. 6 following two stretch inputs. Programmer 40 permits multiple manipulations, both in the case of multiple stretches, multiple shrinks, or a combination of stretches and shrinks or the like. FIG. 8 depicts target stimulation zone 118 with control shape 120 created following two stretches of initial stimulation zone 100 of FIG. 6. For example, a user may use a pointing media such as a stylus, finger, or the like and stretch the graphical representation of initial stimulation zone 100 on user interface 59 of programmer 40 "upward" to the right from electrode 106B toward electrode 108B on lead 104 and "downward" to the right from electrode 106B toward electrode 108C on lead 104. The stimulation zone may show specific control points to facilitate interaction, such as stretching and shrinking. These may include an exaggerated border for stretching, a "handle" that a user may "grasp" in order to stretch or shrink the zone, or specific boxes or dots at the corners to allow resizing.

As seen in FIG. 8, in response to the user's input, e.g., two stretches, programmer 40 has recruited a second electrode, namely electrode 108B on lead 104, and a third electrode, namely electrode 108C on lead 104, in order to provide the stimulation that may be required to generate target stimulation zone 118. Following the stretches, target stimulation zone 118 is larger than initial stimulation zone 100 and defined by three electrodes, namely newly recruited electrodes 108B, 108C as well as the original electrode 106B. As indicated above, programmer 40 and, in particular, processor 53, determines that electrodes 108B, 108C from lead 104 should be recruited to generate target stimulation zone 118. As will be described in more detail below, the contribution of electrode 108C to target stimulation zone 118 is less than the contributions of electrodes 106B and 108B as seen graphically by electrode 106B and electrode 108B being enveloped by target stimulation zone 118 and electrode 108C being partially covered by target stimulation zone 118. The centroid of target stimulation zone 114, indicated by icon 112, has shifted from its initial location in FIG. 6 due to the stretches.

In some example implementations, programmer 40 may impose a limit on stretches, shrinks, or other manipulations such that at least one electrode present in the initial control shape shall be active in the target control shape. This may prevent the user from making multiple manipulations such that the target control shape ends up in a completely different location on the lead array than the initial control shape. Programmer 40 may block any stretch/shrink that would break this rule.

As shown in FIG. 8, an electrode (e.g., electrode 108C) may be partially recruited such that the contribution of the partially recruited electrode to target stimulation zone 118 is less than the contributions of other electrodes to the target stimulation zone. In this manner, an electrode may have a contribution to the target stimulation zone according to the portion of the electrode covered by the control shape. The user may manipulate the control shape to achieve the desired contribution from each electrode. The portion of each electrode that is capable of being covered, or the corresponding contribution of each electrode, may be set to a predetermined number of fractions or segments. As examples, each electrode may be recruited in very small increments, e.g., in tenth, quarter, or even half recruitment.

Alternatively, each electrode may only be recruited entirely as a part of the control shape of target stimulation zone 118. In one example, the user may need to cover the entire electrode with the control shape before that electrode is recruited to contribute to target stimulation zone 118. In another example, the user may only need to cover a portion of the electrode before the control shape automatically extends to cover and recruit the entire electrode as a part of the target stimulation zone. This extension may be a "snap" or "jump" in the size of the control shape to automatically recruit the full electrode based on the portion of the electrode covered by the user. Rules may be implemented that define a coverage threshold for what amount of electrode coverage is required before the electrode is fully recruited. For example, once the user covers 20 percent of the electrode with the control shape, the entire electrode may be recruited during this stretch action. Once the user covers less than 20 percent of the electrode with the control shape, the electrode would no longer be recruited, or abandoned, during a shrink action that eliminates the electrode from the stimulation zone or control shape.

The coverage threshold may generally be between approximately 1 percent coverage and 100 percent coverage. More specifically, the coverage threshold may be between approximately 10 percent and 50 percent coverage. Even though the electrode may not be shown as partially recruited, an electrode shown as entirely recruited may still have a contribution less than other electrodes. Each electrode may be associated with a contribution indicator that indicates the proportion of current or voltage, or the amplitude of current or voltage, contributed by each electrode of the target stimulation zone. Accordingly, the user may adjust the contribution of each recruited electrode shown under the target stimulation zone. In some examples, a recruited electrode with a smaller contribution to the target stimulation zone may have a smaller radius that defines the control shape than other electrodes with a larger contribution.

As indicated above, after a user has manipulated a stimulation zone, e.g., initial stimulation zone 100 of FIG. 6, to create a target stimulation zone, e.g., target stimulation zone 118, the contributions of the electrodes recruited to produce the target stimulation zone may be different from one another. For example, in FIG. 8, as described above, the contribution of electrode 108C to target stimulation zone 118 is less than the contributions of electrodes 106B and 108B. Using one technique of this disclosure, a user may select a "balance" input on user interface 59 of programmer 40, for example. In response, processor 53 may balance the contributions of two or more of the recruited electrodes. That is, processor 53 may set the contributions of the two or more electrodes that were selected to be balanced to be substantially equal to one another. Allowing a user to balance the contributions in this manner may allow the user to reset the contributions of the electrodes to a common state without requiring the user to manipulate the target stimulation zone manually. It may also allow a more capable device to emulate a less capable device, in this case one in which fractional contributions are not achievable by the stimulating hardware.

In one example, processor 53 may balance the recruited anodes and cathodes such that, after balancing, each anode has the same contribution as any other anode and each cathode has the same contribution as any other cathode. For instance, assume that two cathodes were recruited to produce a stimulation zone and that one of the cathodes sinks 70% of the current and the other cathode sinks the remaining 30% of the current. After selecting to "balance" the two cathodes via an input on user interface 59, e.g., tapping via a finger or pointing media, processor 53 modifies the stimulation such that each cathode contributes (sinks) 50% of the current, regardless of their original contribution. If there were three cathodes recruited instead of two, the three cathodes would contribute 33%, 33%, and 34% of the current after a user has selected to balance the electrodes.

In some example implementations, programmer 40 may display a window, e.g., a pop-up window, on user interface 59 after a user has selected to balance two or more recruited electrodes. The window allows a user to choose between several balancing options. For instance, a user may choose to balance only the anodes that have been recruited. For example, if three anodes and three cathodes were recruited, a user may choose to only balance the contributions of the three anodes. Or, the user may choose to balance only the cathodes that have been recruited. For example, if three anodes and three cathodes were recruited, a user may choose to only balance the contributions of the three cathodes. Or, the user may choose to balance only some of the cathodes that have been recruited. For example, if three anodes and five cathodes were recruited, a user may choose to only balance the contributions of the three of the five cathodes.

In addition, a user may choose to balance one or more recruited anodes relative to one or more recruited cathodes so that the selected electrodes work in tandem. By way of specific example, processor 53 may have recruited two anodes to generate an anodal guard/shield and two cathodes to generate a cathodal stimulation zone. Assume that a first anode of the two recruited anodes is sourcing 70% of the current, a second anode of the two recruited anodes is sourcing the remaining 30% of the current, a first cathode of the two recruited cathodes is sinking 70% of the current, and a second cathode of the two recruited cathodes is sinking the remaining 30% of the current. After receiving user input that selects to balance electrodes, programmer 40 displays options that allow a user to select, for example, one (or more) of the two anodes of the anodal guard/shield to balance relative to one or more of the two recruited cathodes. Assuming that a user selects one anode and one cathode to balance relative to one another, then the selected anode and the selected cathode would each contribute 50% of the current after balancing, with the remaining current being distributed amongst the remaining unselected recruited anodes and cathodes.

In one example implementation, after a user has selected to balance two or more electrodes via a balance input on user interface 59 of programmer 40, a user may select an option displayed in the window that allows a user to set the percentage of contribution of the electrodes that were selected to be balanced. For example, assume that a first anode of two recruited anodes is sourcing 70% of the current, a second anode of the two recruited anodes is sourcing the remaining 30% of the current, a first cathode of two recruited cathodes is sinking 70% of the current, and a second cathode of the two recruited cathodes is sinking the remaining 30% of the current. After selecting to balance electrodes, the user may choose to set one anode and one cathode to balance relative to one another, but specify that the selected anode and the selected cathode each contribute 40%, for example, of the current after balancing, with the remaining current being distributed amongst the remaining unselected recruited anodes and cathodes. So, in some examples, if two electrodes are selected for balancing, the user may specify that the two electrodes contribute a percentage of current greater than or less than 50%.

In some example implementations, the shape of the target stimulation zone may change after a user selects to balance the contributions of two or more electrodes. For example, referring to FIG. 8, if a user selected to balance electrodes 106B, 108B, and 108C after programmer 40 generated target stimulation zone 118, then the shape of control shape 116 and/or the shape of target stimulation zone 118 may change to reflect the balancing. For example, prior to balancing, the contribution of electrode 108C to target stimulation zone 118 is less than the contributions of electrodes 106B and 108B as seen graphically by electrode 106B and electrode 108B being enveloped by target stimulation zone 118 and electrode 108C being partially covered by target stimulation zone 118. If a user selected to balance electrodes 106B, 108B, and 108C, then, after balancing, programmer 40 may display electrode 108C as also being enveloped by target stimulation zone 118, along with electrodes 106B, 108B.

In some examples, balancing (or equalizing) the contributions of each electrode of target stimulation zone 118 may alter target stimulation zone 118 as shown to the user. For example, target stimulation zone 118 that covers two or more electrodes may be "broken apart" into separate target stimulation zones that each cover only one electrode. These new individual stimulation zones may be desirable by a user to set parameters of individual electrodes or program certain IMDs. Balancing or equalizing electrodes is further described in FIGS. 33 and 34 described below.

It should be noted that a user may select to balance electrodes using the techniques described above either when stimulation is ON (stimulation is being delivered to a patient) or when stimulation is OFF (stimulation is not being delivered to a patient). If stimulation is OFF when a user attempts to balance two or more electrodes, programmer 40 may, in some examples, prompt a user to turn stimulation ON. For example, if a user selects two cathodes for balancing, and one of the cathodes is contributing (sourcing) 2% of the current and the other cathode is contributing (sourcing) 98% of the current, after balancing, each may contribute 50% of the current. Because a 48% increase or decrease in contribution is such a large change, it may be desirable to prompt a user to turn stimulation ON so that the user may step through the various intermediate stimulation zones. This may allow the user to stop the stimulation at one of the intermediate stimulation zones, as desired.

In addition, in one example implementation, after selecting to balance two or more electrodes, programmer 40 may display a confirmation to the user. For example, programmer 40 may display a window on user interface 59 that confirms the changes made by the user and requests that the user acknowledge the changes before programmer 40 applies those changes. Such a confirmation may prevent accidental or otherwise undesirable changes to stimulation.

An electrode's contribution is a multiplier of a master amplitude, where the master amplitude is the highest amplitude any individual electrode is delivering. In some examples, if a user changes a contribution of one electrode, e.g., a cathode, a user may actually change the master amplitude. For instance, if a user increases the contribution of an individual electrode from 50% of the master amplitude to a contribution that equates to an amount of current that is higher than the master amplitude, then the amplitude of the current delivered by the individual electrode becomes the new master amplitude and the remaining electrode contributions are modified to reflect a percentage of the new master amplitude. By way of specific example, assume that 10 mA is the master amplitude delivered by electrode X and that electrode Y has contribution of 0.5, or 5 mA. If the user increases the contribution of electrode Y to 1.5, or 15 mA (which is greater than the 10 mA master amplitude delivered by electrode X), then 15 mA becomes the new master amplitude and remaining electrode contributions are changed to reflect a percentage of the new master amplitude. For instance, the contribution of electrode X becomes 0.67 (10 mA/15 mA).

Figure 9:
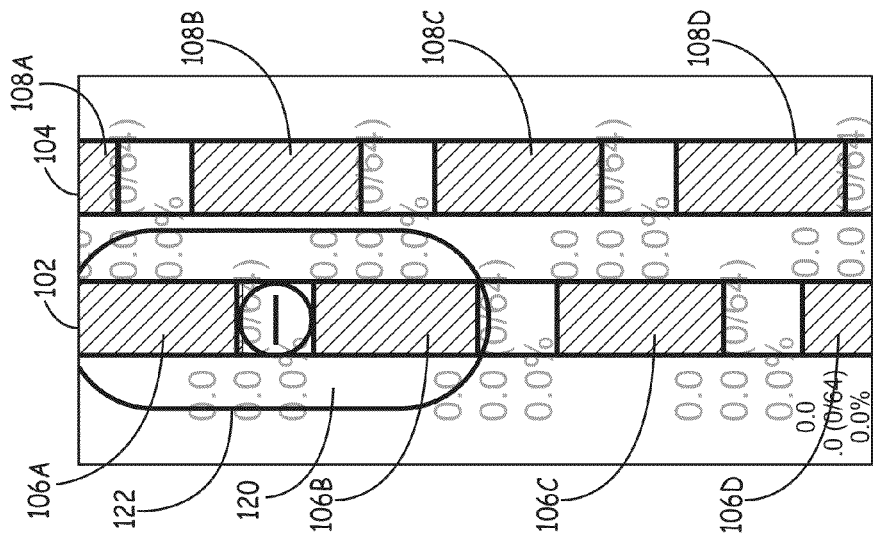
FIG. 9 is a conceptual diagram illustrating another example initial stimulation zone displayed in conjunction with a graphical representation of a portion of two implantable leads.

FIG. 9 is a conceptual diagram illustrating another example initial stimulation zone displayed in conjunction with a graphical representation of a portion of two implantable leads. In particular, FIG. 9 graphically depicts, e.g., on user interface 59 of programmer 40, an initial stimulation zone 120 along with a representation of a portion of first implantable lead 102 and a portion of second implantable lead 104. Unlike initial stimulation zone 100 of FIG. 6, initial stimulation zone 120 with control shape 122 is defined by a two electrodes, namely electrodes 106A and 106B on lead 102, recruited to provide stimulation to patient 6. Again, stimulation zone 120 may be referred to as the "initial" stimulation zone because it is the shape of the stimulation zone prior to the user stretching, moving, or otherwise manipulating the stimulation zone.

Figure 10:
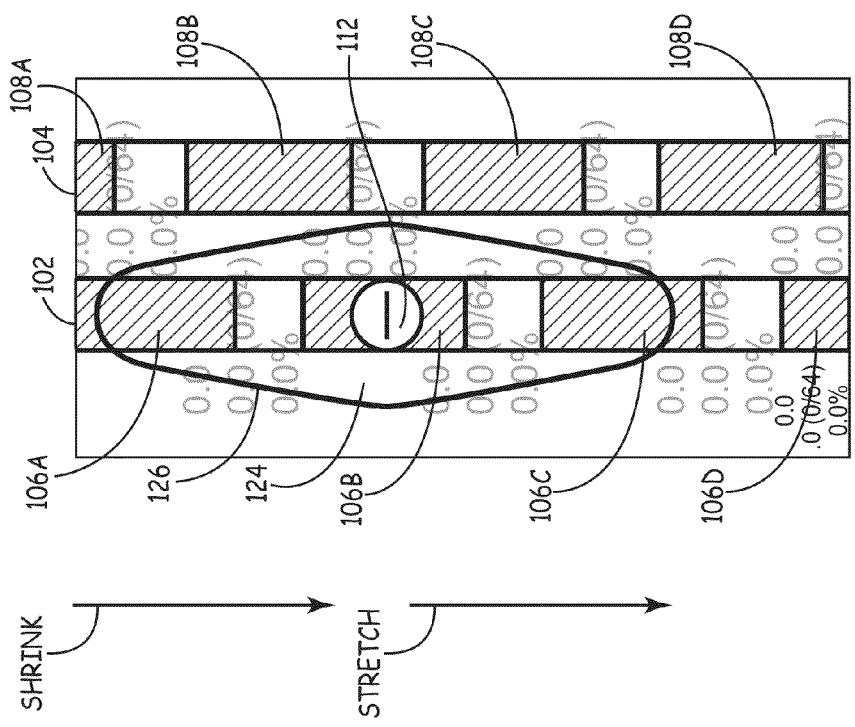
FIG. 10 is a conceptual diagram illustrating the stimulation zone of FIG. 9 following a stretch input and a shrink input.

FIG. 10 is a conceptual diagram illustrating the stimulation zone of FIG. 9 following a stretch input and a shrink input. In particular, FIG. 10 depicts target stimulation zone 124 with control shape 126 created following a stretch input and a shrink input of initial stimulation zone 120 of FIG. 9. A shrink input is similar to a stretch input. However, while a stretch input manipulates the control shape, e.g., control shape 126, away from the centroid of the stimulation zone, as indicated by icon 112, a shrink input manipulates the control shape, e.g., control shape 126, toward the centroid of the stimulation zone. For example, in FIG. 10, a user may use a pointing media to stretch the bottom of the graphical representation of initial stimulation zone 124 on user interface 59 of programmer 40 "downward" from electrode 106B toward electrode 106C on lead 10 and then shrink the top of the graphical representation of initial stimulation zone 124 "downward" from electrode 106A toward electrode 106B on lead 102. The stimulation zone may show specific control points to facilitate interaction, such as stretching and shrinking. These may include an exaggerated border for stretching, a "handle" that a user may "grasp" in order to stretch or shrink the zone, or specific boxes or dots at the corners to allow resizing. In this manner, the user may manipulate the oblong shape of initial stimulation zone 120 to the diamond-like shape of target stimulation zone 124.

As seen in FIG. 10, in response to the user's input, e.g., a stretch input and a shrink input, programmer 40 has recruited a third electrode, namely electrode 106C on lead 102, in order to provide the stimulation that may be required to generate target stimulation zone 124. Following the stretch and shrink inputs, target stimulation zone 124 is larger than initial stimulation zone 120 of FIG. 9 and defined by three electrodes, namely newly recruited electrodes 106C as well as the original electrodes 106A and 106B. In response to receiving user input, i.e., the shrink and the stretch inputs, programmer 40 and, in particular, processor 53, determines that electrodes 106C should be recruited to generate target stimulation zone 124. The contributions of electrodes 106A and 106C to target stimulation zone 118 are less than the contribution of electrodes 106B as seen graphically by electrode 106B being enveloped by target stimulation zone 124 and electrodes 106A and 106C being partially covered by target stimulation zone 124.

In some example implementations, it may be desirable to allow only one stimulation zone to be stretched/shrunk at a time. Programmer 40 may discard a pending target shape for the first zone if a user selects a second zone. For instance, a second stimulation zone may exist on lead 104 of FIG. 9 (not shown). If a user stretched the first stimulation zone on lead 102 of FIG. 9 in the manner depicted in FIG. 10, and then selected the second stimulation zone, programmer 40 may discard the pending target control shape for the first stimulation zone.

Figure 11:
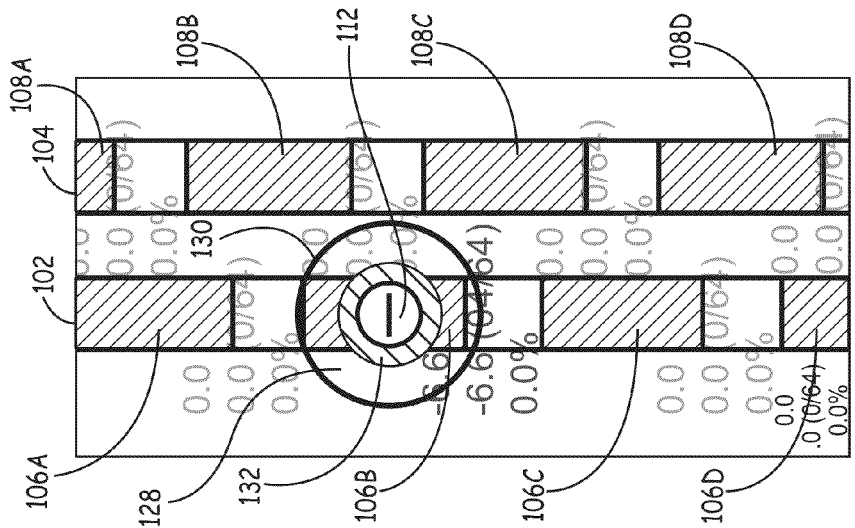
FIG. 11 is a conceptual diagram illustrating an example initial stimulation zone and an example initial stimulation field shape, displayed in conjunction with a graphical representation of a portion of two implantable leads.

FIG. 11 is a conceptual diagram illustrating an example initial stimulation zone and an example initial stimulation field shape, displayed in conjunction with a graphical representation of a portion of two implantable leads. FIG. 11 is similar to FIG. 6 and, as such, similar features will not be described for purposes of conciseness. FIG. 11 illustrates initial stimulation zone 128 with control shape 130. In addition, FIG. 11 depicts initial stimulation field shape 132. A field shape, e.g., field shape 132, is a graphical representation of the actual stimulation amplitude that is currently being delivered by IMD 4 via one or more electrodes, e.g., electrode 106B of lead 102. In particular, the size of the field shape is a graphical representation of the amplitude of the stimulation being delivered. A smaller field shape may indicate a lower amplitude, e.g., current or voltage amplitude, and a larger field shape may indicate a higher amplitude. A field shape may be graphically represented as an opaque shape displayed over one or more electrodes. In FIG. 11, field shape 132 is depicted as a circular shape located at the centroid of initial stimulation zone 128, shown at icon 112. In other examples (not shown), the field shape may not be circular. Rather, at higher amplitudes, one or more field shapes may become pear-shaped, dumbbell-shaped, or take on other non-circular shapes. These non-circular field shapes may be more prevalent to prevent overlapping when electrodes in close proximity and opposing polarity have relatively high amplitudes.

In addition to field shape 132, user interface 59 of programmer 40 may numerically display the stimulation amplitude associated with an electrode. For example, in FIG. 11, adjacent electrode 106B, three numbers are depicted. The top number, −6.6 mA, indicates the ideal or desired stimulation amplitude to be sourced or sunk by the electrode, e.g., electrode 106B. The middle number, −6.6 mA, indicates the actual stimulation amplitude that is sourced or sunk by the electrode. Finally, the bottom number indicates the error, e.g., in percent, between the ideal or desired stimulation amplitude and the actual stimulation amplitude. In FIG. 11, because the ideal or desired stimulation amplitude and the actual stimulation amplitude are equal, the error is 0.0%. Adjacent to the middle number is a parenthetical that indicates the number of parallel current regulator branches that may be used to implement the current regulator associated with the electrode, e.g., electrode 106B. For example, FIG. 11 depicts electrode 106B at full output, e.g., $64/64^{ths}$, for an example implementation with a resolution of $1/64$. In other words, in an example configuration in which one or more of 64 parallel current regulator branches may be used to implement each current regulator (i.e., a resolution of $1/64$), stimulation generator 60 may be set such that, for each of the highest contributing electrodes of the highest intensity active zone, all 64 parallel current regulator branches are used. It should be noted that there may be more or fewer parallel current branches that may be used to implement a current regulator and that 64 parallel current branches is only one example configuration.

Figure 12:
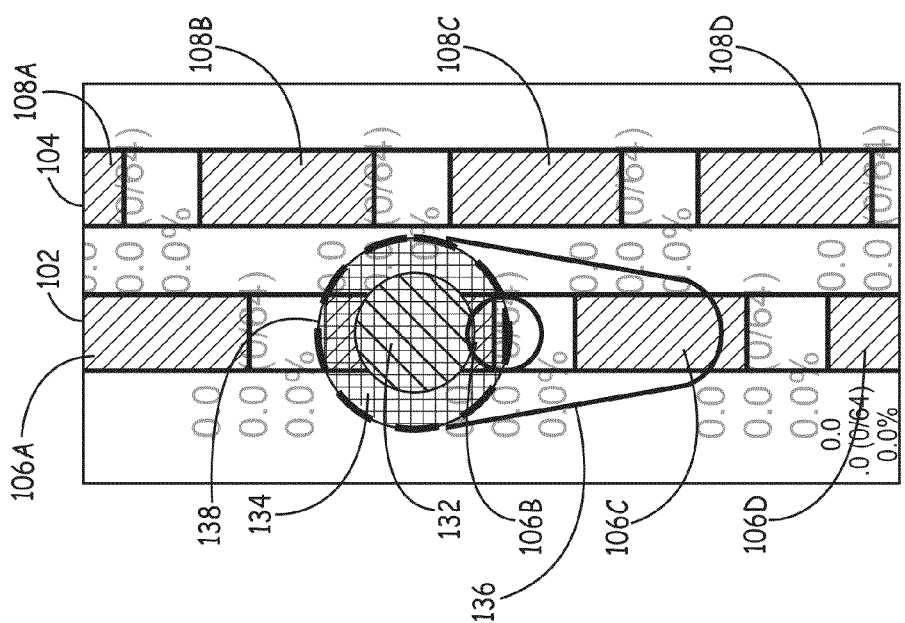
FIG. 12 is a conceptual diagram illustrating the initial stimulation zone and the initial stimulation field shape of FIG. 11 displayed in conjunction with a target stimulation zone generated by a single stretch input.

FIG. 12 is a conceptual diagram illustrating the initial stimulation zone and the initial stimulation field shape of FIG. 11 displayed in conjunction with a target stimulation zone generated by a single stretch input. Stretching (or shrinking) a stimulation zone allows a user to manipulate its shape. It is intended to allow fine tuning or optimization of a specific, existing area of stimulation or anodal guarding. Programmer 40 may immediately depict a stretch or shrink by changing the control shape, responsive to user input, while leaving the field shape as it was at the beginning of the stretch or shrink. Again, the starting or initial control shape may be represented by a dotted line static copy of the control shape. The initial control shape may not change throughout the stretch transition, which may cause the initial field shape to be outside of the control shape if a shrink has occurred. When manipulating the control shape, stimulation may not change instantly. In some cases, large changes can be effected. Using the techniques described in this disclosure, programmer 40 may allow the user to control the rate of progress through a sequence of intermediate stimulation zones towards the target stimulation zone defined by the target control shape, as described in more detail below with respect to intermediate stimulation zones, to reduce the rate or magnitude of jumps in stimulation that may result from the large changes. The intermediate stimulation zones may be automatically generated by programmer 40, stimulator 34, or a combination of the programmer and stimulator. In this manner, a single device may generate the intermediate stimulation zones or multiple devices may contribute to the generation of the intermediate stimulation zones.

FIG. 12 depicts target stimulation zone 134 with control shape 136 created following a single stretch of initial stimulation zone 128 of FIG. 11. For example, a user may use a pointing media such as a stylus, finger, or the like and stretch the graphical representation of initial stimulation zone 100 on user interface 59 of programmer 40 "downward" from electrode 106B toward electrode 106C.

Similar to the graphical representation shown in FIG. 7, in response to the user's input, e.g., a stretch, programmer 40 has recruited a second electrode, namely electrode 106C, in order to provide the stimulation that may be required by target stimulation zone 114. Unlike FIG. 7, FIG. 12 depicts field shape 132, which indicates that stimulation is currently being delivered by IMD 4 via electrode 106B. In addition, because stimulation is being delivered, FIG. 12 depicts a dotted line around initial or actual control shape 130 of FIG. 11, shown at 138 in FIG. 12, and a solid line around target control shape 136. In this manner, a user may easily distinguish between actual stimulation being delivered, e.g., shown as a dotted line around an initial control shape, and pending stimulation to be delivered, e.g., shown as a solid line around a target control shape. Of course, there are numerous ways in which the actual and pending stimulation may be differentiated from one another and the present disclosure is not limited to simply dotted or dashed lines and solids lines.

It should be noted that, although programmer 40 has recruited electrode 106C of lead 102 to deliver stimulation, electrode 106C is not yet delivering stimulation, as indicated by the lack of a field shape associated with electrode 106C. As such, control shape 134 may exist at one or more electrodes, e.g., electrode 106C, even though no stimulation is being delivered by the electrode(s). The lack of a field shape associated with electrode 106C provides an indication to the user that the representation of FIG. 12 is an intermediate phase between an initial phase (FIG. 11) and a final phase (FIG. 13, discussed below).

Figure 13:
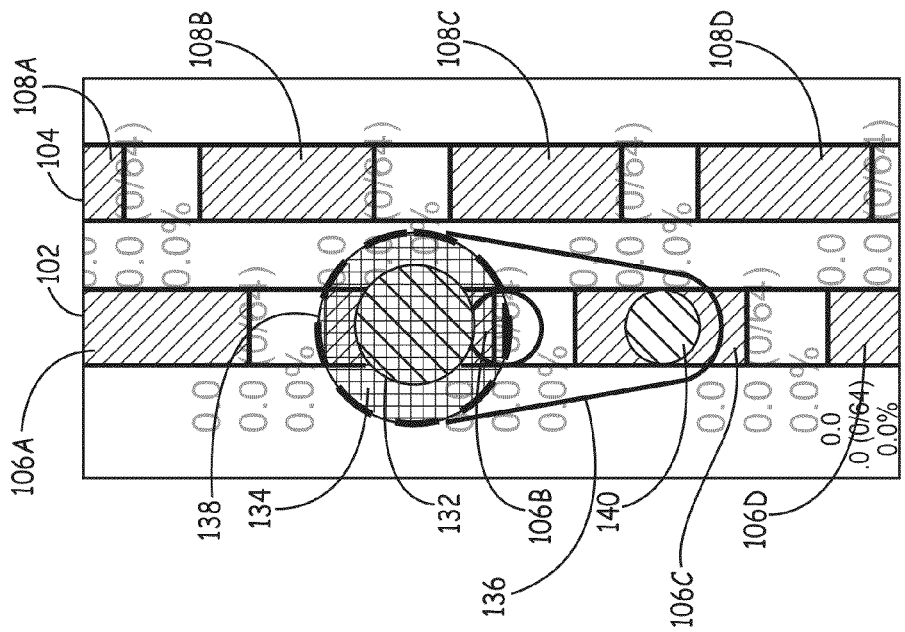
FIG. 13 is a conceptual diagram illustrating the initial stimulation zone and initial stimulation field shape of FIG. 11 displayed in conjunction with the target stimulation zone of FIG. 12 and a target stimulation field.

FIG. 13 is a conceptual diagram illustrating the initial stimulation zone and initial stimulation field shape of FIG. 11 displayed in conjunction with the target stimulation zone of FIG. 12 and a target stimulation field shape. FIG. 13 is similar to FIG. 12 and depicts the completion, or final phase, of the stretch of FIG. 12. Upon completion of the stretch (or other manipulation such as a shrink or move), programmer 40 displays a target stimulation field shape associated with the newly recruited electrode 106C. For example, programmer 40 displays target stimulation field shape 140 associated with recruited electrode 106C in FIG. 13. In this manner, programmer 40 "matches" the control shape and the field shapes by associating a field shape with each electrode that is used to deliver the stimulation required to produce the stimulation zone defined by the control shape. In FIG. 12, the control shape is not matched with field shapes because programmer 40 has recruited electrode 106C to deliver stimulation, but electrode 106C is not sinking (or sourcing) current yet. In FIG. 13, target control shape 136 is matched with the field shapes, namely field shapes 132, 140, because programmer 40 has associated a field shape with each electrode that is used to deliver the stimulation required to produce the stimulation zone defined by control shape 136. FIG. 13 also depicts a dotted line around initial or actual control shape 130 of FIG. 11, shown at 138 in FIG. 13, and a solid line around target control shape 136.

In addition, in some examples, when the stretch/shrink is ended by the user, whether mid-transition (FIG. 17, described below) or upon achieving the target control shape (FIG. 13), programmer 40 may remove the initial control shape and displays the control and field shapes that correctly represent the current stimulation amplitude.

As mentioned above, this disclosure describes various techniques for controlling a transition from an initial stimulation location or initial stimulation shape to a user-specified target stimulation location or target stimulation shape in order to limit the rate of change of stimulation. By controlling the transition, the rate of change of stimulation delivered to a patient may be limited in order to reduce or eliminate any discomfort that the patient may sense during the transition. FIG. 13 depicts the field shapes associated with electrodes 106B and 106C (and thus the stimulation amplitudes) at the target stimulation zone 134. As described in more detail below with respect to FIGS. 17-18, for example, programmer 40 may control IMD 4, i.e., an electrical stimulator, to transition electrical stimulation through one or more intermediate stimulation zones in order to transition from an initial stimulation zone to a target stimulation zone. That is, using the techniques of this disclosure IMD 4 may not jump from delivering the electrical stimulation graphically depicted in FIG. 11 (pre-stretch) to the electrical stimulation graphically depicted in FIG. 13. Rather, programmer 40 controls IMD 4 to smoothly transition between one or more intermediate stimulation zones in order to reach a user specified target stimulation zone, e.g., target stimulation zone 134.

For example, the amplitude of the electrical stimulation delivered via electrode 106C on lead 102 in FIG. 13 may gradually increase from zero to the amplitude represented by field shape 140. Using the techniques of this disclosure, programmer 40 may control IMD 4 to perform this gradual increase by transitioning through one or more intermediate stimulation zones. A stimulation zone is an area of stimulation defined by one or more electrodes recruited to provide stimulation (or guarding/shielding in the case of anodal zones), their contributions, and an intensity. Thus, in FIG. 13, an intermediate stimulation zone is the area of stimulation defined by electrodes 106B and 106C (the recruited electrodes), their contributions, and an intensity associated with each electrode. Programmer 40 may determine that one or more intermediate stimulation zones are desirable in order to perform the gradual increase, thereby allowing a smooth transition between an initial stimulation zone, e.g., initial stimulation zone 128 of FIG. 11, and a target stimulation zone, e.g., target stimulation zone 134 of FIG. 12. Again, intermediate stimulation zones are described in more detail below.

It should be noted that in some example implementations, IMD 4 continues to deliver electrical stimulation during a transition from an initial stimulation zone, e.g., as shown in FIG. 11, to a target stimulation zone, e.g., as shown in FIG. 13, in order to prevent IMD 4 from having to ramp up its intensity from zero upon reaching the target stimulation zone.

Figure 14:
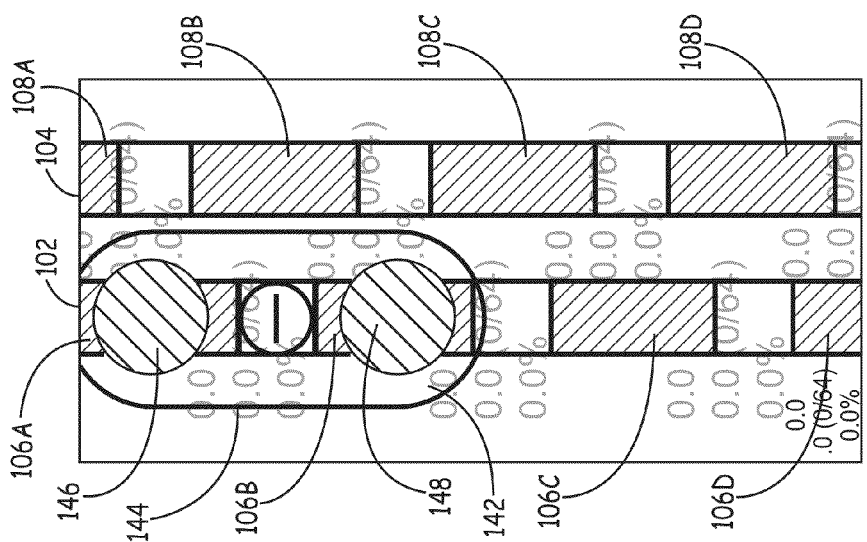
FIG. 14 is a conceptual diagram illustrating an example initial stimulation zone and two example stimulation field shapes, displayed in conjunction with a graphical representation of a portion of two implantable leads.

FIG. 14 is a conceptual diagram illustrating an example initial stimulation zone and two example stimulation field shapes, displayed in conjunction with a graphical representation of a portion of two implantable leads. FIG. 14 is similar to FIG. 9 and, as such, similar features will not be described for purposes of conciseness. FIG. 14 illustrates initial stimulation zone 142 with control shape 144. In addition, FIG. 14 depicts initial stimulation field shape 146 (associated with electrode 106A of lead 102) and initial stimulation field shape 148 (associated with electrode 106B of lead 102).

Figure 15:
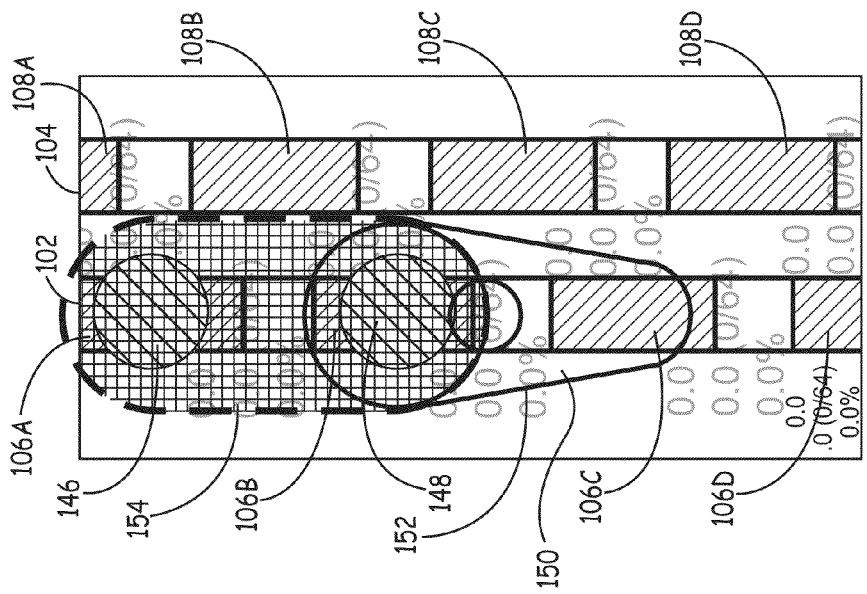
FIG. 15 is a conceptual diagram illustrating the initial stimulation zone and initial stimulation field shapes of FIG. 14 displayed in conjunction with a target stimulation zone generated by a single stretch input.

FIG. 15 is a conceptual diagram illustrating the initial stimulation zone and initial stimulation field shapes of FIG. 14 displayed in conjunction with a target stimulation zone generated by a single stretch input. FIG. 15 depicts target stimulation zone 150 with control shape 152 created following a single stretch of initial stimulation zone 142 of FIG. 14. In FIG. 15, programmer 40 has received user input that stretched initial stimulation zone 142 of FIG. 14 "downward" toward electrode 106C on lead 102. FIG. 15 depicts initial stimulation field shape 146 (associated with electrode 106A of lead 102) and initial stimulation field shape 148 (associated with electrode 106B of lead 102), which indicate that stimulation is currently being delivered by IMD 4 via electrodes 106A and 106B. In addition, because stimulation is being delivered, FIG. 15 depicts a dotted line around initial, i.e., actual, control shape 144 of FIG. 14, shown at 154 in FIG. 15, and a solid line around target control shape 152.

Although programmer 40 has recruited electrode 106C of lead 102 to deliver stimulation, electrode 106C is not yet delivering stimulation, as indicated by the lack of a field shape associated with electrode 106C. As such, target control shape 150 may exist at one or more electrodes, e.g., electrode 106C, even though no stimulation is being delivered by the electrode(s). The lack of a field shape associated with electrode 106C provides an indication to the user that the representation of FIG. 15 is an intermediate phase between an initial phase (FIG. 14) and a final phase (FIG. 16, discussed below).

Figure 16:
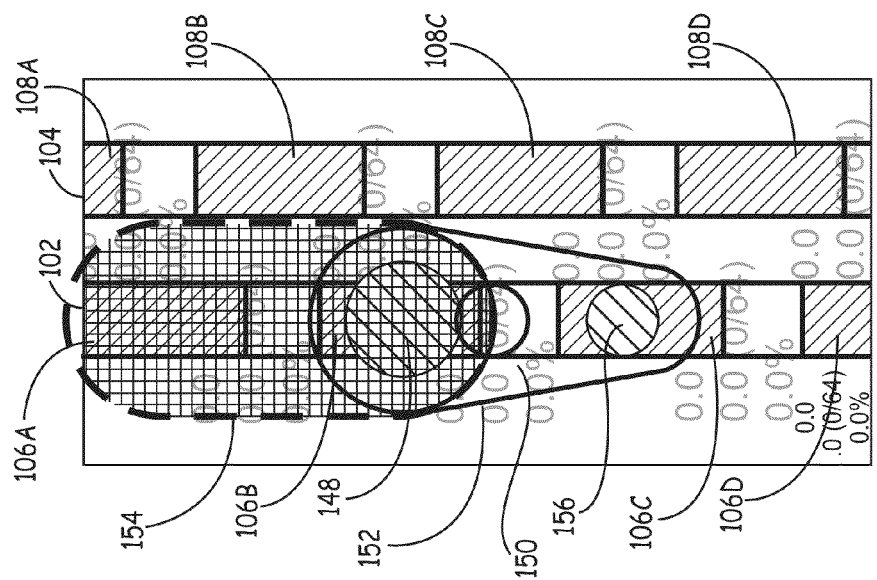
FIG. 16 is a conceptual diagram illustrating the initial stimulation zone and one initial stimulation field shape of FIG. 14 displayed in conjunction with the target stimulation zone of FIG. 15 and a target stimulation field.

FIG. 16 is a conceptual diagram illustrating the initial stimulation zone and one initial stimulation field shape of FIG. 14 displayed in conjunction with the target stimulation zone of FIG. 15 and a target stimulation field shape. FIG. 16 is similar to FIG. 15 and depicts the completion, or final phase, of the stretch of FIG. 15. Upon completion of the stretch (or other manipulation such as a shrink or move), programmer 40 displays a target stimulation field shape associated with the newly recruited electrode 106C. In particular, programmer 40 displays field shape 156 associated with recruited electrode 106C as well as field shape 148 associated with electrode 106B, indicating that both electrodes 106B and 106C are delivering electrical stimulation to patient 6. In this manner, programmer 40 "matches" target control shape 152 and field shapes 148, 156. FIG. 16 also depicts a dotted line around initial or actual control shape 144 of FIG. 14, shown at 154 in FIG. 16, and a solid line around target control shape 152.

Figure 17:
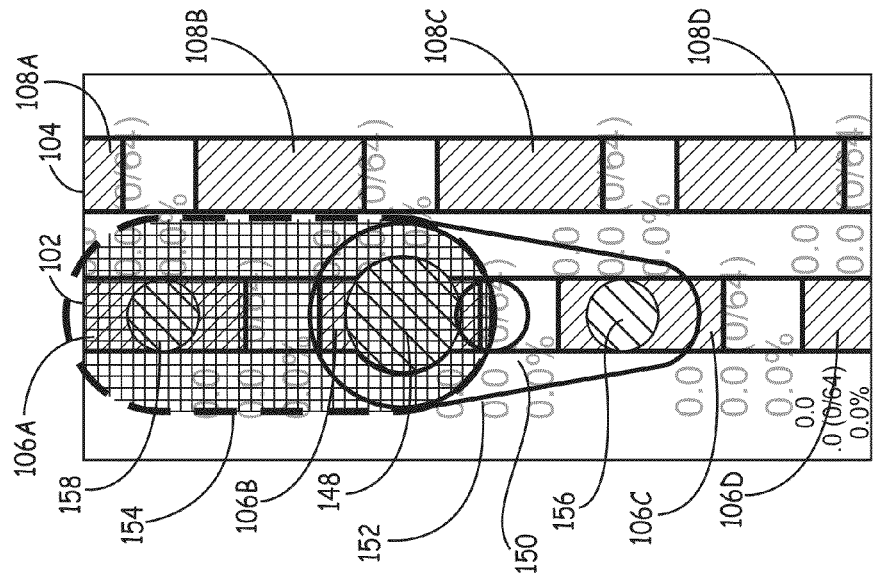
FIG. 17 is conceptual diagram illustrating intermediate field shapes that define an intermediate stimulation zone following the single stretch input of FIG. 15.

FIG. 17 is conceptual diagram illustrating intermediate field shapes that define an intermediate stimulation zone following the single stretch input of FIG. 15. As indicated above, this disclosure describes various techniques for medical devices that deliver electrical stimulation therapy for controlling a transition from an initial stimulation location or initial stimulation shape to a user-specified target stimulation location or target stimulation shape in order to limit the rate of change of stimulation. In this manner, the rate of change of stimulation delivered to a patient may be limited in order to reduce or eliminate any discomfort that the patient may sense during the transition.

FIG. 17 depicts the field shapes associated with electrodes 106A-106C (and thus the stimulation amplitudes) at a particular intermediate stimulation zone of one or more intermediate stimulation zones that programmer 40 controls IMD 4, i.e., an electrical stimulator, to transition electrical stimulation through in order to transition from an initial stimulation zone to a target stimulation zone. In other words, IMD 4 may not jump from delivering the electrical stimulation graphically depicted in FIG. 15 to the electrical stimulation graphically depicted in FIG. 16. Rather, programmer 40 controls IMD 4 to smoothly transition between one or more intermediate stimulation zones in order to reach a user specified target stimulation zone. As seen in FIG. 17, three field shapes are depicted, namely field shapes 148, 156, and 158. Field shape 148, associated with electrode 106B, is the largest, indicating that it has the largest contribution of electrodes 106A-106C to the intermediate stimulation zone of FIG. 17. Field shape 156, associated with electrode 106C, is the smallest, indicating that it has the smallest contribution to the intermediate stimulation zone of FIG. 17. As indicated above, a stimulation zone is an area of stimulation defined by one or more electrodes recruited to provide stimulation (or guarding/shielding in the case of anodal zones), their contributions, and an intensity. Thus, the intermediate stimulation zone of FIG. 17 is the area of stimulation defined by electrodes 106A-106C, their contributions, and an intensity associated with each electrode, as represented by the size of field shapes 148, 156, and 158. FIG. 17 does not graphically depict an outline of the intermediate stimulation zone, but instead relies on the size and shape of field shapes 148, 156, and 158 to graphically indicate the intermediate stimulation zone. By way of specific example, electrodes 106A-106C, associated with field shapes 158, 148, and 156, may deliver stimulation amplitudes of −3 mA, −6 mA, and −1 mA, respectively. These stimulation amplitudes, or intensities, define the field shapes and together define the intermediate stimulation zone of FIG. 17. As mentioned above, in other examples (not shown), the field shape may not be circular. Rather, at higher amplitudes, one or more field shapes may become pear-shaped, dumbbell-shaped, or take on other shapes to prevent adjacent field shapes from overlapping.

Of course, there may be numerous additional intermediate stimulation zones that programmer 40 may control IMD 4 to transition through in order to transition from initial stimulation zone 142 of FIG. 14 to target stimulation zone 150 of FIG. 15. For example, a hypothetical intermediate stimulation zone existing in time prior to FIG. 17 (not shown) may include a field shape associated with electrode 106A that is larger, e.g., defined by an amplitude of −4 mA, than field shape 158 of FIG. 17, based on the fact that the amplitude of the stimulation delivered via electrode 106A is decreasing from the amplitude represented by field shape 146 in FIG. 14. And, the hypothetical intermediate stimulation zone existing in time prior to FIG. 17 may include a field shape associated with electrode 106C that is smaller e.g., defined by an amplitude of −0.5 mA, than field shape 156 of FIG. 17, based on the fact that the amplitude of the stimulation delivered via electrode 106C is increasing from zero in FIG. 14. So, the field shapes may become progressively smaller or larger during the transition through intermediate control shapes.

Similarly, another hypothetical intermediate stimulation zone existing in time after FIG. 17 (not shown) may include a field shape associated with electrode 106A that is smaller e.g., defined by an amplitude of −2 mA, than field shape 158 of FIG. 17, based on the fact that the amplitude of the stimulation delivered via electrode 106A is continuing to decrease from the amplitude represented by field shape 146 in FIG. 14. And, the hypothetical intermediate stimulation zone existing in time after FIG. 17 may include a field shape associated with electrode 106C that is larger e.g., defined by an amplitude of −2 mA, than field shape 156 of FIG. 17, based on the fact that the amplitude of the stimulation delivered via electrode 106C is increasing from zero in FIG. 14.

The hypothetical intermediate stimulation zones described above are just two intermediate stimulation zones, along with the intermediate stimulation zone of FIG. 17, that programmer 40 may control IMD 4, i.e., an electrical stimulator, to transition electrical stimulation through in order to transition from an initial stimulation zone to a target stimulation zone. There may be many more intermediate stimulation zones that IMD 4 may transition through. For example, Table 1 below describes ten stimulation zones. In some examples, however, there may only be one intermediate stimulation zone between an initial stimulation zone and a target stimulation zone. For instance, if programmer 40 receives user input via user interface 59, e.g., a stretch or shrink, indicating a target stimulation zone that is only slightly different from an initial stimulation zone, programmer 40 may only generate a single intermediate stimulation zone in order to prevent the user from feeling any discomfort from the transition. By providing one or more intermediate stimulation zones between an initial stimulation zone and a target stimulation zone, the rate of change of stimulation delivered to a patient may be limited in order to reduce or eliminate any discomfort that the patient may sense during the transition. In particular, by limiting the amount of change between intermediate stimulation zones, the overall rate of change of stimulation may be controlled, as will be described in more detail below. Although programmer 40 may individually generate the intermediate stimulation zones, stimulator 34, or a combination of programmer 40 and stimulator 34, may generate the intermediate stimulation zones based on the initial and target stimulation zones.

In some instances, it may be desirable to terminate a stretch (or shrink or other manipulation of a stimulation zone), prior to completion of the stretch. For example, a clinician may stop a stretch during a transition to query a patient with respect to the perceived efficacy of the stimulation at that particular point in the transition. As described above, FIG. 17 depicts an intermediate stimulation zone through which IMD 4, i.e., an electrical stimulator, may transition in order to transition from an initial stimulation zone to a target stimulation zone. If a stretch is terminated prior to reaching completion, then it may be desirable to set the control shape to match the actual electrodes in use at the time of the termination. For example, FIG. 17 depicts the field shapes associated with electrodes 106A-106C if a user terminated the stretch initiated in FIG. 15 prior to its completion in FIG. 16. However, rather than depicting a control shape based on field shapes 158, 148, and 156 associated with electrodes 106A-106C, i.e., the actual field shapes used to produce the intermediate stimulation zone, FIG. 17 depicts initial or actual control shape 144 of FIG. 14, shown at 154, and target control shape 152. As such, it is desirable to set the control shape to match the actual control shape that defines the intermediate stimulation zone of FIG. 17.

Figure 18:
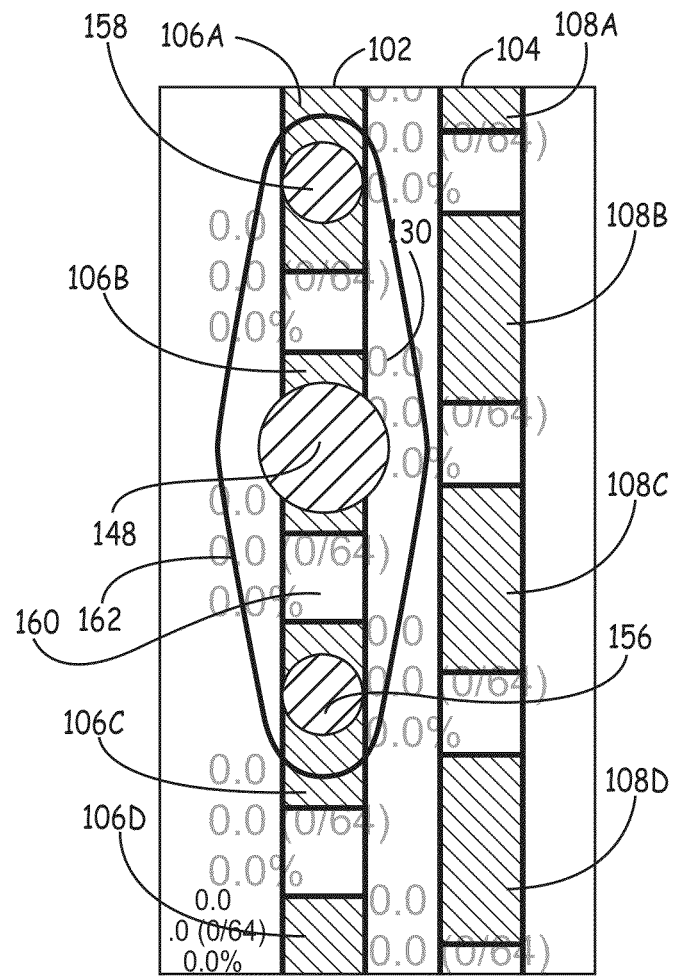
FIG. 18 is conceptual diagram illustrating an intermediate stimulation zone defined by the intermediate field shapes of FIG. 17.

FIG. 18 is conceptual diagram illustrating an intermediate stimulation zone defined by the intermediate field shapes of FIG. 17. In particular, FIG. 18 depicts the intermediate stimulation zone, now indicated at 160, defined by the intermediate field shapes 158, 148, and 156 in FIG. 17. In addition, the initial and target control shapes of FIG. 17 have been "fixed" in FIG. 18 to match the actual control shape, namely control shape 162, that defines intermediate stimulation zone 160. Matching the control shape with the field shapes allows programmer 40 to display the stimulation zone that is defined by field shapes 158, 148, and 156 to a user, e.g., a clinician or patient.

Figure 19:
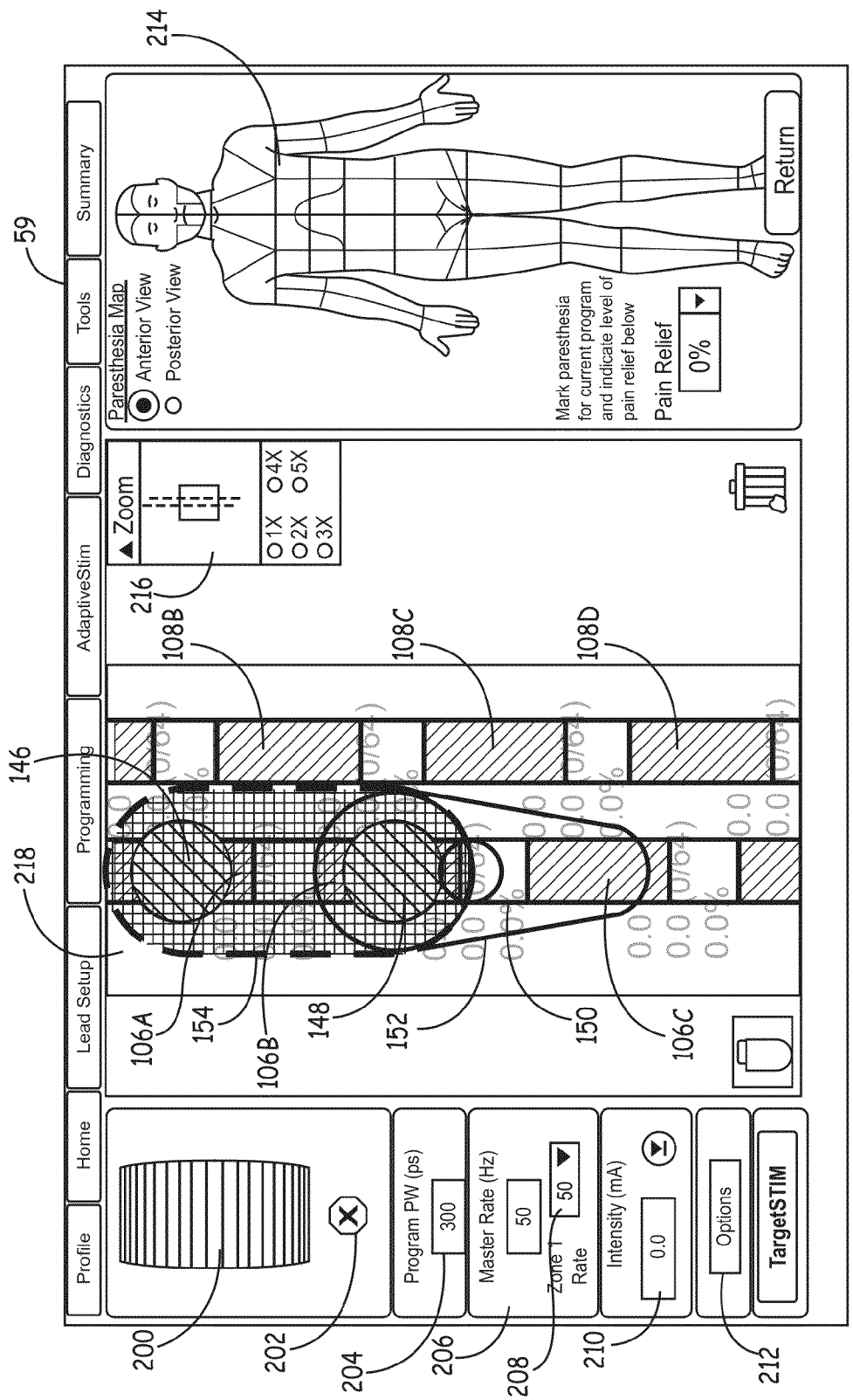
FIG. 19 illustrates an example programmer screen, in accordance with this disclosure.

FIG. 19 illustrates an example programmer screen, in accordance with this disclosure. FIG. 19 represents an example screen presented on programmer 40 that may be used to control the rate of change from an initial stimulation zone to a target stimulation zone through one or more intermediate stimulation zones. The example screen illustrates the conceptual diagram shown and described above with respect to FIG. 15. For purposes of conciseness, similar features will not be described in detail again.

In addition, FIG. 19 depicts the following: scroll wheel 200, which allows a user to increase or decrease the intensity of the stimulation, the pulse width, and the pulse rate; stop icon 202, which allows a user to stop the change in stimulation resulting from an input to scroll wheel 200; programmable pulse width control 204; master frequency control 206; zone frequency control 208; master intensity control 210, which allows a user to modify the intensity of the strongest single electrode or to modify the sum total of all of the cathodic (or anodic) electrodes; options icon 212, which allows a user to change the time-base between intermediate stimulation zone transitions, change the step size between intermediate stimulation zone transitions, change the type of change profile (linear rise vs. one or more nonlinear curves), change whether the transition starts automatically or waits for further input, change the behavior of the transition on detection of errors (pause, cancel, or continue unimpeded), or change aesthetic aspects of the transition (colors used to indicate initial and final shapes, etc); paresthesia map 214, which allows a user to input an area of the body to which stimulation is desired; and zoom control 216, which allows a user to increase or decrease the leads, stimulation zones, and the like displayed within display window 218. In accordance with the techniques of this disclosure, when a user stretches, shrinks, or otherwise manipulates an initial stimulation zone or control shape, a transition control input becomes available for user input. As seen in display window 218 of FIG. 19, a user has stretched an initial stimulation zone, indicated by control shape 154, to a target stimulation zone, indicated by control shape 152. In response, programmer 40 displays a transition control input, shown and described below with respect to FIG. 20. In some examples, the transition from the initial stimulation zone to the target stimulation zone via one or more intermediate stimulation zones does not occur until a user has initiated the transition using the transition control input of FIG. 20.

Figure 20:
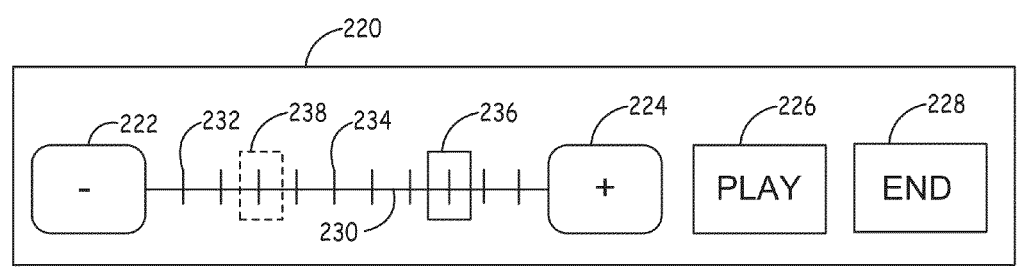
FIG. 20 illustrates an example transition control input, in accordance with this disclosure.

FIG. 20 illustrates an example transition control input. As mentioned above, transition control input 220 may be displayed via user interface 59 of programmer 40 when a user stretches, shrinks, or otherwise manipulates an initial stimulation zone or control shape. In some examples, transition control input 220 may only appear after the user performs the stretch, shrink, or the like. Transition control input 220 includes decrement input 222, e.g., a "minus" sign, an increment input 224, e.g., a "plus" sign, an initiate or play input 226, and an end input 228. In some examples, transition control input may be a slider bar, e.g., slider bar 230. Slider bar 230 may include one or more indicators 232 that correspond to a respective intermediate stimulation zone through which programmer 40 may control IMD 4, i.e., an electrical stimulator, to transition in order to transition from an initial stimulation zone to a target stimulation zone. In order words, indicators 232 on slider bar 230 correspond to steps from an initial control shape to a target control shape. In FIG. 20, the initial control shape is represented by the indicator on the far left of slider bar 230 and the target control shape is represented by the indicator on the far right of slider bar 230. By way of specific example, the intermediate stimulation zone described above with respect to FIG. 17 may be represented by indicator 234, i.e., an indicator 232 that is intermediate (between) an initial stimulation zone and a target stimulation zone. In some example implementations, the number of indicators 232 on slider bar 230 may vary, depending on the magnitude of change in the control shape. In response to slight shrinks or stretches, programmer 40 may only display one or two indicators 232 while larger changes in control shapes may result in more indicators 232.

As further seen in FIG. 20, slider bar 230 further includes slider thumb 236 (also referred to as a "slider"), which a user may tap and drag, copy/paste, or otherwise move from one indicator 232 on slider bar 230 to another indictor 232 on slider bar 230, thereby allowing the user to set the position of slider thumb 236 directly. The location at which the user positions the slider thumb becomes a target stopping point for the stretch or shrink transition. In some examples, phantom slider thumb 238 may be left behind at the starting indicator in order to graphically display the position of the initial control shape, and help to illustrate a transition from an initial control shape to a target control shape. In other words, transition control input 220 may illustrate the current indicator as well as the indicator to which the slider thumb (and thus the stimulation) is transitioning. Dragging slider thumb 238 right or left may indicate to programmer 40 that a user desires that a particular series of steps be taken and programmer 40, in response, may automatically apply the series of steps on a time basis, e.g., user configurable, so that slider thumb 238 moves towards the user specific target at a controlled rate of change.

In other examples, programmer 40 may receive input via decrement input 222 and increment input 224, thereby allowing the user to move slider thumb 236 toward or away from the target control shape. For example, one click of either decrement input 222 or increment input 224 may result in slider thumb 236 moving one indicator position to the left or the right, depending on the input received.

Once the position of slider thumb 236 is set at the desired indicator 232, the user may click or otherwise provide input to an initiate input, shown graphically as "PLAY" button 226 in FIG. 20. In response, programmer 40 transitions an initial stimulation zone or initial control shape toward the target stimulation zone or target control shape. In other examples, rather than pressing PLAY to initiate a sequence from one indicator to another indicator, the sequence may begin automatically after a predetermined and user configurable amount of time has elapsed. In other words, a transition from an initial stimulation zone to a target stimulation zone may be pending until a user initiates the transition, e.g., via an initiate input such as the PLAY button, or the transition may occur automatically after some amount of time has elapsed following user input to transition control input 220. In some examples, the input that initiates the transition may initiate an automatic or semi-automatic transition that is at least partially controlled by programmer 40. In other examples, the user input that initiates the transition may be the first user controlled step in user controlled steps (e.g., manual steps) through the intermediate stimulation zones and ending with the target stimulation zone. In other words, the user input may control, or otherwise be required to transition to, each of the intermediate stimulation zones and the target stimulation zone in a fully manual transition mode. Each of these different types of transitions may be configurable or selected by the user. In other words, the user may determine the degree of automation or manual control through the transition from the initial stimulation zone to the target stimulation zone.

In another example, rather than dragging slider thumb 236, transition control 220 may receive user input, such as a click via a pointing media, directly on an indicator 232. In response, programmer 40 may immediately set that particular indicator as the target.

In order to provide a smooth transition from the initial stimulation zone to the target stimulation zone, a time may be set between each step, or intermediate stimulation zone, thereby controlling the rate of change during the transition. For example, programmer 40 may control IMD 4 to remain at each intermediate stimulation zone for a predetermined period of time, e.g., one second, before moving to the next stimulation zone (whether another intermediate stimulation zone or the target stimulation zone). The predetermined period of time may be user programmable in some examples. In other examples, it may be desirable to increase or decrease the amount of time at each intermediate stimulation zone. To terminate a transition, a user may click on END button 228. In some examples, the stretch or shrink mode may be in effect until the user clicks END button 228, the user deselects the current stretch or shrink, the user begins another stretch or shrink, or until the user provides some other input to programmer 40 that indicates the user is finished with the current stretch or shrink and desires to perform another stretch or shrink, for example.

During the transition, PLAY button 226 may become a "PAUSE" button. Clicking the PAUSE button may result in the transition, e.g., stretch or shrink, to stop indefinitely at the current step. For example, during the transition from the representation shown in FIG. 15 to the representation shown in FIG. 16, a user may have clicked the PAUSE button or END input 228, resulting in the stimulation configuration depicted in and described above with respect to FIG. 17. It should be noted that, in some examples, the transition is stopped indefinitely by clicking on the PAUSE button, but the stimulation may continue to be applied using the stimulation parameters associated with the particular step at which the transition was paused. As indicated above, if a stretch or shrink is terminated prior to completion, i.e., prior to reaching the target control shape as specified by the user, the control shape may be updated to match the actual outputs of the electrodes.

In some example implementations, during the transition from an initial stimulation zone to a target stimulation zone, program intensity input 210 and scroll wheel 200 (both of FIG. 19) are not selectable. Instead, program intensity input 210 updates throughout the transition to display a current intensity. If the PAUSE button is clicked, or if the transition to the target stimulation zone is complete, program intensity input 210 becomes selectable. At this point, the user may select the program intensity and use scroll wheel 200 to increment or decrement the global intensity as desired.

Again, an electrode's contribution is the degree to which a given electrode delivers a desired intensity to the zone that recruited the electrode. The electrode contribution may have a value between 0.0 and 1.0. In some example implementations, if a stretch, shrink, or other operation is ended with a recruited electrode in a state such that the electrode has less than 0.2 contribution, then the stimulation zone existing at the time the operation is ended is broken into multiple one-electrode zones, consistent with manual amplitude adjustment of individual electrodes and electrode recruitment rules. Electrode contributions are described in detail in U.S. Provisional Application No. 61/260,644, entitled, "MANAGING ELECTRICAL STIMULATION THERAPY BASED ON VARIABLE ELECTRODE COMBINATIONS," and filed on Nov. 12, 2009, by Goetz et al., the entire content of which is incorporated herein by reference.

In other example implementations, if IMD 4 is not delivering stimulation or if the zone is being stretched, shrunk, or the like is OFF, i.e., all electrodes in the zone have an amplitude equal to zero, then the stretch (or shrink) may occur instantaneously. In this scenario, the target control shape becomes the actual control shape as soon as it is updated by the user, thereby eliminating the need for the transition control input.

Transitions from an initial stimulation zone to a target stimulation zone may be accomplished using numerous different methods. One such method is described below. Processor 53 of programmer 40, for example, compares the target control shape to the initial control shape, and determines any differences between the two shapes. Each difference, whether an increase (stretch) or decrease (shrink) may be divided into a fixed number of steps. As the user manipulates transition control input 220, e.g., slider bar 230, the steps are applied in sequence to each of the changing electrodes until the electrodes reach their target values, as determined by processor 53. Once the stretch (or shrink) is complete, the transition control input may, in some examples, disappear (or otherwise become inoperable until programmer 40 receives additional input from a user such as a stretch or shrink input) and other programming activities using programmer 40 may commence.

In some example implementations, user interface 59 of programmer 40 may preview changes to the initial stimulation zone after transition control input 220 receives user input. As a user manipulates transition control input 220, programmer 40 may display a representation of what the field looks like at that particular indicator. For example, as a user drags or otherwise relocates slider thumb 236 to various indicators 232, programmer 40 may preview the intermediate stimulation zone corresponding to the particular indicator 232 by displaying an overview or a dotted line of the stimulation zone. In other examples, the user may hover over a particular indicator 232 and programmer 40 may display a pop-up window with a representation of the stimulation zone corresponding to that particular indicator. In some examples, programmer 40 may display a "film-strip," which shows in a series of "thumb-nail" windows what the representation of the stimulation would look like at corresponding indicators 232. For example, in FIG. 20, programmer 40 may display a film-strip which includes thumb-nail representations for each of the indicators 232 that are shown on transition control input 220.

In another example implementation, programmer 40 may depict an initial stimulation zone using a first color and/or a first line style, e.g., dashed line, and a target stimulation zone using a second color and/or a second line style, e.g., solid line. Programmer 40 continues to depict the initial stimulation zone and the target stimulation zone while depicting the particular intermediate stimulation zone for which stimulation is currently being delivered using a third color and/or a third line style, e.g., dot and dashed line. Such an implementation may provide a user with a summary illustration of the transition.

Indicators 232 may be related to one another linearly or non-linearly. In other words, the incremental steps between each indicator 232 may be of fixed size or may vary according to an exponential, logarithmic or algorithmic change in accordance with the particular transition requested by the user. The incremental steps between each indicator 232 may also vary by a linear function, power law, or other function. If non-linearly related, indicators 232 may be spaced out non-linearly, i.e., the step size between indicators 232 will vary to indicate that changes between certain indicators 232 are larger than changes between other indicators 232. In some examples, initial changes to stimulation may be below a patient's perception threshold, i.e., sub-threshold. In other examples, changes may be large initially, and then decrease towards the target. For example, there may be a 20% change in amplitude between a first indicator and a second indicator, then a 15% change in amplitude between the second indicator and a third indicator, then a 10% change in amplitude between the third indicator and a fourth indicator, and so forth. The step size between indicators 232 may correlate or otherwise be related to the rate of change of the transition. The number of indicators 232 shown in FIG. 20 may correspond to the size of the transition, e.g., stretch, shrink, or move.

As mentioned above, in some example implementations, a user may change the time-basis between intermediate stimulation zone transitions using options icon 212. In other words, the user may set the amount of time at which IMD 4 delivers stimulation at each indicator 232. For example, it may be desirable to allow an interval of one second between each indicator 232. In other example, the interval may be a longer or shorter interval. The timing of the interval may be dependent upon on the magnitude of the changes to the initial stimulation zone, or on the particular type of leads in use. Leads with narrowly-spaced electrodes may reflect subtle changes better than leads with electrodes that are far apart from one another. As such, there may be more steps or indicators for leads with narrowly-spaced electrodes and fewer steps or indicators for leads with electrodes that are far apart from one another. A user may change either the step size or time basis on which changes are applied using options icon 212. For example, it may be desirable to have a longer time basis for transverse changes to stimulation (across leads) than for longitudinal changes to stimulation (along leads). Thus, transition control input 220 is adaptive because the number of indicators may vary and because the relationship between indicators may be linear, non-linear, or fixed, for example, depending on the change requested or the leads.

Using transition control input 220, a user may, in effect, define an initial stimulation zone and target stimulation zone, automatically generate a set of intermediate stimulation zones, and playback the sequence like a video or audio file, similar to a media transport control for a media player, e.g., a DVD player or CD player. Either programmer 40, stimulator 34, or a combination of programmer 40 and stimulator 34, may automatically generate the set of intermediate stimulation zones.

Figure 22:
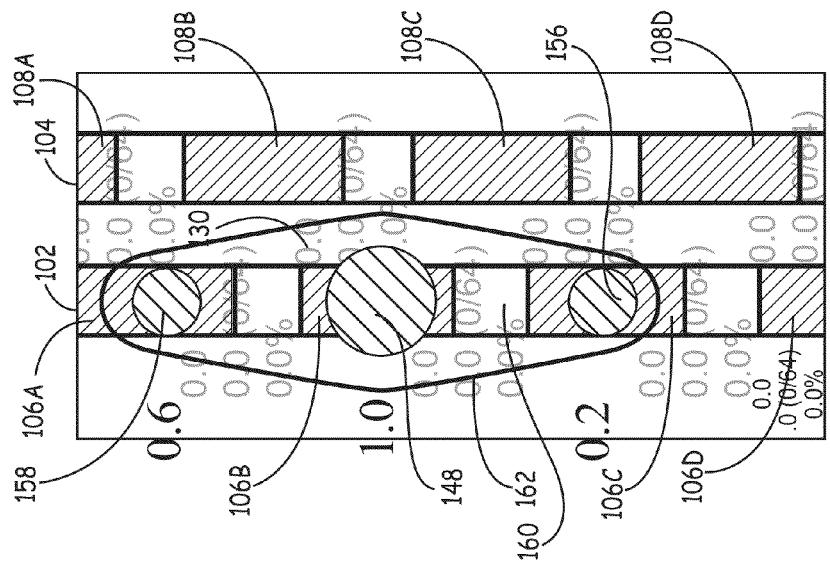
FIGS. 21-22 are conceptual diagrams illustrating example stimulation zones and their respective electrode contributions.
Figure 21:
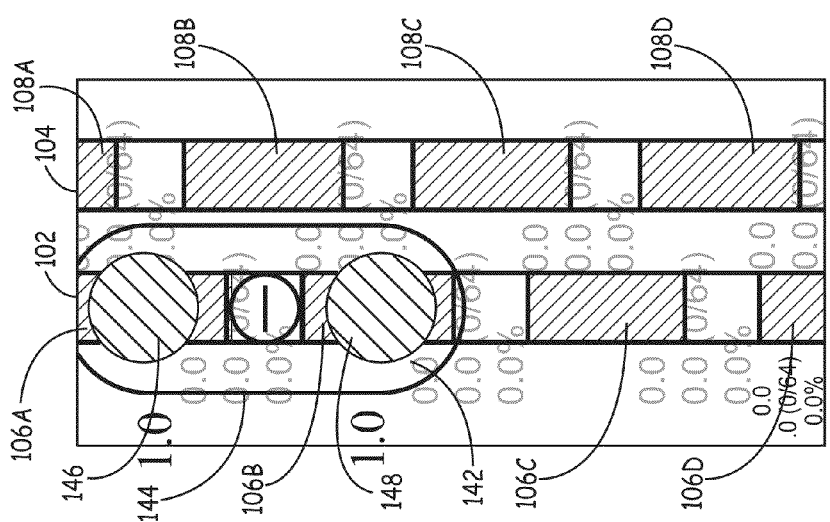

FIGS. 21 and 22 are conceptual diagrams illustrating example stimulation zones and their respective electrode contributions. FIG. 21 depicts the initial stimulation zone depicted and described above with respect to FIG. 14. FIG. 21 further depicts the contributions of the electrodes recruited to generate initial stimulation zone 142. In particular, FIG. 21 depicts electrode 106A as having a contribution of 1.0 and electrode 106B as having a contribution of 1.0. In other words, electrodes 106A and 106B contribute equally to the intensity of initial stimulation zone 142.

FIG. 22 depicts the intermediate stimulation zone depicted and described above with respect to FIG. 18. FIG. 22 further depicts the contributions of the electrodes recruited to generate intermediate stimulation zone 160. In particular, FIG. 22 depicts electrode 106A as having a contribution of 0.6, electrode 106B as having a contribution of 1.0, and electrode 106C as having a contribution of 0.2. In other words, electrode 106B contributes the most to the intensity of intermediate stimulation zone 160 and, as such, has a contribution of 1.0. Electrodes 106A and 106C contribute less to the intensity of intermediate stimulation zone 160 then electrode 106B and thus have a value below 1.0. Electrode 106C contributes the least to the intensity of intermediate stimulation zone 160 as seen by the fact that it has the lowest numerical contribution value and as graphically indicated by the size of its associated field shape 156. Although referred to above as an intermediate stimulation zone, for the purposes of the example calculations below, stimulation zone 160 is considered a target stimulation zone.

Table 1 presented below depicts example steps that correspond to intermediate stimulation zones that may be associated with a transition from initial stimulation zone 142 of FIG. 21 to, target stimulation zone 160 of FIG. 22.

TABLE 1

| | | | | Steps | | | | | | | | | | End |
|---|---|---|---|---|---|---|---|---|---|---|---|---|---|---|
| Start | End | Diff | Size | 1 | 2 | 3 | 4 | 5 | 6 | 7 | 8 | 9 | | 10 |
| 1 | 0.6 | −0.4 | −0.04 | 0.96 | 0.92 | 0.88 | 0.84 | 0.8 | 0.76 | 0.72 | 0.68 | 0.64 | | 0.6 |
| 1 | 1 | 0 | 0 | 1 | 1 | 1 | 1 | 1 | 1 | 1 | 1 | 1 | | 1 |
| 0 | 0.2 | 0.2 | 0.02 | 0.02 | 0.04 | 0.06 | 0.08 | 0.1 | 0.12 | 0.14 | 0.16 | 0.18 | | 0.2 |

Column 1 of Table 1 (the left-most column) depicts the contributions of electrodes recruited to generate an initial stimulation zone, e.g., initial stimulation zone 142 of FIG. 21. As seen in column 1, only two electrodes have been recruited and each electrode contributes equally. This matches what is depicted graphically in FIG. 21.

Column 2 of Table 1 depicts the contributions of electrodes recruited to generate a target stimulation zone, e.g., target stimulation zone 160 of FIG. 22. As seen in column 2, three electrodes have been recruited, with contributions of 0.6, 1.0, and 0.2. This matches what is depicted graphically in FIG. 22.

Column 3 of Table 1 depicts the differences between the initial stimulation zone and the target stimulation zone, as determined by processor 53 of programmer 40, for example. In particular, processor 53 determines that there is a difference of −0.4, i.e., a decrease, in the contribution of electrode 106A, no difference in the contribution of electrode 106B, and a difference of 0.2, i.e., an increase, in the contribution of electrode 106C. Processor 53 divides each difference, whether an increase (stretch) as with electrode 106C or a decrease (shrink) as with electrode 106A, by the number of steps, e.g., ten, that processor 53 determines to be appropriate given the amount of change to the initial stimulation zone, the type of leads, the type of change (transverse stretch/shrink versus longitudinal stretch/shrink), as well as other factors, as shown in column 4. For example, processor 53 divides the −0.4 difference in contribution of electrode 106A by the number of steps, e.g., ten, and determines a step size of −0.04. Similarly, processor 53 divides the 0.2 difference in contribution of electrode 106C by the number of steps, e.g., ten, and determines a step size of 0.02. Processor 53 determined that there was no difference in the contribution of electrode 106B and, as such, the contribution of electrode 106B does not change from step 1 to step 10.

As mentioned above, in some examples, the step size is configurable by the user. Using options icon 212, a user may increase or decrease the step size or the number of steps (which changes the step size). As such, programmer 40 may automatically generate one or more intermediate stimulation zones based on transition from the initial stimulation zone to the target stimulation zone and based on a predetermined rate of change in stimulation amplitude. In other cases, the step size need not be the same for all steps in a sequence. Initial steps may be larger, with later steps (those nearer the likely discomfort threshold) being smaller to ensure comfort. In some examples, stimulator 34, or both programmer 40 and stimulator 34, may contribute to the generation of the one or more intermediate stimulation zones based on the initial and target stimulation zones.

In any of the examples provided herein, the rate of change used to generate the one of more intermediate stimulation zones may be used to determine one or more aspects of the intermediate stimulation zones. If the rate of change is predetermined, the rate of change may be a predetermined number of intermediate stimulation zones between the initial and target stimulation zone (similar to the example of Table 1), a predetermined step in amplitude between each zone in the transition (e.g., more intermediate stimulation zones for greater differences in amplitude between the initial and target stimulation zones), a predetermined time between each stimulation zone in the transition, or a predetermined number of electrodes that can be changed between each zone in the transition when the transition moves between different electrode configurations, or even a predetermined distance between zones of the transition. In other examples, the rate of change may be selected by the user to customize the transition between initial and target stimulation zones for particular patients.

Columns 5-14 (the right-most column) depict each of the ten steps and the contribution of each recruited electrode at a particular step. Each of the fixed number of steps, e.g., steps 1 through 10, of Table 1 represent an intermediate stimulation zone through which IMD 4, i.e., an electrical stimulator, may transition in order to transition from an initial stimulation zone to a target stimulation zone. As such, each of the one or more intermediate zones are defined by a respective set of stimulation parameters that are different than a respective set of stimulation parameters that define either the initial stimulation zone or the target stimulation zone.

Each of steps 1 through 10 of Table correspond to a respective indicator 232 on transition control unit 220 of FIG. 20. Using transition control input 220 in the manner described above with respect to FIG. 20, a user may transition initial stimulation zone 142 of FIG. 21 to target stimulation zone 160 of FIG. 22, for example, through one or more intermediate stimulation zones corresponding to a respective indicator 232. By providing one or more intermediate stimulation zones between an initial stimulation zone and a target stimulation zone, the rate of change of stimulation delivered to a patient may be limited in order to reduce or eliminate any discomfort that the patient may sense during the transition. In particular, by limiting the amount of change between intermediate stimulation zones, the overall rate of change of stimulation may be controlled.

In some examples, scroll wheel 200 may be available during a transition to modify the amplitude of stimulation of the stimulation zone currently being stretched (or shrunk). It may be desirable in other examples to disable the scroll wheel as either a global master amplitude control or as an individual electrode amplitude control. An example scroll wheel is described in detail in U.S. Provisional Application No. 61/330,160, entitled, "IMPLANTABLE MEDICAL DEVICE PROGRAMMING USING GESTURE-BASED CONTROL," and filed on Apr. 30, 2010, by Davis et al., the entire content of which is incorporated herein by reference.

It should be noted that, although only cathodal stimulation zones are described in detail in this disclosure, anodal shielding/guard zones may also be stretched, shrunk, or otherwise manipulated in the manner described throughout this disclosure. Both cathodes and anodes may be stretched/shrunk, although all such stretches/shrinks should obey balancing rules. For instance, stretching the only anode in use may also cause its amplitude to change, so as to keep the total anodal amplitude fixed.

As mentioned above, in some example implementations, it may be desirable to allow only one stimulation zone to be stretched/shrunk at a time. In other examples, however, it may be desirable to allow multiple zones to be stretched/shrunk at a time. For example, in one specific example configuration, it may be desirable to allow a user to stretch/shrink a cathodal stimulation zone on a first lead and stretch/shrink an anodal shield on a second lead. Manipulations to both a cathodal stimulation zone and an anodal shield may require processor 53 to perform balancing operations in order to ensure that the amount of current sunk by stimulation generator 60 equals the amount of current sourced by stimulation generator 60 so as deliver zero net charge to patient 6.

The example techniques described above generally describes stretches or shrinks to an initial stimulation zone. Using various techniques of this disclosure, initial stimulation zones may be shifted or moved to other positions within a lead configuration, as described below with respect to FIGS. 23-26. Shifting or moving the stimulation differs from the stretch or shrink techniques described above in that the shape of the one or more stimulation zones being shifted or moved may be retained at the target location. In other words, the target stimulation zones may have the same shape as the initial stimulation zones.

Figure 23:
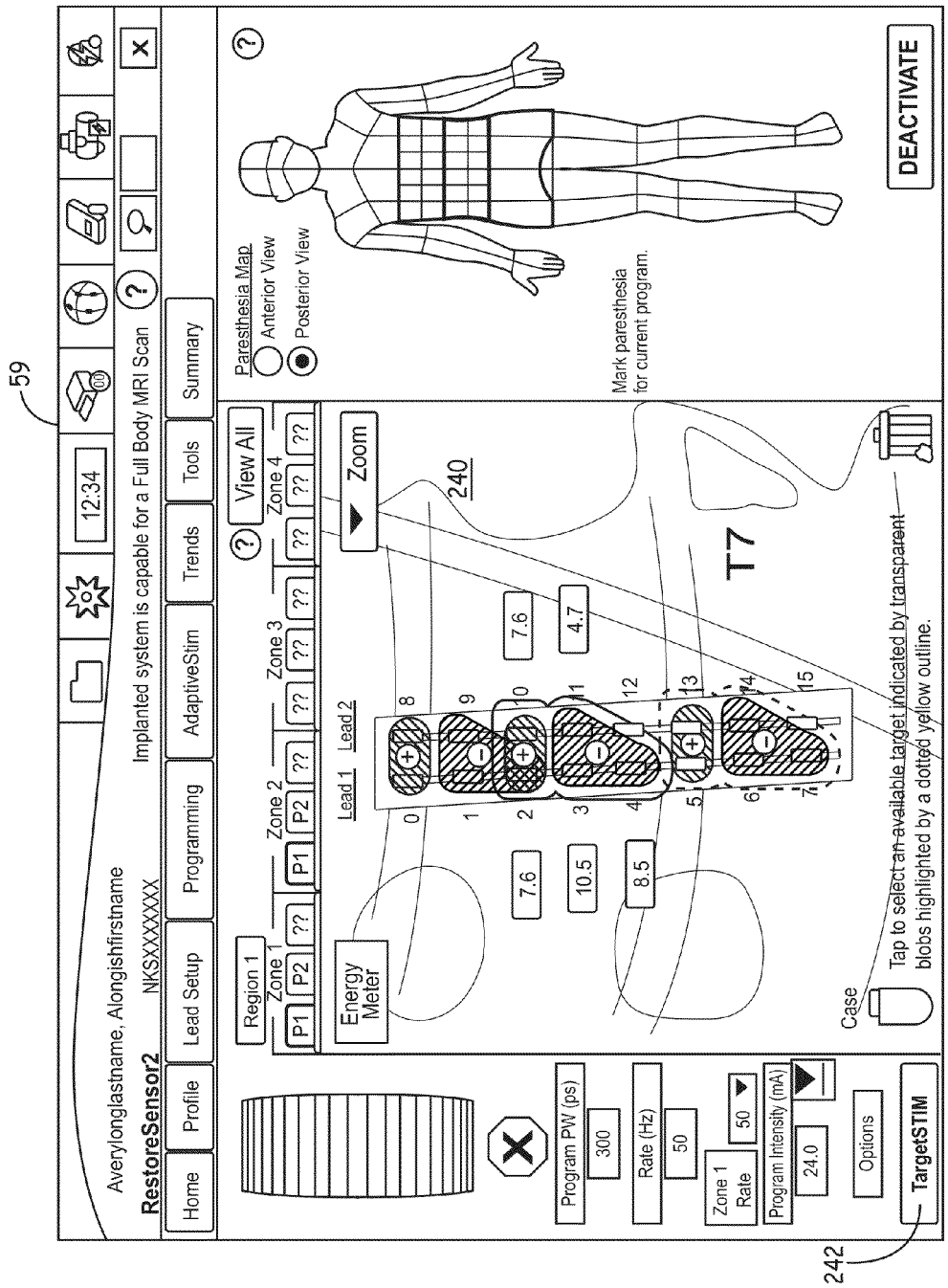
FIGS. 23-26 illustrate example programmer screens, in accordance with this disclosure.

FIGS. 23-26 illustrate example programmer screens, in accordance with this disclosure. FIGS. 23-26 are similar to the programmer screen described above with respect to FIG. 19 and may be used to transition one or more stimulation zones from an initial location to a target location. FIG. 23 depicts display window 240 which includes two leads, labeled "Lead 1" (the left-lead) and "Lead 2" (the right-lead), electrodes 0-7 of lead 1 (electrode 0 is the top-most electrode) and electrodes 8-15 of lead 2 (electrode 8 is the top-most electrode), as well as the case electrode (labeled "Case"). In addition, window 240 depicts two initial or actual zones. The first zone is an anodal zone generated by electrode 2 of lead 1 and electrode 10 of lead 2 sourcing current. The second zone is a cathodal zone generated by electrode 3 of lead 1, electrode 4 of lead 1, and electrode 11 of lead 2 sinking current. For the purposes of this disclosure, the first zone and the second zone are considered an initial stimulation zone and when transitioned together, as described below, the first and second zone form a target stimulation zone. Adjacent each of the five electrodes used to generate the first and second zones, display window 240 indicates the current associated with the electrode. In particular, electrode 2 of lead 1 sources 7.6 mA, electrode 10 of lead 2 sources 7.6 mA, electrode 3 of lead 1 sinks 10.5 mA, electrode 4 of lead 1 sinks 8.8 mA, and electrode 11 of lead 2 sinks 4.7 mA. Again, IMD 4 is currently delivering stimulation to patient 6.

FIG. 23 further depicts TARGETSTIM icon 242. A user may turn TARGETSTIM mode ON by tapping the TARGETSTIM icon or button once, for example. A second tap may turn TARGETSTIM mode OFF. Turning TARGETSTIM mode ON allows a user to modify, via programmer 40, the stimulation being delivered to patient 6. In particular, turning TARGETSTIM ON allows a user to select stimulation zones at locations up or down on one or more leads or between two or more leads.

When a user taps on or otherwise provides input to TARGETSTIM button 242 to enable the TARGETSTIM mode, programmer 40 displays a highlight, e.g., a yellow highlight, around button 242 and around all existing "stimulation" zones in the active stimulation program, and displays ghost or phantom "stimulation" zones with an outline, e.g., a yellow dotted outline, around available target stimulation zones. For simplicity, both anodal shield/guard zones and cathodal stimulation zones will be referred to as "stimulation" zones unless the distinction between the two becomes relevant. For example, although FIG. 23 displays one anodal guard zone and one cathodal stimulation zone, for simplicity, these zones will be referred to as two stimulation zones.

Figure 24:
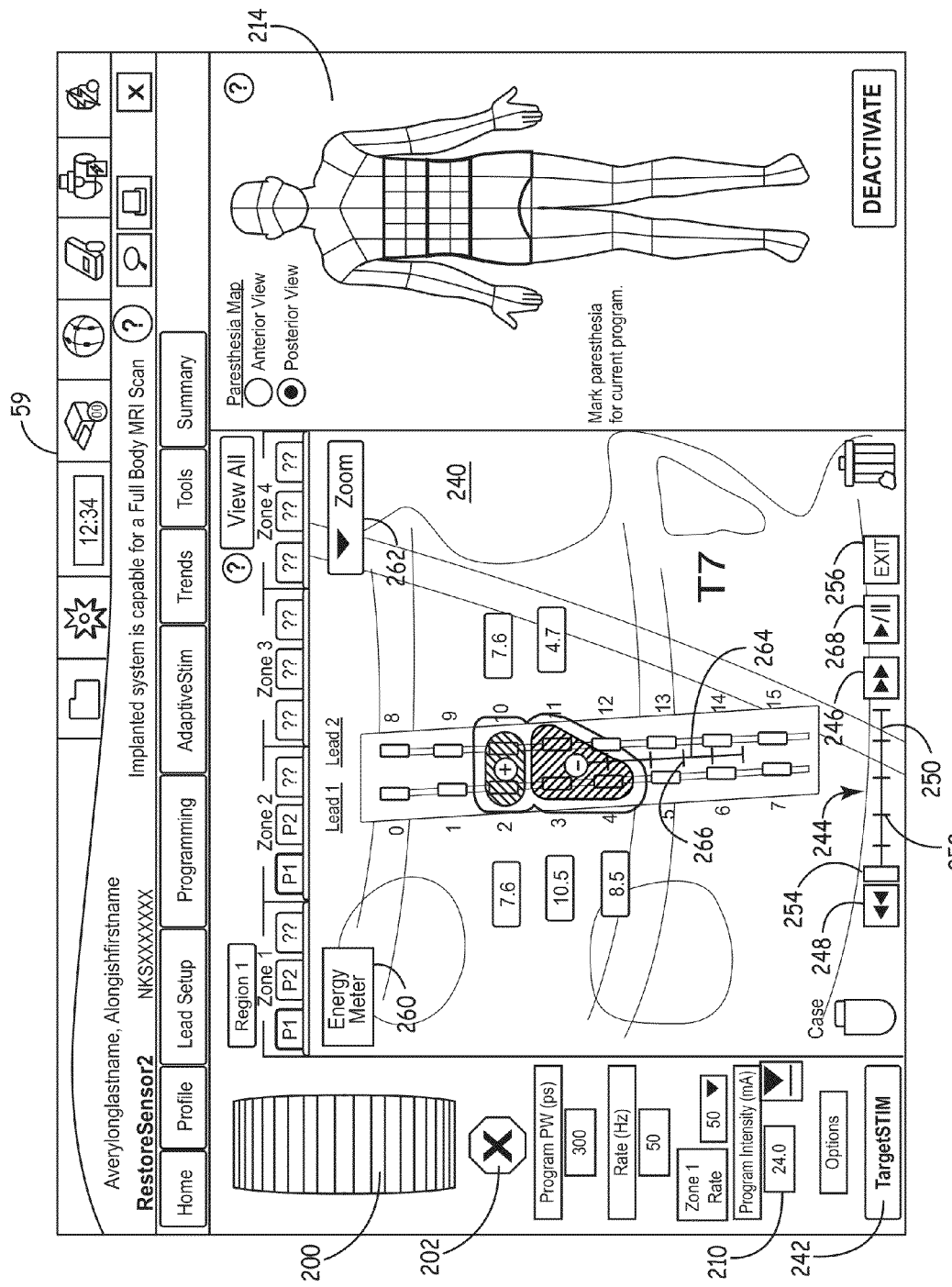

Available targets are defined by either the up, down, left, or right locations that the user can select for the existing stimulation zones. Programmer 40 may not display any available targets for locations at which the user cannot select the existing stimulation zones. For example, in FIG. 23, if locations to the left and right are not valid locations, programmer 40 does not display targets for these directions. In FIG. 23, programmer 40 may prevent a user from selecting a target stimulation zone such that the initial zone defined by electrodes 2 and 10 is transitioned to electrodes 7 and 15 because there are no remaining electrodes to create the stimulation zone defined by electrodes 3, 4, and 11. Thus, in FIG. 23, the furthest longitudinally "downward" position on lead 1 and lead 2 that a user could select as a target stimulation zone for the two stimulation zones corresponds to electrodes 5, 6, 7, 13, and 14. Similarly, the furthest longitudinally "upward" position on lead 1 and lead 2 that a user could select as a target stimulation zone for the two stimulation zones corresponds to electrodes 0, 1, 2, 8, and 9. Programmer 40 displays an outline around each of these two groups of five electrodes to indicate that they are available target stimulation zones. Other target stimulation zones are available including one defined by electrodes 1, 2, 3, 9, and 10, i.e., a location of one electrode upward. Likewise another target stimulation zone is available that is defined by electrodes 3, 4, 5, 11, and 12, i.e., a selection of a target stimulation zone of one electrode downward. Programmer 40 displays an outline around each of these target stimulation zones, as well as other available target stimulation zones. When a user selects one of the available target stimulation zones, programmer 40 displays a transition control input, as seen in FIG. 24.

In order to select one of the available target stimulation zones, a user may, for example, tap anywhere within the target stimulation zone. In this manner, a user may provide input to programmer 40 that defines a target stimulation zone by selecting from one or more available target stimulation zones. If the target stimulation zones are covered, i.e., graphically overlap on the representation in display window 240, by the existing stimulation zones, as in FIG. 23, tapping on the existing stimulation zones may not select the target. Instead, the user may tap outside of the existing stimulation zone but within the target stimulation zones to make a selection. Once the user taps to select the target, programmer 40 may remove the ghost or phantom stimulation zones. To re-enable the display of the available target ghost stimulation zones, the user may exit and reenter TARGETSTIM mode.

In some examples, programmer 40 may not respond if a user taps on existing stimulation zones or within the highlight around the stimulation. Once the user taps on an available target stimulation zone, a path that the TARGETSTIM will traverse to transition the initial stimulation is displayed with indications of the steps between the initial and target locations, as seen in FIG. 24. In some examples, the transition from the initial stimulation zone to the target stimulation zone via one or more intermediate stimulation zones does not occur until a user has initiated the transition using the transition control input of FIG. 24.

In other examples, the user may stretch or shrink existing stimulation zones to a new target stimulation zone without providing dotted lines around the original electrodes. For example, different colors may distinguish between existing and target stimulation zones. Alternatively, the stimulation zone (or control shape) may be stretched or shrunk by the user to the new target stimulation zone and the transitions between the existing electrode contributions and the new electrode contributions may be illustrated by changing sizes of field shapes over each electrode. Once an electrode no longer contributes to the delivered stimulation, the stimulation zone may change to exclude that electrode.

FIG. 24 depicts display window 240 of FIG. 23 after a user has selected one of the available target stimulation zones. Once a user has selected one of the available target stimulation zones, programmer 40 displays or otherwise enables transition control input 244. Transition control input 244 operates in a manner that is substantially similar to transition control input 220 described above with respect to FIG. 20. As seen in FIG. 24, transition control input 244 shows a "forward" input 246 and a "rewind" input 248. Transition control input 244 may be a slider bar, e.g., slider bar 250, which includes indicators 252. Like transition control input 220 of FIG. 20, a user may slide slider thumb 254 (also referred to as a "slider") which may be moved to various indicators 252 along slider bar 250. Each indicator 252 corresponds to a step corresponding to an intermediate stimulation zone between the initial or actual stimulation zone(s), e.g., the two zones depicted in FIG. 23, and the target stimulation zones selected by the user.

Once the user taps on the target stimulation zone, programmer 40 displays path 264 that the initial stimulation zone will traverse, along with one or more indicators between the initial location and target location, shown as indicators 266. The indicators 252 on slider bar 250 correspond to indicators 266 on path 264. That is, each movement of slider thumb 254 by one indicator 252 corresponds to one step on path 264.

A user may tap either forward input 246 or rewind input 248 once, which causes programmer 40 to transition the stimulation zones one step forward or one step backward, respectively. Both forward input 246 and rewind input 248 may be step-wise in that they step in a controlled fashion through one or more intermediate stimulation zones. In this manner, after receiving user input indicating a target stimulation zone, programmer 40 may control a transition from an initial stimulation zone to the target stimulation zone through one or more intermediate stimulation zones corresponding to a respective indicator 266 on path 264. By providing one or more intermediate stimulation zones between an initial stimulation zone and a target stimulation zone, the rate of change of stimulation delivered to a patient may be limited in order to reduce or eliminate any discomfort that the patient may sense during the transition. In particular, by limiting the amount of change between intermediate stimulation zones, the overall rate of change of stimulation may be controlled.

In some examples, when slider thumb 254 is on a leftmost indicator 252, rewind input 248 is disabled. Similarly, when slider thumb 254 is on a rightmost indicator 252, forward input 246 is disabled. Each tap on forward input 246 (when available) may move slider thumb 254 by one position to the right, and each tap on rewind input 248 (when available) may move slider thumb 254 by one position to the left. In addition, in some examples, each tap on the forward or the rewind inputs (when available) may also update the position of the existing stimulation zones on path 264 to reflect the new position of slider thumb 254. It should be noted that, in some example implementations, even after receiving a tap to select a position, programmer 40 may require that the user press or click PLAY/PAUSE button 268 to apply stimulation at the selected position, rather than immediately applying stimulation at the selected position in response to the user's selection of the position.

The user may tap and hold slider thumb 254 and drag it either forward (if not at the target) or backward (if not at origin). If the user taps and drags slider thumb 254, then programmer 40 enables PLAY/PAUSE button 268. In some examples, after dragging slider thumb 254, the user may press PLAY/PAUSE button 268, which moves slider thumb 254 by one step, i.e., one indicator, incrementally until the user pauses the transition, exits the TARGETSTIM mode, or until slider thumb 254 reaches its destination, i.e., the target stimulation zone. If the user pauses the transition, exits the TARGETSTIM mode, or slider thumb 254 reaches its destination, then programmer 40 displays the stimulation zone at the position corresponding to the position at which slider thumb 254 was located when the user or system terminated the transition.

When the user drags slider thumb 254 and taps PLAY/PAUSE button 268 to initiate the transitioning of the stimulation zones, the stimulation zone may transition toward the target stimulation zone at a predetermined pace. In some examples with multiple stimulation zones, e.g., as in FIGS. 23-26, the stimulation zones may transition toward the target stimulation zone sequentially (not smoothly or continuously) and follow each intermediate step between the starting point that the slider was dragged from and the target point, depending on how far the slider was dragged.

For example, a first stimulation zone, e.g., the stimulation zone defined by electrodes 3, 4, and 11 in FIG. 24, may transition first, followed by a transition of a second stimulation zone, e.g., the stimulation zone defined by electrodes 2 and 10 in FIG. 24, followed by another transition of the first stimulation zone, then by another transition of the second stimulation zone, and so forth. Conceptually, this sequential transition of zones may be thought of as an inchworm type of movement.

In other examples, a first one of the two or more stimulation zones may be transitioned once, then both stimulation zones may be transitioned together, then the first stimulation zone may be transitioned once again, then both stimulation zones may be transitioned together, and so forth until the last transition, at which time the remaining stimulation zones are transitioned once to "catch up" to the first stimulation zone. Regardless of the technique used, the goal is for the final shape of the two or more stimulation zones to match the initial shape of the multiple stimulation zones, but be relocated to one or more different electrodes.

It should be noted that while the examples above describe both the anodal shield/guard zone and the cathodal stimulation zone as being moved together, in other example implementations, anodal shield/guard zone(s) and cathodal stimulation zone(s) may be moved independently of one another. For example, a user may select the anodal shield/guard zone defined by electrodes 2 and 10 as the initial stimulation zone and programmer 40 may display a number of available target stimulation zones along leads 1 and 2. After a user selects a target stimulation zone to which the anodal shield/guard zone initially defined by electrodes 2 and 10 will transition, the user may select the cathodal stimulation zone defined by electrodes 3, 4, and 11. Then, based on the target stimulation zone that the user selected for the anodal shield/guard zone initially defined by electrodes 2 and 10, programmer 40 displays available target stimulation zones along leads 1 and 2 to which the cathodal stimulation zone initially defined by electrodes 3, 4, and 11 may transition. Programmer 40 may prevent the user from selecting a target stimulation zone for the cathodal stimulation zone that would overlap with the target stimulation zone that the user selected for the anodal shield/guard zone initially defined by electrodes 2 and 10. Once the user has finished selecting target stimulation zones, the user may initiate the transition from the initial stimulation zones to the target stimulation zones via one or more intermediate stimulation zones using the transition control input of FIG. 24. Of course, this is just one example of how anodal shield/guard zone(s) and cathodal stimulation zone(s) may be moved independently of one another. Numerous other example implementations are possible and considered to be within the scope of this disclosure.

Allowing anodal shield/guard zone(s) and cathodal stimulation zone(s) to be moved independently of one another may allow the relative position of one zone, e.g., an anodal shield/guard zone, to be changed relative to another zone, e.g., cathodal stimulation zone. For example, in FIG. 23, a user may change the position of the anodal shield/guard zone from electrodes 2 and 10 to electrodes 0 and 8 without changing the position of the cathodal stimulation zone defined by electrodes 3, 4, and 11. Similarly, user may change the position of the cathodal stimulation zone from electrodes 3, 4, and 11 to electrodes 6, 7, and 14 without changing the position of the anodal shield/guard zone defined by electrodes 2 and 10. These are just two examples of how the relative positions of anodal shield/guard zone(s) and cathodal stimulation zone(s) may be changed using the techniques of this disclosure.

In addition to independently moving anodal shield/guard zone(s) and cathodal stimulation zone(s), the shape and/or size of the anodal shield/guard zone(s) and cathodal stimulation zone(s) may be changed independently of one another, e.g., via stretching and shrinking, using the techniques described throughout this disclosure.

Slider thumb 254 updates its position as the stimulation zones transition between the two end points on path 264 as identified from the drag action by the user on slider bar 250. The position of slider thumb 254 corresponds to a position along path 264. To stop the sequential transition of stimulation zones along path 264, the user may tap on a point on path 264, e.g., on one of indicators 266 along path 264 or between indicators 266, where the user wants to stop on slider bar 250. In other words, user input along path 264 may control activity on slider bar 250.

In some example implementations, programmer 40 may prevent the user from exiting TARGETSTIM mode when the stimulation zones are moving sequentially based on user input. In such an example, the user may need to stop stimulation zone transition before programmer 40 allows the user to exit TARGETSTIM mode. If the user exits TARGETSTIM mode in an allowed manner, the highlight, e.g., a yellow highlight, around the TARGETSTIM button 242 and around the stimulation zones in the program are removed and, if no changes are pending, then programmer 40 enables various navigation tabs and other buttons on the screen.

In some example implementations, exiting TARGETSTIM mode leaves the stimulation zones at the position they were at immediately prior to the user exiting TARGETSTIM mode. In addition, any paresthesia marked by the user on paresthesia map 214 is visible after exiting TARGETSTIM mode.

In other example implementations, programmer 40 prevents the user from increasing or decreasing the stimulation intensity when the sequential stimulation zone transition is in progress. However, if there is no stimulation zone transition, the user may tap on program intensity input 210 to select it, which causes programmer 40 to enable scroll wheel 200. In some examples, programmer 40 may display a highlight around scroll wheel 200 and program intensity input 210 if enabled.

After a user selects a target stimulation zone, the user may also tap EXIT button 256 to exit the TARGETSTIM mode. Tapping on EXIT button 256 may exit the TARGETSTIM mode and leave the program in the state it was when the user tapped on the EXIT button. In other words, any TARGETSTIM transitions occurring are terminated and the stimulation zones snap to the TARGETSTIM position associated with stimulation zones at the time of the termination. In addition, on exiting the TARGETSTIM mode, programmer 40 may no longer display or may otherwise disable the available target stimulation zones (if visible) or the transition control input including the forward button, reverse button, and exit button.

In some example implementations, TARGETSTIM mode may be available only when the program is "Active, Valid and On" and when no parameter ramp is in progress. In other example implementations, when in TARGETSTIM mode, the user may not be able to navigate away from the programming panel. In another example implementation, when in TARGETSTIM mode, only program intensity input 210 is available to the user. The user may, for example, tap to select program intensity input 210, and then use scroll wheel 200 to change intensity. In addition, paresthesia map 214 may be available for user input while in TARGETSTIM mode. Further, energy meter 260 may, in some example implementations, be disabled while programmer 40 is in TARGETSTIM mode. The energy meter 260, when selected, gives an indication of the relative or absolute energy usage of the current settings. For high energy settings, it might indicate that the device would last 3 days between recharge, for example. For lower use settings, it might indicate that the device would last a week or more. Zoom tool 262 may be enabled during TARGETSTIM mode. It should be noted that when the user has selected the TARGETSTIM mode, help text may be displayed to the user.

Figure 25:
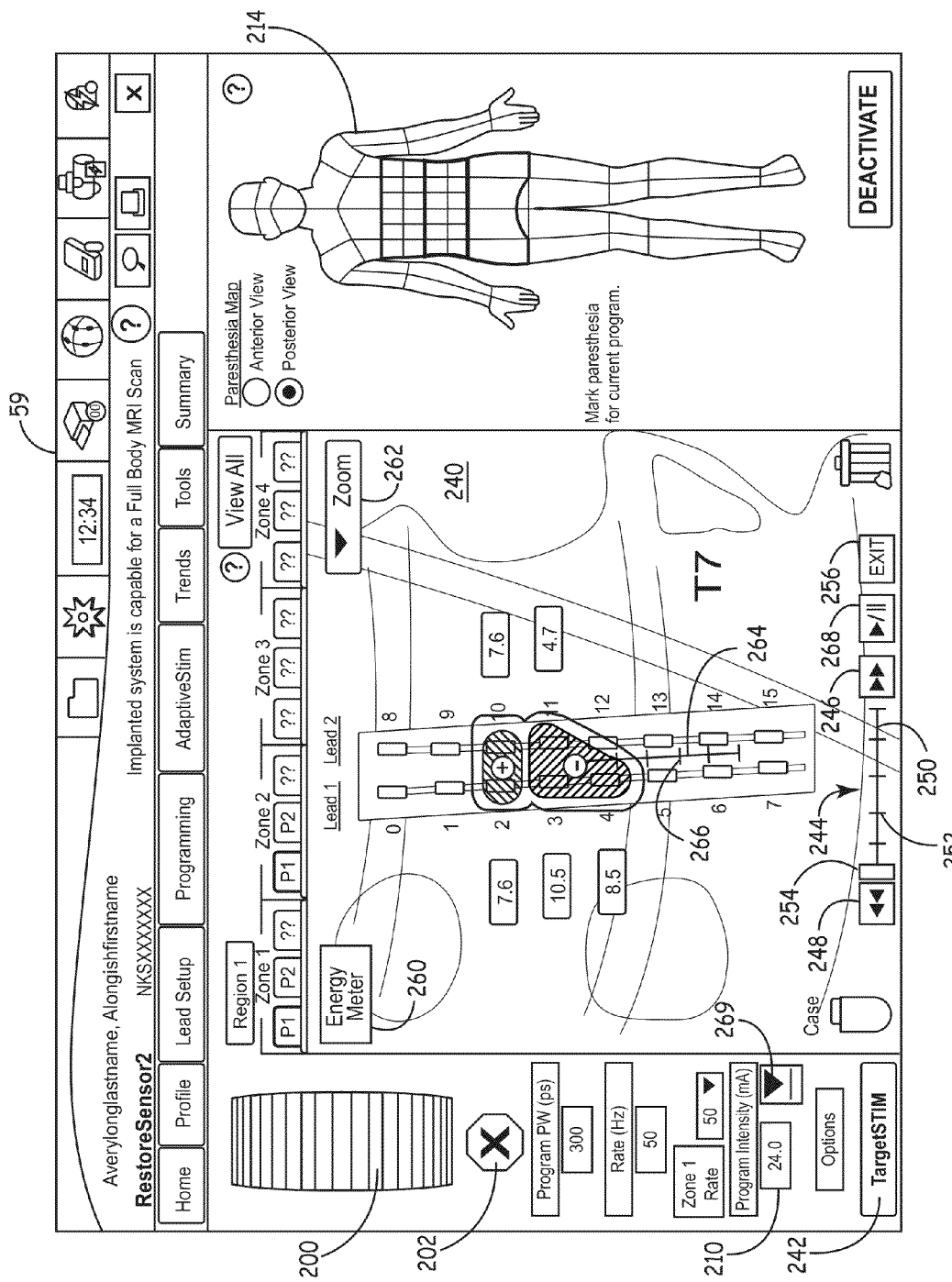

Referring now to FIG. 25, when program intensity input 210 is selected or when the intensity ramp caused by user input to scroll wheel 200 is in progress, programmer 40 may prevent the user from moving the stimulation zones forward or backward. Programmer 40 may disable transition control 244 during an intensity ramp and display it as being "greyed out" to the user. In order to re-enable transition control 244, the user may tap zero down control icon 269 (shown adjacent to the program intensity control 210) or STOP icon 202 to either zero out the amplitude or stop the amplitude ramp and deselect program intensity input 210. Zero down control icon 269 immediately sets amplitude to 0 for this zone such that stimulation ceases.

Figure 26:
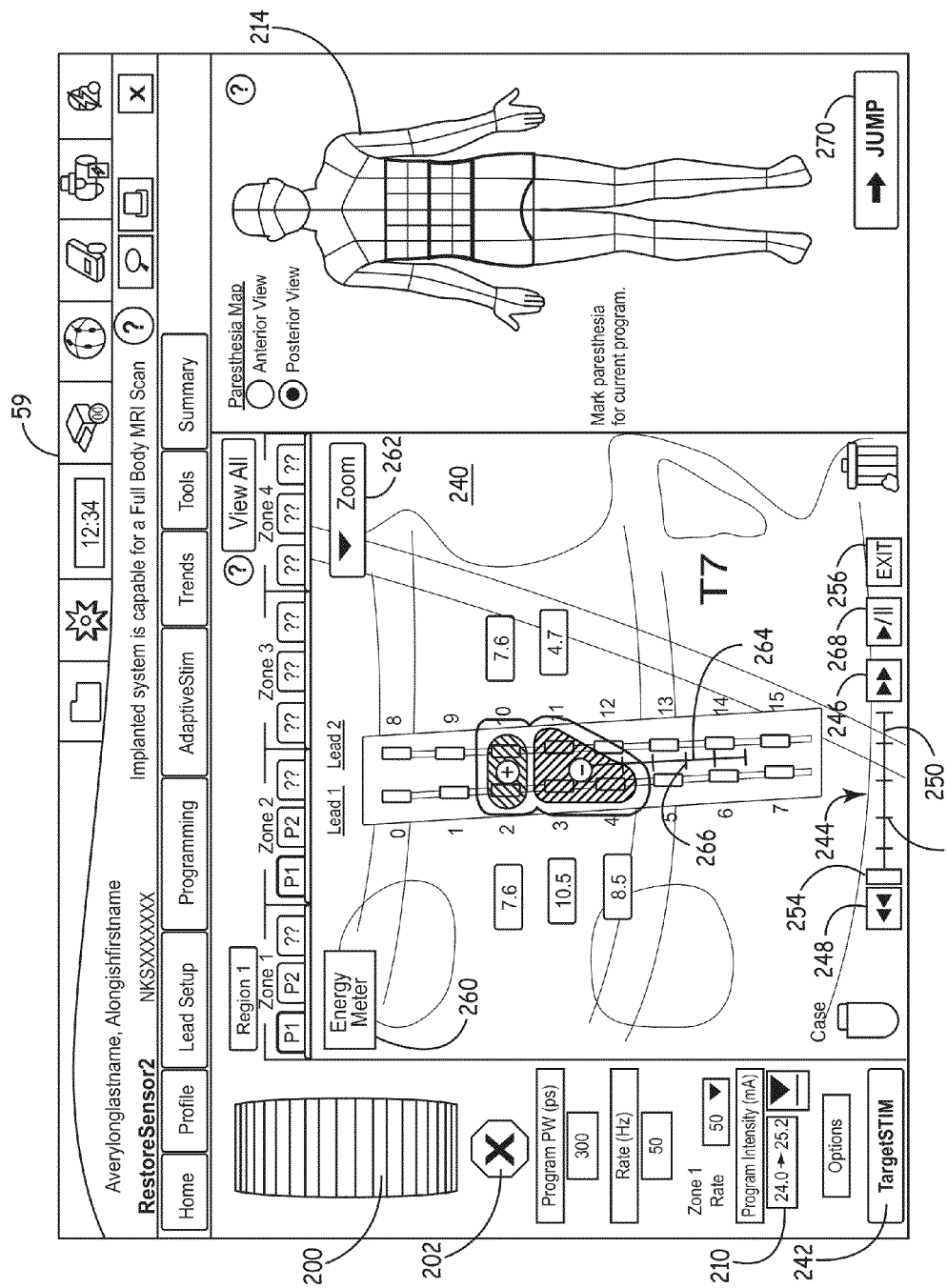

Referring now to FIG. 26, while the intensity ramp is in progress (caused by user input to scroll wheel 200), tapping STOP icon 202 will stop the intensity ramp, and pressing "→Jump" button 270 jumps the stimulation intensity to the target intensity value. For example, in FIG. 26, program intensity input 210 indicates that the current intensity value is 24.0 mA and the target intensity value is 25.2. A user may select STOP icon 202 to stop the ramp increase from 24.0 mA to 25.2 mA and select "→Jump" button 270. In response, programmer 40 controls IMD 4 to apply 25.2 mA immediately rather than continue the intensity ramp.

Although window 240 in FIGS. 23-26 illustrates leads and stimulation zones overlaid on an image of patient anatomy, the patient anatomy may not be shown in other examples. The representation of patient anatomy derived from an imaging modality (e.g., fluoroscopy, MRI, x-ray, or computed tomography) may be removed by the user or otherwise not presented, such as shown in FIGS. 32-36.

Figure 27:
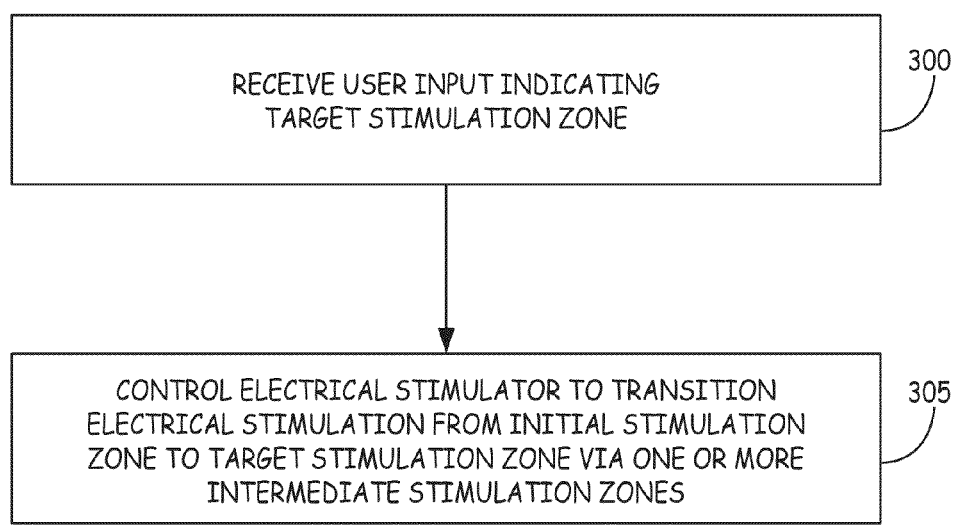
FIG. 27 is a flowchart illustrating an example method for performing the techniques of this disclosure.

FIG. 27 is a flowchart illustrating an example method for performing the techniques of this disclosure. A programmer for an electrical stimulator, e.g., programmer 40, receives user input indicating a target stimulation zone (300). In response, the programmer controls the electrical stimulator, e.g., IMD 4, to transition electrical stimulation from an initial stimulation zone to the target stimulation zone via one or more intermediate stimulation zones (305).

For example. IMD 4 delivers electrical stimulation to patient 6 via an initial stimulation zone 142, as seen in FIG. 14. Then, programmer 40 receives input from a user to transition stimulation from initial stimulation zone 142 to a target stimulation zone 150 as seen in FIG. 15. In response, programmer 40 controls IMD 4 to transition electrical stimulation from initial stimulation zone 140 to target stimulation zone 150 via one or more intermediate stimulation zones, as seen and described above with respect to FIGS. 17 and 18 and Table 1, for example.

As another example, IMD 4 delivers electrical stimulation to patient 6 via an initial stimulation zone comprising two stimulation zones, as seen in FIG. 23. Then, programmer 40 receives input from a user to transition stimulation from the initial stimulation zone of FIG. 23 to one of the target stimulation zones shown in FIG. 23. In response, programmer 40 controls IMD 4 to transition electrical stimulation from the initial stimulation zone to the target stimulation zone, e.g., along a path, via one or more intermediate stimulation zones, as seen in FIG. 24. Thus, programmer 40 may control a transition that results from user stretches, shrinks, or other manipulations, programmer 40 may control a transition that results from movement along a path. Although programmer 40 may automatically generate the one or more intermediate stimulation zones, stimulator 34, or a combination of programmer 40 and stimulator 34, may automatically generate the one or more intermediate stimulation zones.

By controlling the electrical stimulator to transition electrical stimulation from an initial stimulation zone to the target stimulation zone via one or more intermediate stimulation zones, the rate of change of stimulation may be limited. In this manner, sudden jumps in stimulation amplitude or location are avoided, which may be uncomfortable or disconcerting to a patient receiving stimulation therapy.

In some examples, the method shown in FIG. 27 may include graphically displaying the transition from the initial stimulation zone to the target stimulation zone, as seen in FIGS. 14-18, for example. In other examples, the method may include displaying, via the programmer, a transition control input comprising one or more indicators, each of the one or more indicators corresponding to a respective one of the one or more intermediate stimulation zones. As described above, the one or more indicators are either linearly or non-linearly related to one another. In addition, in some examples, the number of indicators on the transition control input may be based on the user input indicating a target stimulation zone. So, for large changes, e.g., a large stretch or shrink, programmer 40 may display more indicators than for small changes. It should be noted, however, that in some example implementations. programmer 40 might not display the indicators to the user. That is, the indicators may be used by programmer 40 but not visible to the user.

In other examples, programmer 40 receives user input that initiates a transition from an initial stimulation zone to a target stimulation zone via the transition control input, e.g., transition control input 220 of FIG. 20 or transition control input 244 of FIG. 24. In such an example, the transition control input may receive user input via an initiate input, e.g., PLAY button 226 of FIG. 20 or PLAY button 268 of FIG. 24. In some examples, the transition control input may comprises a slider bar, e.g., slider bar 230 of FIG. 20 or slider bar 250 of FIG. 24.

In other examples, the method may also include graphically dragging a slider on the slider bar from a first indicator of the one or more indicators to a second indicator of the one or more indicators, wherein controlling the electrical stimulator to transition electrical stimulation from an initial stimulation zone to the target stimulation zone via one or more intermediate stimulation zones comprises controlling the electrical stimulator to transition electrical stimulation from the initial stimulation zone to the target stimulation zone from the first indicator to the second indicator via any intermediate indicators.

In some examples, the transition control input comprises an increment input, e.g., increment input 224 of FIG. 20 or forward input 246 of FIG. 24, and a decrement input, e.g., decrement input 222 of FIG. 20 or rewind input 248 of FIG. 24. In such an implementation, the method may further comprise receiving user input via the increment input or the decrement input, wherein the increment input controls the electrical stimulator to transition the initial stimulation zone stepwise toward the target stimulation zone through one of the one or more intermediate stimulation zones, and wherein the decrement input controls the electrical stimulator to transition the initial stimulation zone stepwise away from the target stimulation zone through one of the one or more intermediate stimulation zones.

In one example, the one or more intermediate stimulation zones are automatically generated based on the initial stimulation zone to the target stimulation zone and based on a predetermined rate of change in stimulation amplitude.

In another example, the method includes receiving user input via the programmer that graphically defines the target stimulation zone. In such an example, the user input may graphically manipulate, e.g., stretch or shrink, at least one of a shape and a location of the initial stimulation zone in order to define the target stimulation zone.

In some examples, IMD 4 continues to deliver electrical stimulation to patient 6 during the transition from the initial stimulation zone to the target stimulation zone, thus prevent the need to ramp the intensity up after the transition.

Figure 28:
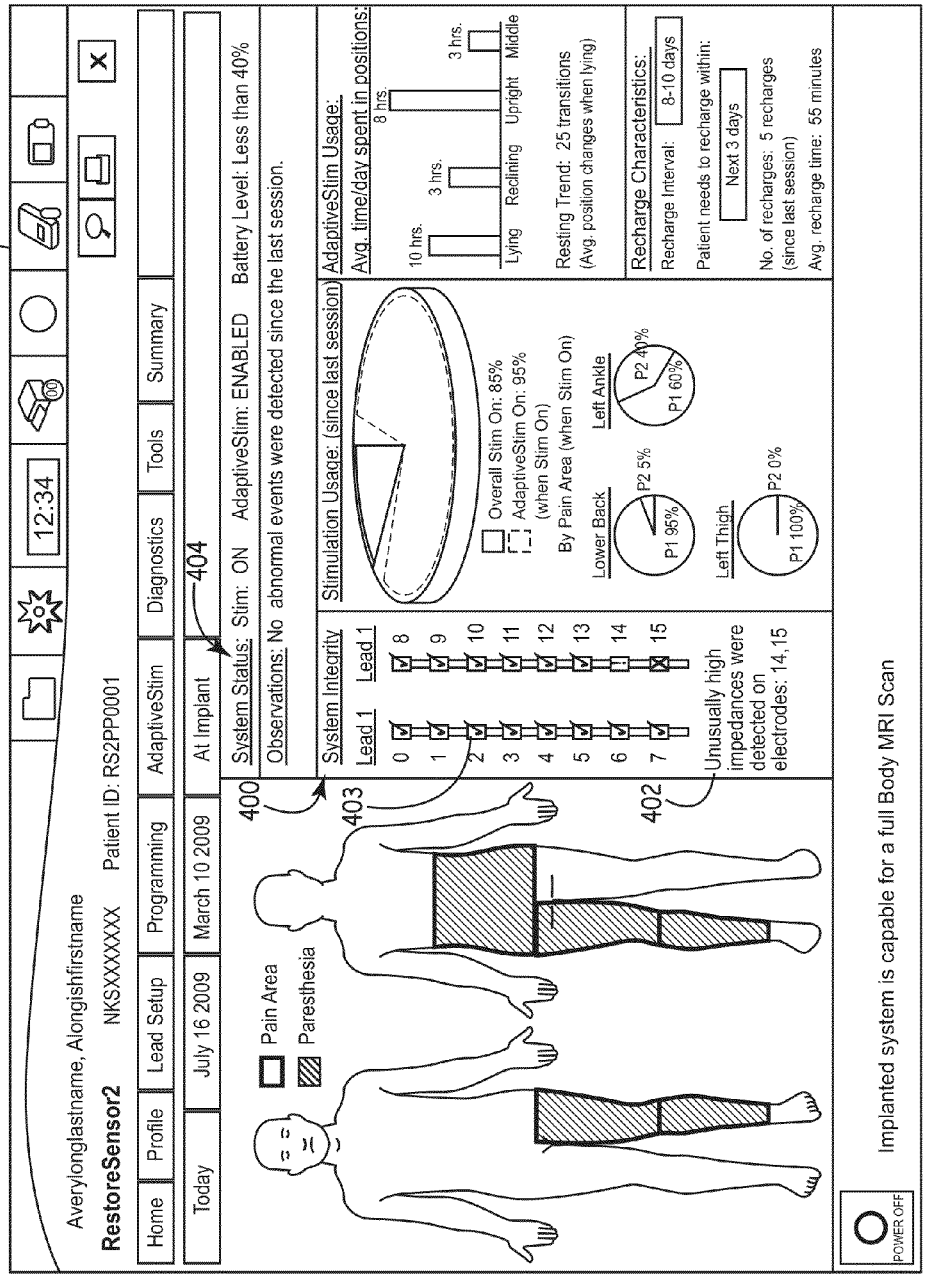
FIG. 28 illustrates another example programmer screen, in accordance with this disclosure.
Figure 29:
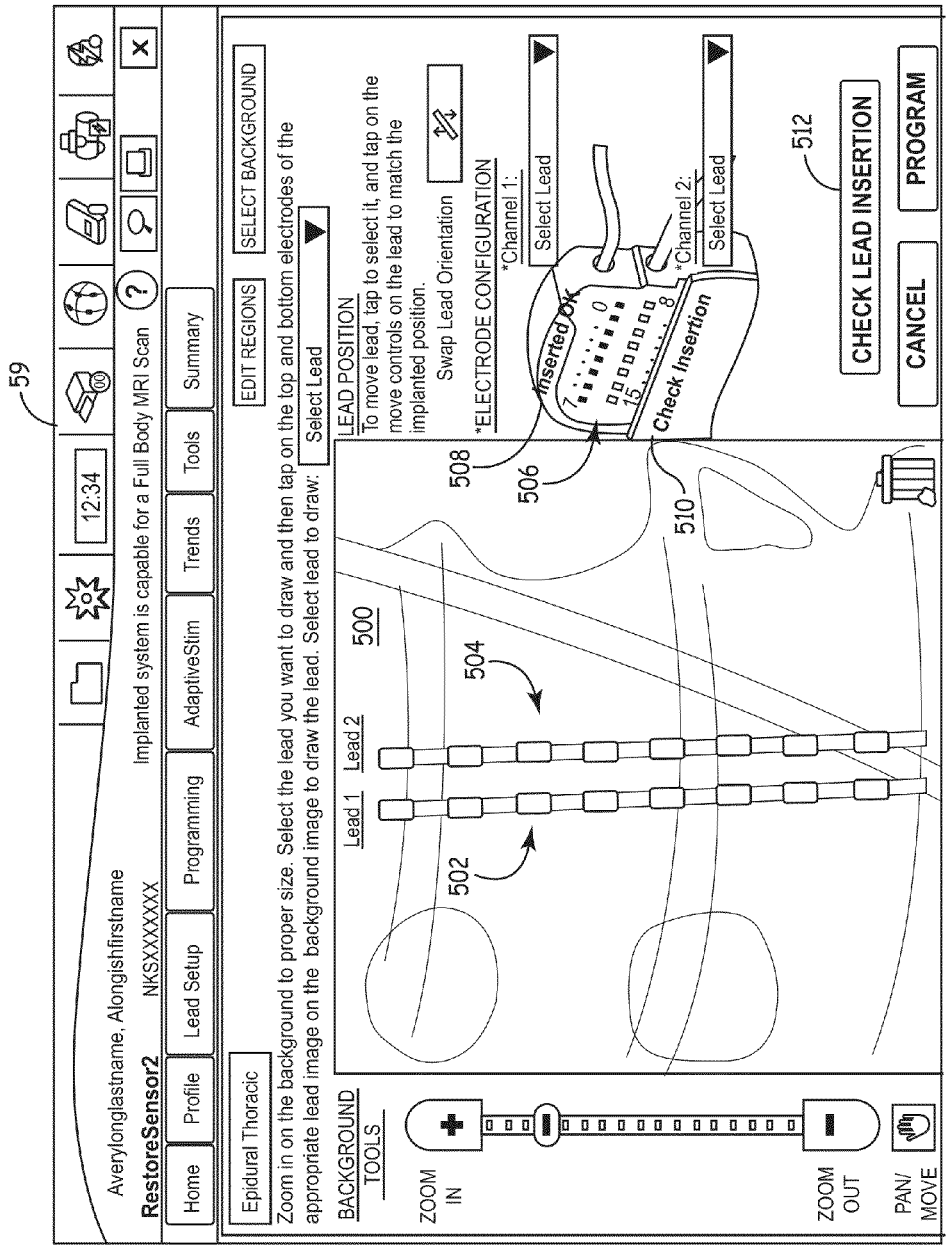
FIG. 29 illustrates another example programmer screen, in accordance with this disclosure.

During trialing procedures where temporary leads are placed to test stimulation effectiveness, or during procedures to place leads and implantable devices more permanently, connectivity between the implanted device and each electrode of a lead may be continuously tested in real-time. FIGS. 28 and 29, described below, depict various programmer screens that graphically display the results of impedance measurements, in accordance with certain techniques of this disclosure.

FIG. 28 illustrates another example programmer screen, in accordance with this disclosure. In FIG. 28, a system integrity feature, shown generally at 400, graphically displays the results of an impedance measurement performed on the electrodes of two implanted leads, namely Lead 1 and Lead 2. The display shown at 400 in FIG. 28 provides a simplified, color-coded, graphical indication of impedance measurements to the user. In FIG. 28, for example, an interrogation automatically performed on the implanted device determined that the impedances of electrodes 0-7 on Lead 1 and electrodes 8-13 on Lead 2 were within an acceptable range and, as such, programmer 40, for example, colored the graphical representation of electrodes 0-7 and 8-13 green to indicate that the impedance of these electrodes were within a predetermined range of values, e.g., between 0 and about 3,000 ohms, and thus "passed" the impedance test. The representation of electrode 14 of FIG. 28 is colored yellow to indicate that there may be a problem with the electrode based on a higher-than-normal impedance measurement, e.g., between about 3,000 ohms and about 40,000 ohms, but it is likely still functioning. The representation of electrode 15 of FIG. 28 is colored red to indicate that the impedance of electrode 15 was high enough to be considered an open circuit condition based on a very high impedance measurement, e.g., above about 40,000 ohms, thus it is likely not functioning.

As shown at 402, programmer 40 may also display an indication, via text, with respect to electrodes that are suspect or that fail the impedance test. The text may indicate that unusually high impedances were detected and for which electrodes the high impedance was detected. In some example implementations, programmer 40 may prevent a user, e.g., a clinician, from selecting the non-functioning electrodes, e.g., electrodes that are colored red, for use in delivering therapy to a patient. Although not depicted in FIG. 28, the results of the impedance measurements, in ohms, may be displayed next to the colored representation of each electrode. For example, in some example implementations, a user may "check" one or more of the electrode representations, as seen at 403, and programmer 40 will not display the actual impedance measurements. Or, in other example implementations, a user may "check" one or more of the electrode representations and programmer 40 will display the actual impedance measurement.

The colored, graphical representation of the results of electrode impedance measurements may allow a user to quickly determine whether the implanted leads have been completely inserted within a header of IMD 16, for example, without having to remember whether a specific impedance measurement value falls within an acceptable range. For example, using these graphical techniques, a user need not remember that an impedance value of 6,000 ohms may indicate that the electrode is suspect because the programmer colors an electrode with an impedance measurement of 6,000 ohms yellow to graphically indicate that the electrode may be suspect.

The system integrity results shown generally at 400 in FIG. 28 may represent the results of a unipolar impedance test. During a unipolar impedance test, an impedance measurement may be taken between a housing (or can) electrode, e.g., electrode 13 of FIG. 1, and each electrode on each lead, e.g., each electrode 11 on each lead 12A, 12B of FIG. 1. Using certain techniques of this disclosure, the results of the unipolar impedance test may be graphically displayed to the user using a color-coded strategy, as described above. In addition, in some example implementations, the unipolar impedance test may be performed automatically upon interrogation of the implanted device. It should be noted that the colors green, yellow, and red are only one implementation.

In other examples, impedance testing may be performed via bipolar impedance testing. For example, bipolar impedance testing may be performed in one or more groups of electrodes in order to determine integrity of the tested electrode combinations. In a group of four electrodes, for example, four possible bipolar combinations of electrodes (e.g., 1 and 2, 2 and 3, 3 and 4, and 4 and 1) are tested to determine any problems or issues with one of the tested electrodes. A similar test may be reproduced in any combination or configuration for additional electrodes (e.g., unipolar, bipolar, odd numbers of electrodes, or even numbers of electrodes) in a similarly size group of electrodes. In this manner, the results of impedance testing may be achieved using various techniques other than unipolar electrode testing. Other implementations contemplated by this disclosure include other color combinations. In some implementations, only suspect or failing electrodes are color coded, while electrodes that pass the impedance test are not colored.

Still referring to FIG. 28, a "System Status" area, shown generally at 404, may display a status with respect to the impedance test that was performed (not shown). For example, if all of the electrodes passed the test, System Status area 404 may display text indicating a passing status, such as "Impedance: OK" or "Impedance: PASS," for example. In other examples, such as that displayed in FIG. 28 where two electrodes, namely electrodes 14 and 15 of Lead 2, either were flagged as suspect or as failing electrodes, System Status area 404 may display text indicating that a user should run a complete impedance test, such as "Impedance: RUN FULL TEST," for example, and also display or enable a button that a user may press to initiate a full impedance test, rather than a simplified unipolar impedance test, as described in more detail below. Or, even if one or more electrodes fail or are suspect, a user may choose not to run a full test if the particular stimulation program(s) that will be used do not utilize the suspect or failing electrodes, e.g., electrodes 14 and 15 of FIG. 28. In some examples, System Status area 404 may display text indicating that the unipolar impedance test could not be performed, such as "Impedance: COULD NOT PERFORM TEST," for example, if there was a problem with the measurement.

As mentioned above, a user may perform a more complete, or full, impedance test on the electrodes if one or more electrodes are flagged as failing or suspect. Of course, the user may also run a full impedance test even if all the electrodes are indicated as passing the unipolar impedance test. After a user presses or touches a button on the display shown in FIG. 28 to run a full impedance test, programmer 40 may open another display panel (not shown), such as a "TOOLS" display panel. A full impedance test may be a bipolar impedance test. During a bipolar impedance test, an impedance measurement may be taken between a first electrode and all other electrodes on the implanted leads, between a second electrode and all other electrodes on the implanted leads, and so forth until all electrode pairs are tested. While the full impedance test is being performed, the color coding of electrodes that resulted from the unipolar impedance test might not be displayed because programmer 40 may be waiting to display the results of the full impedance test. In some examples, a check box may be displayed next to each lead and/or each electrode to allow the user to select whether an actual impedance measurement, in ohms, should also be displayed along with the color-coded results of the full impedance test.

In addition, the TOOLS display panel (not shown) may also include additional details about the measurements. displayed in a text format. By way of specific example, if electrode 14 was determined to be suspect, as shown in FIG. 28, and a full impedance test is run, programmer 40 may display text in the TOOLS display panel indicating, for example, that an impedance of 6,000 ohms was detected between electrode 14 and electrodes 8, 9, and 10. The user may then determine from this text that it is likely that electrodes 8, 9, 10, and 14 are shorted.

As mentioned above, a full impedance test may determine the impedance between every pair of electrodes on the implanted lead(s). As such, the full impedance test (e.g., a bipolar impedance test) may take longer to complete than a unipolar test. In accordance with this disclosure, a user may navigate away from the TOOLS display panel in order to perform other tasks while the full impedance test is running in the background. Then, once the full impedance test has finished, programmer 40 alerts the user. For example, programmer 40 may provide a graphical indication, e.g., a pop up box, flashing icon, or the like, and/or an audible indication, e.g., a beep or other sound, to let the user know that the full impedance test has finished and the results will be displayed once the user navigates back to the TOOLS display panel.

FIG. 29 illustrates another example programmer screen, in accordance with this disclosure. FIG. 29 depicts a lead setup panel, shown generally at 500, that displays first lead 502 (lead 1) and second lead 504 (lead 2). Lead setup panel 500 allows a user to combine fluoroscopic images with representations of the implanted leads, e.g., leads 502, 504. In addition, lead setup panel 500 displays a graphic of the device housing with a device header, shown generally at 506. In accordance with this disclosure, device header 506 includes a color-coded graphical representation of electrodes 0-7 of lead 1 and electrodes 8-15 of lead 2, for example, to indicate the results of a unipolar impedance test. In FIG. 29, electrodes 0-7 of lead 1 are colored green and the display includes text indicating that the lead is "Inserted OK," as seen at 508. Electrodes 8-15 of lead 2, however, are colored red and the display includes text advising the user to "Check Insertion," as seen at 510. The "check lead insertion" button, shown at 512, performs a unipolar impedance test on the implanted leads. As described above, it may be desirable to perform a full impedance test on the device based on the results of the unipolar impedance test. In some examples, a RUN FULL TEST button may appear, or become enabled, on lead setup panel 500 if programmer 40 determines that one or more electrodes are suspect or fail the unipolar impedance test. In other examples, the user may simply navigate to the TOOLS display panel and press a button run the full impedance test. Again, a user may perform a full impedance test even if all electrodes "pass" the unipolar impedance test.

In this manner, the color-coded graphical techniques described above with respect to FIGS. 28 and 29 allow a user to quickly and easily understand a connectivity status for each electrode of one or more implanted leads as determined by a unipolar impedance test, for example. Based on the results of a unipolar impedance test, the user may then be prompted to run a more complete impedance test, e.g., a bipolar impedance test. In other examples, the user may only be able to test electrode impedances with a bipolar impedance test of the available electrodes.

Figure 30:
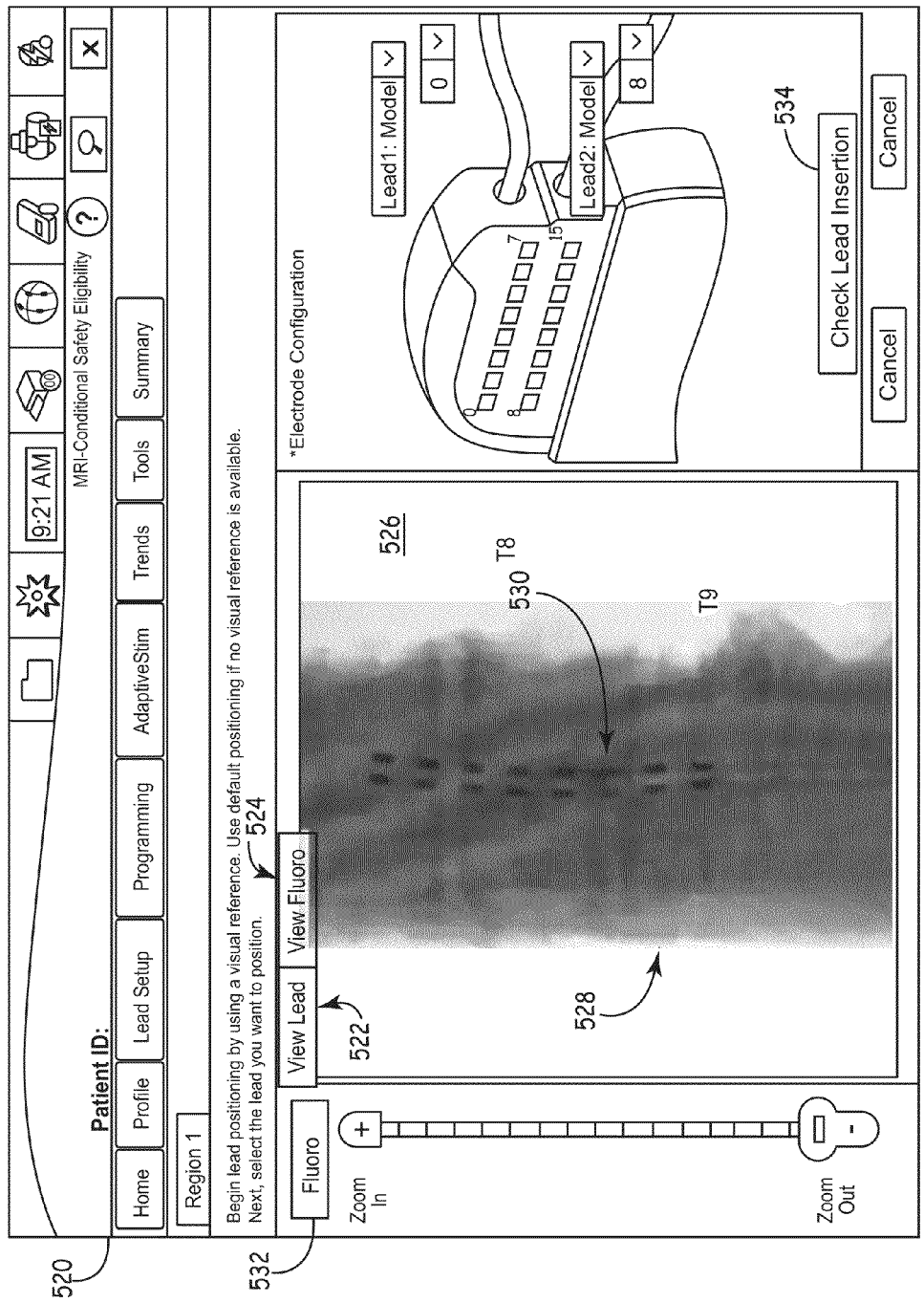
FIG. 30 illustrates an example programmer screen showing anatomy of the patient.
Figure 31:
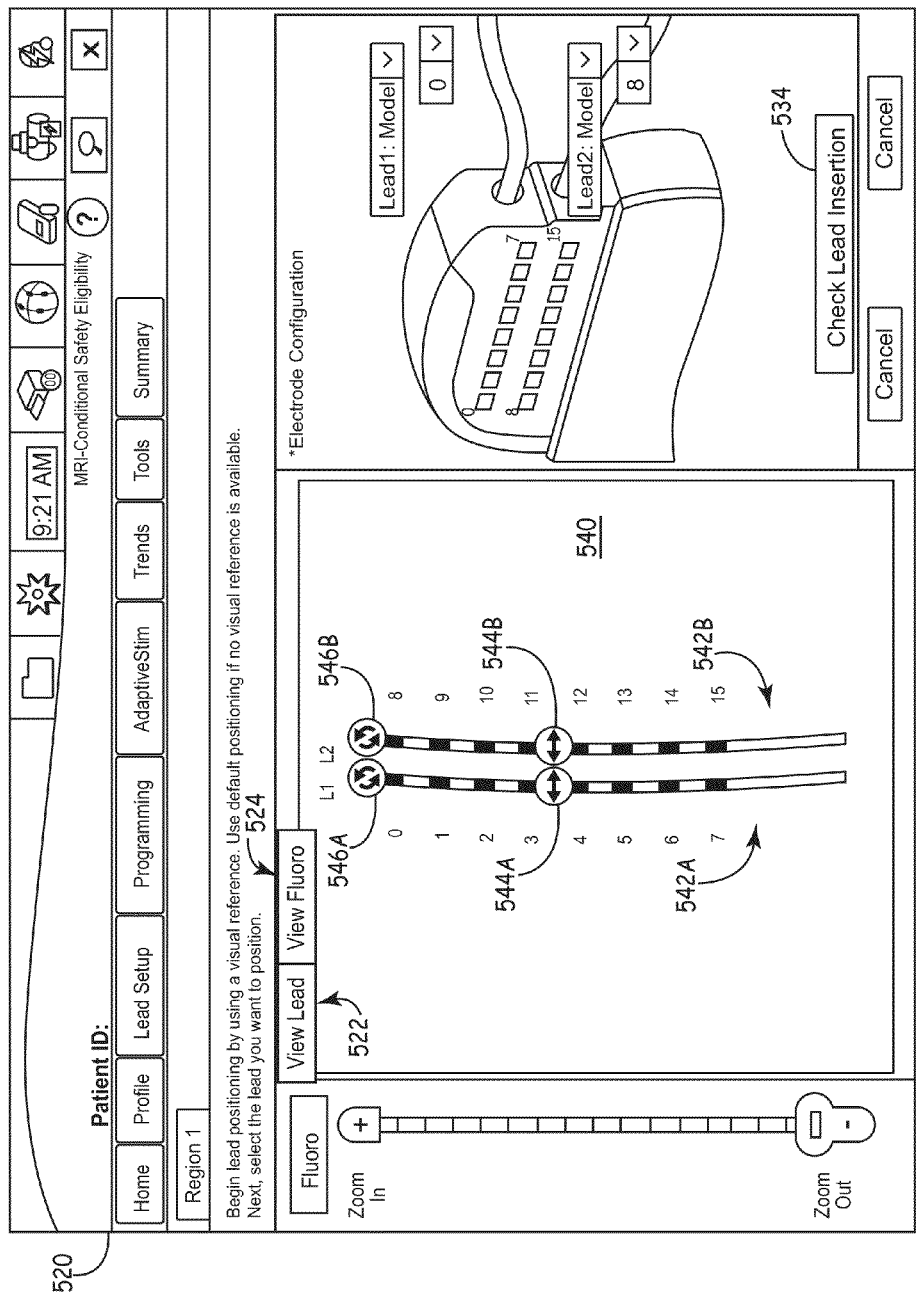
FIG. 31 illustrates an example programmer screen showing a representation of leads implanted within the patient.

FIGS. 30 and 31 are screen diagrams illustrating alternatives to the lead setup panel of FIG. 29. Instead of showing lead representations over patient anatomy, the lead representations and the patient anatomy are available in different windows in the examples of FIGS. 30 and 31. FIG. 30 illustrates an example programmer screen showing anatomy of patient 6. As shown in FIG. 30, user interface 520 (an example of user interface 59), depicts a lead setup panel that includes lead view 522 and fluoro view 524. Fluoro view 524 has been selected to display window 526 that includes anatomy of patient 6. In the example of FIG. 30, the anatomy of patient 6 is provided from a fluoroscopy image of patient 6. The specific fluoroscopy image may be selected from a stored file using image selection button 532.

Window 526 illustrates a portion of patient anatomy that includes implanted leads 530 used to deliver electrical stimulation. Window 526 also includes spinal column 528 in which vertebrae T8 and T9 are discernable. Window 526 allows the user to view the shape of each lead and distance between each of electrodes 530. Based on this information, the user may select lead view 522 to adjust the representation of leads 530 (as shown in FIG. 31.) The user may also zoom in or out of window 526 and move to a different location of spinal column 528.

Although window 526 provides patient anatomy as imaged with fluoroscopy, any other imaging modality may be used in other examples. For example, images of patient anatomy may be generated using MRI, x-ray, computed tomography, positron emission tomography, or any other imaging modality appropriate for viewing patient anatomy and implanted electrodes. As described in FIG. 29, the user may select check lead insertion button 534 to perform impedance tests on the available electrodes.

FIG. 31 illustrates an example programmer screen showing a representation of leads implanted within the patient. Once the user has identified the shape and/or relative locations of the implanted leads, the user may select lead view 522 to cause user interface 520 to display window 540. The user may then interact with leads 542A and 542B (collectively "leads 542") to adjust the shape and position of leads 542 to represent the locations of each lead and electrode as implanted within patient 6. The user may select either lead 542A or 542B to adjust the position of one lead with respect to the other. When adjusting the lead position, the user may adjust the vertical and/or horizontal position of the lead within window 540.

Curve inputs 544A and 544B may allow the user to modify the magnitude and direction of the curvature of each lead. Curve inputs 544A and 544B may be centered along the length of each lead. In other examples, curve inputs 544A and 544B may be moved to any position along the length of the respective lead to create asymmetrical curvatures in the respective lead. Rotational inputs 546A and 546B may allow the user to rotate each of leads 542 in the plane of window 540. In other words, rotational inputs 546A and 546B may be selected and moved to pivot the respective lead about a pivot point. Although the pivot point may be positioned at the longitudinal middle of each lead, the user may move the pivot point to any position along the length of each lead in other examples. User interface 520 may allow the user to switch between lead view 522 and fluoro view 524 as desired by the user.

Figure 32:
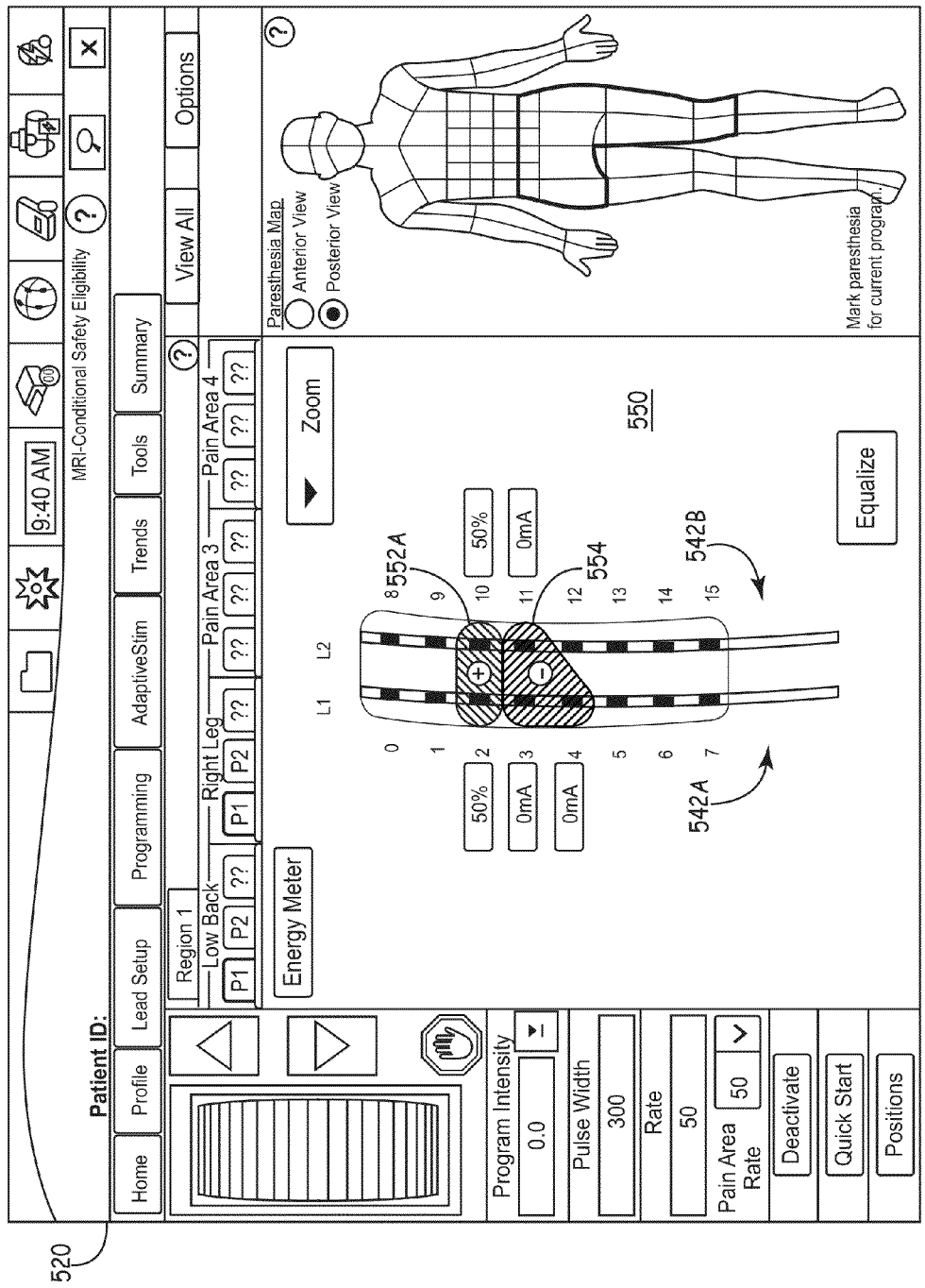
FIGS. 32-34 illustrate example programmer screens stimulation zones.
Figure 33:
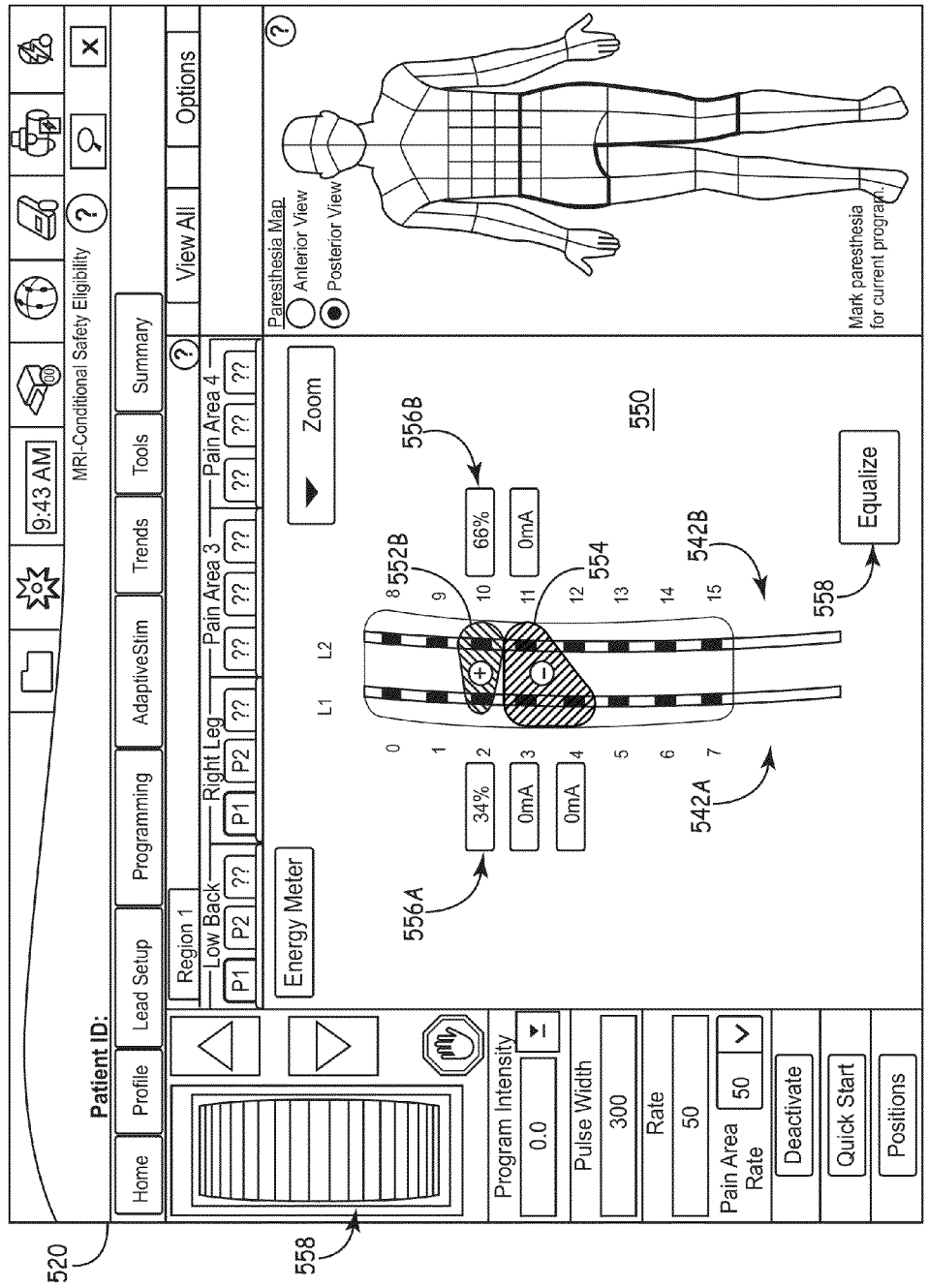
Figure 34:
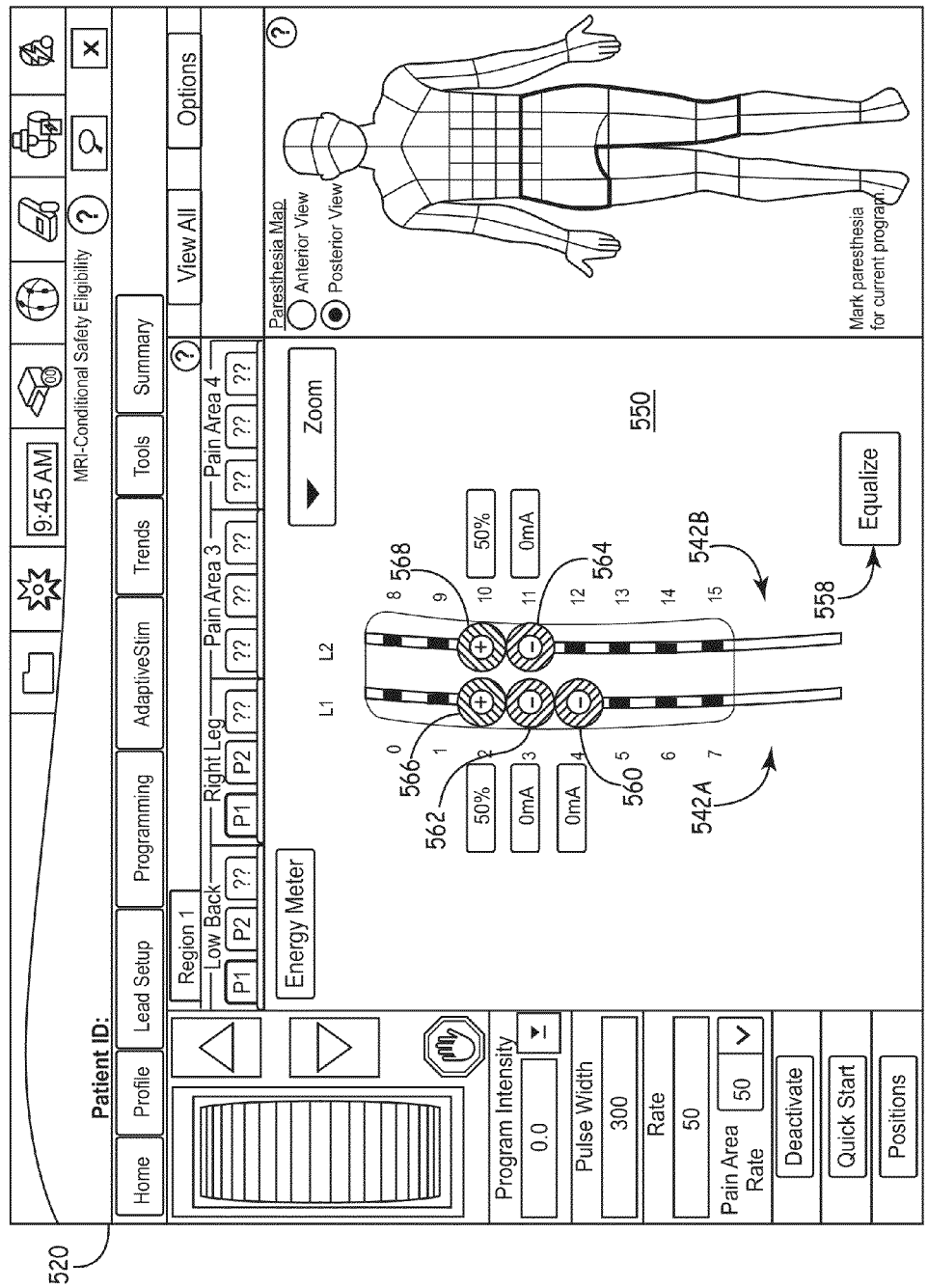

FIGS. 32-34 illustrate example programmer screens with various stimulation zones. User interface 520 of FIG. 32 may be similar to user interface 59 described above, but user interface 520 does not provide an image of patient anatomy overlaid by representations of the implanted leads. As shown in FIG. 32, user interface 520 provides leads 542A and 542B in window 550 for programming stimulation within window 550. Stimulation zone 554 indicates that electrodes 3, 4, and 11 are recruited as cathodes. Accordingly, stimulation zone 552A indicates that electrodes 2 and 10 are recruited as anodes. User interface 520 may allow the user to stretch or shrink zones 552A and 554, add additional stimulation zones, or delete existing stimulation zones.

As shown in FIG. 33, user interface 520 provides modified stimulation zone 552B from stimulation zone 552A of FIG. 32. By selecting contribution indicator 556B and then using scroll wheel 558 or associated arrows to adjust the contribution of the corresponding electrode 10, the user may create modified stimulation zone 552B. Because contribution indicator 556B indicates that electrode 10 contributes 66 percent of the anode current, contribution indicator 556A indicates that electrode 2 contributes 34 percent of the anode current. Accordingly, the shape of stimulation zone 552B is skewed such that a greater area of stimulation zone 552B covers electrode 10 instead of electrode 2. In the example of FIG. 33, the shape of stimulation zone 552B is created by generating a radius for each electrode of the stimulation zone proportional to the electrode contribution and generating a line between each radius Equalize button 558 may be selected by the user to equalize or balance the contributions of each cathode or anode used to deliver stimulation to patient 6. As shown in FIG. 34, the user has selected equalize button 558 to equalize the contributions of electrodes from stimulation zones 552B and 554, respectively. The resulting equalization of the cathodes and the anodes makes the contribution of all anodes, and all cathodes, equal to each other. In addition, equalization may "break up" the previous stimulation zones into separate stimulation zones for each electrode. In other words, "breaking up" a stimulation zone may include replacing the single stimulation zone for multiple electrodes with separate zones for each electrode within the previous stimulation zone. Therefore, separate stimulation zones 560, 562, 564, 566, and 568 have been created in the example of FIG. 34. Although equalizing stimulation zones may always create separate stimulation zones for each electrode, the user may be prompted to keep the current stimulation zones or break the current stimulation zones into separate zones for each electrode. In some examples, the user may not be allowed to rejoin separate stimulation zones. However, in other examples, the user may be allowed to join separate stimulation zones, e.g., stimulation zones 566 and 568, into a single stimulation zone for anodes.

Figure 35:
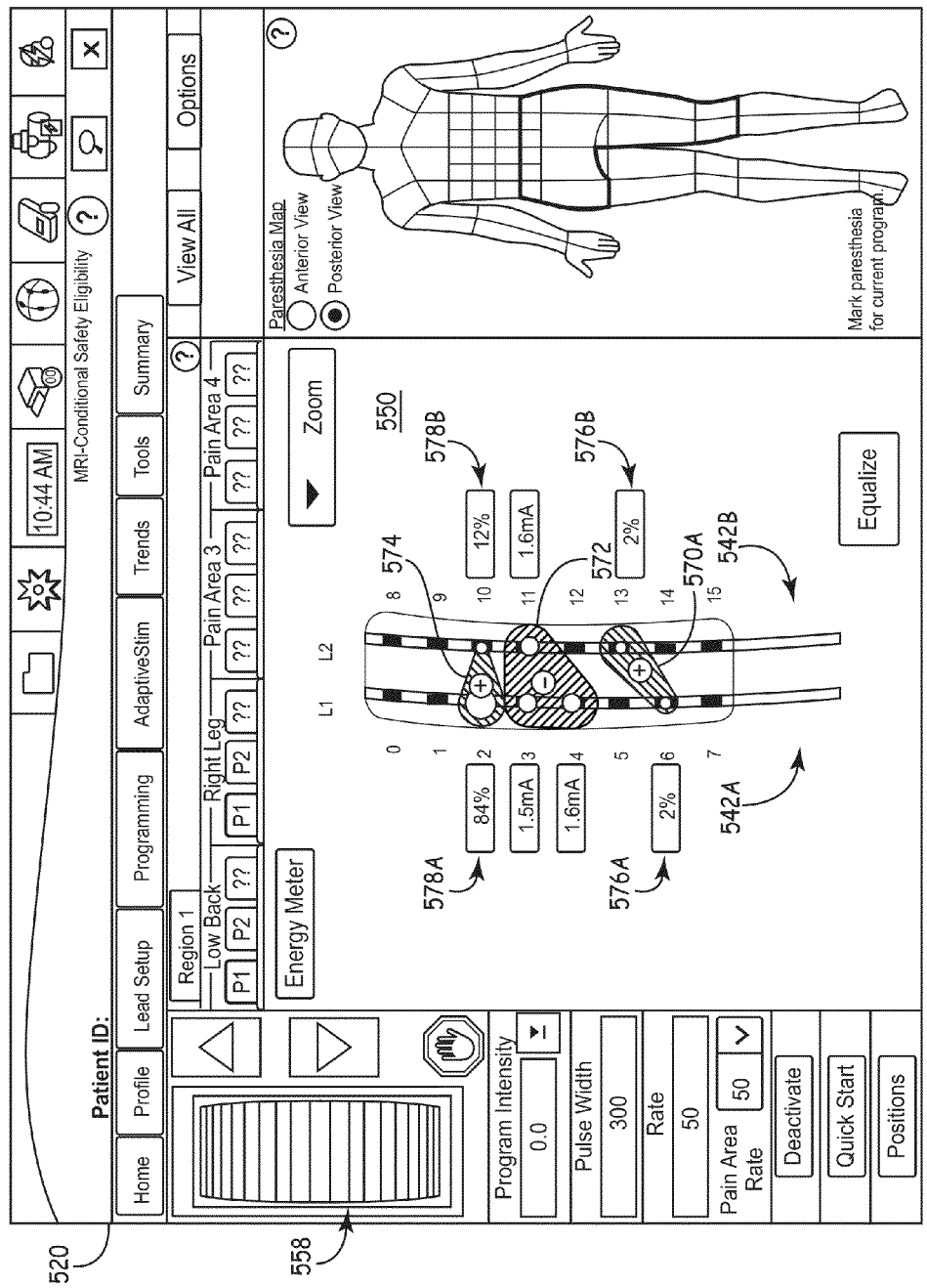
FIGS. 35-36 illustrate example programmer screens with changes to stimulation zones due to changing electrode contributions.
Figure 36:
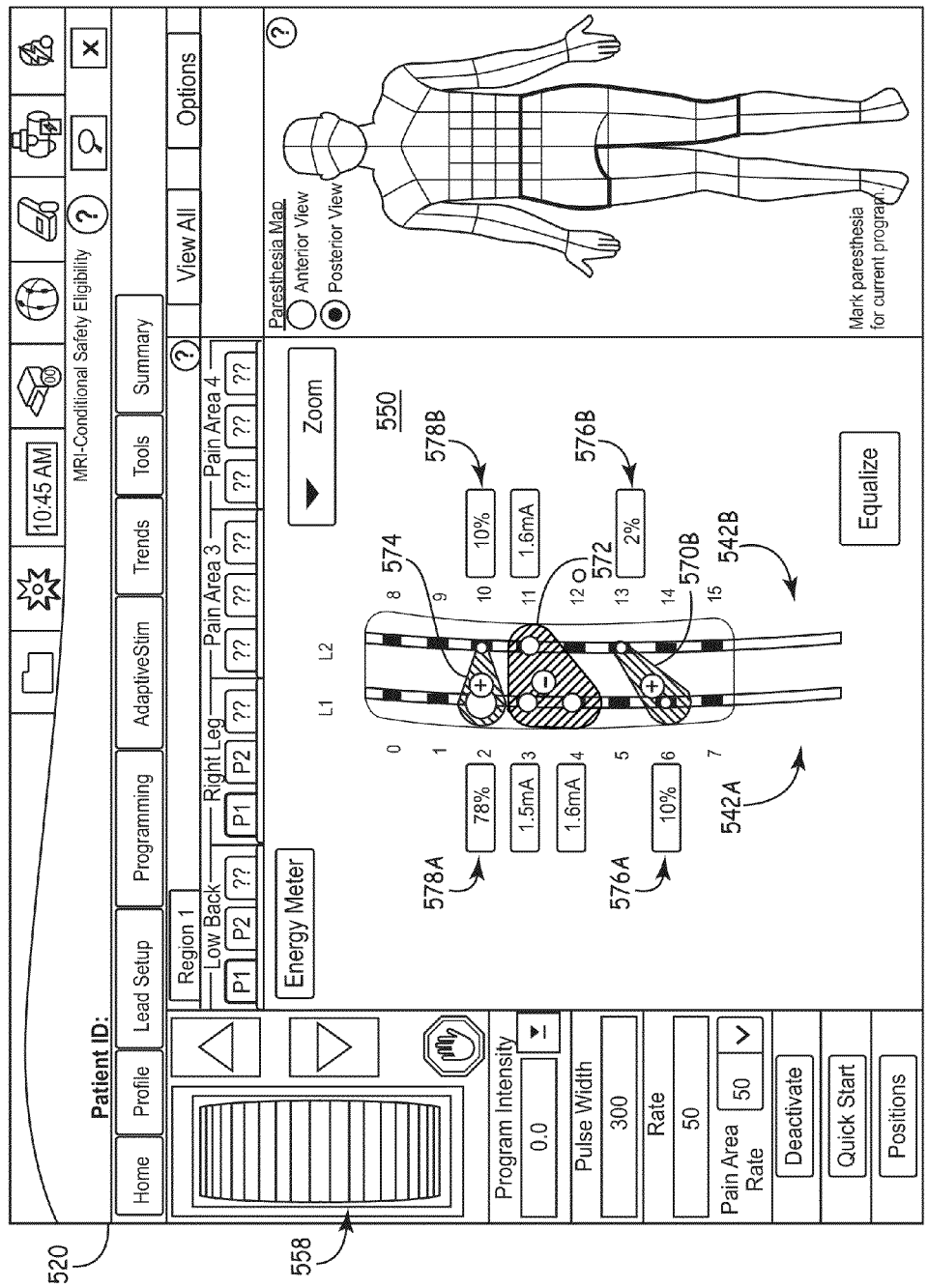

FIGS. 35 and 36 illustrate example programmer screens with changes to stimulation zones due to changing electrode contributions. As shown in FIG. 36, window 550 provides stimulation zones 574, 572, and 570A. Contributions indicators 576A, 576B, 578A, and 578B indicate the anode contributions for each electrodes 6, 13, 2, and 10, respectively. Since electrode 2 contributes 84 percent of the current source, the area of stimulation zone 574 over electrode 2 is much larger than the area of stimulation zone 574 over electrode 10. In addition, the field shape of electrode 2 is the largest field shape of any other anode due to the largest contribution of electrode 2. The sizes of stimulation zones may only be relative to contributions within each stimulation zone. For example, even though the electrodes of stimulation zone 570A contribute a total of 4 percent of current, the size of stimulation zone 570A is relatively similar to that of stimulation zone 574 that contributes 96 percent of the current. However, the field shapes of each anode within stimulation zones 570A and 574 are generally representative of each electrode contribution or amplitude. In other examples, stimulation zones may be sized to visually indicate a relative contribution of each stimulation zone to the overall delivered current.

When a new stimulation zone is added to window 550, each electrode of the new stimulation zone may be attributed a default current contribution that is deducted from existing electrodes of the same polarity. In the example of FIG. 35, stimulation zone 570A has just been added to window 550. Therefore, electrodes 6 and 13 were each given a default contribution of only 2 percent of the overall current of all anodes. This new contribution was deducted from electrodes 2 and 10 of stimulation zone 574. The default contribution for newly added electrodes may be of a minimal amplitude to avoid discomfort to patient 6 when testing a new area of stimulation. In other examples, the default contribution of new electrodes may be zero or a higher amplitude based on the preferences of the user.

Once the new stimulation zone 570A has been added to window 550, the user may increase or decrease the amplitude of each electrode within stimulation zone 570A. The user may first select contribution indicator 576A, for example, and use scroll wheel 558 or associated arrows to increase or decrease the amplitude of the associated electrode 6. Although the user may be limited to changing the contribution of one electrode at a time, other examples may allow the user to select multiple electrodes within a stimulation zone and increase or decrease the selected electrodes simultaneously.

As shown in FIG. 36, the user has changed the contribution of electrode 6 with scroll wheel 558. Stimulation zone 570A of FIG. 35 included a contribution oft percent from electrode 6. After changing the contribution of electrode 6, modified stimulation zone 570B of FIG. 36 has changed shape to indicate the larger contribution from electrode 6 than the contribution from unchanged electrode 13. In stimulation zone 570B, the contribution of electrode 6 is 10 percent.

As the contribution, or amplitude, of one electrode is changed, the contributions of other similar electrodes may be automatically adjusted to maintain a total contribution of 100 percent from all anodes, for example. Since the contribution of electrode 6 has increased from 2 percent in stimulation zone 570A to 10 percent in stimulation zone 570B, the contributions of electrodes 2 and 10 have decreased to 78 percent and 10 percent, respectively. In other examples, user interface 520 may allow the user to specify which electrode contributions should be affected by adjusting another electrode contribution. Alternatively, user interface 520 may prompt the user to specific new contributions for remaining electrodes after one or more electrode contributions have changed.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various aspects of the disclosure have been described. These and other aspects are within the scope of the following claims.

The invention claimed is:

1. A method comprising:
receiving, via a programmer for an electrical stimulator, user input indicating a target stimulation zone; and
controlling, by a processor, the electrical stimulator to transition electrical stimulation from an initial stimulation zone to the target stimulation zone via one or more intermediate stimulation zones defined, based on the target stimulation zone, before controlling the electrical stimulator to transition the electrical stimulation.

2. The method of claim 1, further comprising automatically generating one or more intermediate stimulation zones based on the initial stimulation zone and the target stimulation zone.

3. The method of claim 1, further comprising graphically displaying the transition from the initial stimulation zone to the target stimulation zone.

4. The method of claim 1, wherein the one or more intermediate stimulation zones are generated based on a predetermined rate of change in stimulation amplitude.

5. The method of claim 1, further comprising:
displaying, via the programmer, a transition control input comprising one or more indicators, each of the one or more indicators corresponding to a respective one of the one or more intermediate stimulation zones.

6. The method of claim 5, wherein the one or more indicators are either linearly or non-linearly related to one another.

7. The method of claim 5, wherein a number of the one or more indicators on the transition control input is based on the user input indicating the target stimulation zone.

8. The method of claim 5, further comprising receiving, via the transition control input, user input that initiates the transition.

9. The method of claim 8, wherein receiving, via the transition control input, user input that initiates the transition comprises receiving user input via an initiate input.

10. The method of claim 5, wherein the transition control input comprises a slider bar input.

11. The method of claim 10, further comprising graphically dragging a slider on the slider bar from a first indicator of the one or more indicators to a second indicator of the one or more indicators, wherein controlling the electrical stimulator to transition electrical stimulation from an initial stimulation zone to the target stimulation zone via one or more intermediate stimulation zones comprises controlling the electrical stimulator to transition electrical stimulation from the initial stimulation zone to the target stimulation zone based on the dragging of the slider from the first indicator to the second indicator via any intermediate indicators.

12. The method of claim 5, wherein the transition control input comprises an increment input and a decrement input, the method further comprising:
receiving user input via the increment input or the decrement input, wherein the increment input controls the electrical stimulator to transition the initial stimulation zone stepwise toward the target stimulation zone through one of the one or more intermediate stimulation zones, and wherein the decrement input controls the electrical stimulator to transition the initial stimulation zone stepwise away from the target stimulation zone through one of the one or more intermediate stimulation zones.

13. The method of claim 1, wherein each of the one or more intermediate zones are defined by a respective set of stimulation parameters that are different than a respective set of stimulation parameters that define either the initial stimulation zone or the target stimulation zone.

14. The method of claim 13, wherein the set of stimulation parameters that define a stimulation zone comprises a plurality of electrode contributions to the stimulation zone, wherein at least two of the plurality of electrode contributions are not equal to one another, the method further comprising:
receiving, via the programmer for the electrical stimulator, user input that balances the at least two electrode contributions such that the at least two electrode contributions are equal to one another.

15. The method of claim 1, wherein receiving, via a programmer for an electrical stimulator, user input indicating a target stimulation zone comprises receiving, via the programmer for the electrical stimulator, user input that graphically defines the target stimulation zone.

16. The method of claim 15, wherein receiving, via the programmer for the electrical stimulator, user input that graphically defines the target stimulation zone comprises receiving, via the programmer for the electrical stimulator, user input that graphically manipulates at least one of a shape and a location of the initial stimulation zone in order to define the target stimulation zone.

17. The method of claim 1, further comprising delivering electrical stimulation to a patient during the transitioning.

18. The method of claim 1, further comprising receiving, via the programmer for the electrical stimulator, user input defining the initial stimulation zone.

19. The method of claim 1, further comprising receiving, via the programmer for the electrical stimulator, user input controlling the transition between each of the intermediate stimulation zones and the target stimulation zone.

20. The method of claim 1, wherein each of the initial stimulation zone, target stimulation zone, and one or more intermediate stimulation zones are defined by electrodes of the same polarity.

21. The method of claim 1, wherein controlling the electrical stimulator to transition electrical stimulation from the initial stimulation zone to the target stimulation zone comprises controlling the electrical stimulator to transition electrical stimulation longitudinally along a lead from the initial stimulation zone to the target stimulation zone via the one or more intermediate stimulation zones.

22. The method of claim 1, wherein controlling the electrical stimulator to transition electrical stimulation from the initial stimulation zone to the target stimulation zone comprises controlling the electrical stimulator to transition electrical stimulation transversely across two or more leads from the initial stimulation zone to the target stimulation zone.

23. The method of claim 1, further comprising receiving user input selecting a type of transition from the initial stimulation zone to the target stimulation zone, wherein controlling the electrical stimulator to transition electrical stimulation from an initial stimulation zone to the target stimulation zone comprises controlling the electrical stimulator to transition electrical stimulation according to the selected type of transition.

24. A system comprising:
a user interface configured to receive user input indicating a target stimulation zone; and
a processor configured to control an electrical stimulator to transition electrical stimulation from an initial stimulation zone to the target stimulation zone via one or more intermediate stimulation zones defined, based on the target stimulation zone, before controlling the electrical stimulator to transition the electrical stimulation.

25. The system of claim 24, wherein the processor is configured to automatically generate the one or more intermediate stimulation zones based on the initial stimulation zone and the target stimulation zone.

26. The system of claim 24, wherein the user interface is configured to graphically display the transition from the initial stimulation zone to the target stimulation zone.

27. The system of claim 24, wherein the one or more intermediate stimulation zones are generated based on a predetermined rate of change in stimulation amplitude.

28. The system of claim 27, wherein the user interface is configured to display a transition control input comprising one or more indicators, each of the one or more indicators corresponding to a respective one of the one or more intermediate stimulation zones.

29. The system of claim 27, wherein the user interface is configured to receive user input relative to one or more indicators that are either linearly or non-linearly related to one another.

30. The system of claim 28, wherein the number of indicators on the transition control input is based on the user input indicating the target stimulation zone.

31. The system of claim 28, wherein the transition control input comprises a slider bar input.

32. The system of claim 31, wherein:
the user interface is configured to, in response to a user input, graphically drag a slider on the slider bar from a first indicator of the one or more indicators to a second indicator of the one or more indicators; and
the processor is configured to control the electrical stimulator to transition electrical stimulation from the initial stimulation zone to the target stimulation zone based on the dragging of the slider from the first indicator to the second indicator via any intermediate indicators.

33. The system of claim 27, wherein:
the transition control input comprises an increment input and a decrement input;
the user interface is configured to receive user input via the increment input or the decrement input;
based on the increment input, the processor controls the electrical stimulator to transition the initial stimulation zone stepwise toward the target stimulation zone through one of the one or more intermediate stimulation zones; and
based on the decrement input, the processor controls the electrical stimulator to transition the initial stimulation zone stepwise away from the target stimulation zone through one of the one or more intermediate stimulation zones.

34. The system of claim 24, wherein each of the one or more intermediate zones are defined by a respective set of stimulation parameters that are different than a respective set of stimulation parameters that define either the initial stimulation zone or the target stimulation zone.

35. The system of claim 24, wherein the user interface is configured to receive user input that graphically defines the target stimulation zone.

36. The system of claim 35, wherein the user interface is configured to receive user input that graphically manipulates at least one of a shape and a location of the initial stimulation zone, and wherein the processor defines the target stimulation zone based on at least one of the manipulated shape and the manipulated location.

37. The system of claim 24, further comprising an electrical stimulator configured to deliver electrical stimulation to a patient during the transition from the initial stimulation zone to the target stimulation zone via the one or more intermediate stimulation zones.

38. The method of claim 24, wherein each of the initial stimulation zone, target stimulation zone, and one or more intermediate stimulation zones are defined by electrodes of the same polarity.

39. The system of claim 24, further comprising a programmer that comprises the user interface and the processor.

40. The system of claim 24, further comprising the electrical stimulator that comprises the processor.

41. The system of claim 24, further comprising a programmer and the electrical stimulator, wherein each of the programmer and the electrical stimulator contribute to automatic generation of one or more intermediate stimulation zones based on the initial stimulation zone and the target stimulation zone.

42. The system of claim 24, wherein the processor is configured to control the electrical stimulator to transition electrical stimulation longitudinally along a lead from the initial stimulation zone to the target stimulation zone via the one or more intermediate stimulation zones.

43. The system of claim 24, wherein the processor is configured to control the electrical stimulator to transition electrical stimulation transversely across two or more leads from the initial stimulation zone to the target stimulation zone.

44. The system of claim 24, wherein:
the user interface is configured to receive user input selecting a type of transition from the initial stimulation zone to the target stimulation zone; and
the processor is configured to control the electrical stimulator to transition electrical stimulation according to the selected type of transition.

45. A system comprising:
means for receiving user input indicating a target stimulation zone; and
means for controlling an electrical stimulator to transition electrical stimulation from an initial stimulation zone to the target stimulation zone via one or more intermediate stimulation zones defined, based on the target stimulation zone, before controlling the electrical stimulator to transition the electrical stimulation.

46. The system of claim 45, further comprising means for automatically generating one or more intermediate stimulation zones based on the initial stimulation zone and the target stimulation zone.

47. The system of claim 45, wherein the means for controlling the electrical stimulator to transition electrical stimulation from the initial stimulation zone to the target stimulation zone comprises means for controlling the electrical stimulator to transition electrical stimulation longitudinally along a lead from the initial stimulation zone to the target stimulation zone via the one or more intermediate stimulation zones.

48. The system of claim 45, wherein the means for controlling the electrical stimulator to transition electrical stimulation from the initial stimulation zone to the target stimulation zone comprises means for controlling the electrical stimulator to transition electrical stimulation transversely across two or more leads from the initial stimulation zone to the target stimulation zone.

49. The system of claim 45, further comprising means for receiving user input selecting a type of transition from the initial stimulation zone to the target stimulation zone, wherein the means for controlling the electrical stimulator to transition electrical stimulation from an initial stimulation zone to the target stimulation zone comprises means for controlling the electrical stimulator to transition electrical stimulation according to the selected type of transition.

50. A non-transitory computer-readable storage medium comprising instructions that cause at least one processor to:
receive user input indicating a target stimulation zone; and
control an electrical stimulator to transition electrical stimulation from an initial stimulation zone to the target stimulation zone via one or more intermediate stimulation zones defined, based on the target stimulation zone, before controlling the electrical stimulator to transition the electrical stimulation.

51. The non-transitory computer-readable storage medium of claim 50, further comprising instructions that cause the at least one processor to automatically generate the one or more intermediate stimulation zones based on the initial stimulation zone and the target stimulation zone.

52. A system comprising:
a user interface configured to receive user input indicating a target stimulation zone; and
a processor configured to control an electrical stimulator to transition electrical stimulation longitudinally along a lead from an initial stimulation zone to the target stimulation zone via one or more intermediate stimulation zones defined based on the target stimulation zone.

53. The system of claim 52, wherein the one or more intermediate stimulation zones are generated based on a pre-determined rate of change.

54. A system comprising:
a user interface configured to receive user input indicating a target stimulation zone; and
a processor configured to control an electrical stimulator to transition electrical stimulation transversely across two or more leads from an initial stimulation zone to the target stimulation zone via one or more intermediate stimulation zones defined based on the target stimulation zone.

55. The system of claim 54, wherein the one or more intermediate stimulation zones are generated based on a pre-determined rate of change.

56. A system comprising:
a user interface configured to:
receive user input indicating a target stimulation zone; and
receive user input selecting a type of transition from an initial stimulation
zone to the target stimulation zone; and
a processor configured to control an electrical stimulator to transition electrical stimulation according to the selected type of transition and from the initial stimulation zone to the target stimulation zone via one or more intermediate stimulation zones defined based on the target stimulation zone.

* * * * *